US011305061B2

(12) United States Patent
Grimoldby et al.

(10) Patent No.: US 11,305,061 B2
(45) Date of Patent: Apr. 19, 2022

(54) MEDICAMENT DELIVERY DEVICES

(71) Applicant: Owen Mumford Limited, Woodstock (GB)

(72) Inventors: James Grimoldby, Oxfordshire (GB); Oliver Gareth Hyde, Oxfordshire (GB); Matthew Watts, Oxfordshire (GB); Lee Pearson, Oxfordshire (GB)

(73) Assignee: Owen Mumford Limited, Oxford (GB)

( * ) Notice: Subject to any disclaimer, the term of this patent is extended or adjusted under 35 U.S.C. 154(b) by 469 days.

(21) Appl. No.: 15/757,159

(22) PCT Filed: Sep. 2, 2016

(86) PCT No.: PCT/GB2016/052717
§ 371 (c)(1),
(2) Date: Mar. 2, 2018

(87) PCT Pub. No.: WO2017/037470
PCT Pub. Date: Mar. 9, 2017

(65) Prior Publication Data
US 2018/0250471 A1 Sep. 6, 2018

(30) Foreign Application Priority Data
Sep. 3, 2015 (GB) .................................. 1515650

(51) Int. Cl.
A61M 5/20 (2006.01)
A61M 5/315 (2006.01)
(Continued)

(52) U.S. Cl.
CPC ...... A61M 5/2033 (2013.01); A61M 5/31553 (2013.01); A61M 5/3204 (2013.01);
(Continued)

(58) Field of Classification Search
CPC .............. A61M 5/2033; A61M 5/3202; A61M 5/3204; A61M 5/31501; A61M 5/20;
(Continued)

(56) References Cited

U.S. PATENT DOCUMENTS

2008/0132838 A1 6/2008 Wyrick
2013/0102971 A1 4/2013 Olson
(Continued)

FOREIGN PATENT DOCUMENTS

EP 2399629 A1 12/2011
EP 2441487 A1 4/2012
(Continued)

OTHER PUBLICATIONS

Jan. 19, 2017 Transmittal of ISR and Written Opinion of International Searching Authority for PCT/GB2016/052717.
(Continued)

Primary Examiner — Rebecca E Eisenberg
Assistant Examiner — Tania Ismail
(74) Attorney, Agent, or Firm — Quarles & Brady LLP

(57) ABSTRACT

A device for delivery of a medicament from a container (10) having an outlet (16) at a distal end of the container (10) and a stopper (22) for containing the medicament in the container (10). The device comprises a housing (110, 140), a drive element (300) arranged to move in the distal direction to cooperate with the container (10), a drive mechanism comprising a trigger component (200), the drive mechanism being arranged to hold the drive element (300) in a starting position and to move the drive element (300) in the distal direction from the starting position upon displacement of the trigger component (200) from a working position to a firing position, an interlock component (250) received in the housing (110, 140) and arranged for movement with respect to the housing (110, 140) from a first position to a second
(Continued)

position, and at least one flexible locking member (214) arranged to cooperate with a stop face (160) associated with the housing (110, 140) to prevent displacement of the trigger component (200) to the firing position when the interlock component (250) is in the first position. Movement of the interlock component (250) towards the second position causes bending of the flexible locking member (214) away from the stop face (160) to allow displacement of the trigger component (200) to the firing position.

26 Claims, 34 Drawing Sheets

(51) Int. Cl.
*A61M 5/32* (2006.01)
*A61M 5/31* (2006.01)

(52) U.S. Cl.
CPC ......... *A61M 5/3146* (2013.01); *A61M 5/3156* (2013.01); *A61M 5/3157* (2013.01); *A61M 5/31585* (2013.01); *A61M 5/3257* (2013.01); *A61M 5/3287* (2013.01); *A61M 2005/206* (2013.01); *A61M 2005/208* (2013.01); *A61M 2005/2073* (2013.01); *A61M 2205/582* (2013.01); *A61M 2205/583* (2013.01)

(58) Field of Classification Search
CPC .......... A61M 5/31585; A61M 5/31571; A61M 5/3257; A61M 5/3287; A61M 5/31565; A61M 2205/583; A61M 2205/208; A61M 2205/2073

See application file for complete search history.

(56) References Cited

U.S. PATENT DOCUMENTS

| | | | |
|---|---|---|---|
| 2013/0281935 A1* | 10/2013 | Kemp | A61M 5/3202 604/197 |
| 2013/0289490 A1 | 10/2013 | Kemp et al. | |
| 2013/0317427 A1* | 11/2013 | Brereton | A61M 5/3158 604/111 |
| 2013/0317447 A1 | 11/2013 | Cowe | |
| 2014/0135705 A1 | 5/2014 | Hourmand et al. | |

FOREIGN PATENT DOCUMENTS

| | | | |
|---|---|---|---|
| EP | | 2468335 A1 | 6/2012 |
| WO | WO 2011/101382 A1 | | 8/2011 |
| WO | WO 2011/162686 A1 | | 12/2011 |
| WO | WO 2012/000875 A1 | | 1/2012 |
| WO | WO 2013/044172 A1 | | 3/2013 |
| WO | WO 2013/048310 A1 | | 4/2013 |
| WO | WO 2014/053451 A1 | | 4/2014 |
| WO | WO 2015/087090 A2 | | 6/2015 |

OTHER PUBLICATIONS

Search Report from corresponding United Kingdom Patent Application No. GB1515650.8 dated Feb. 12, 2016 (4 pages).

* cited by examiner

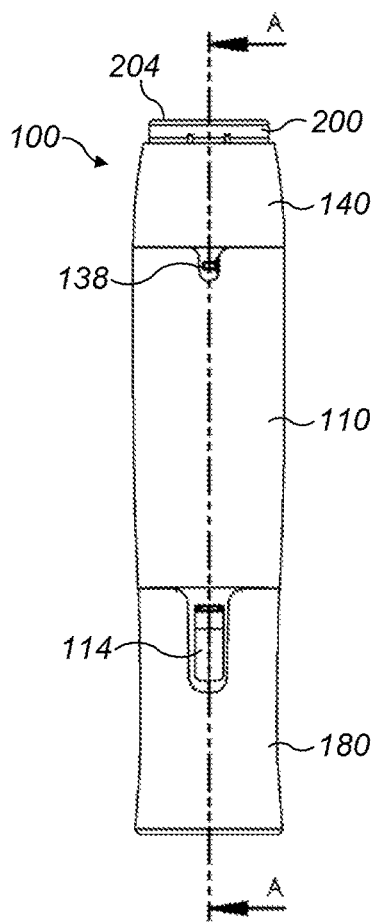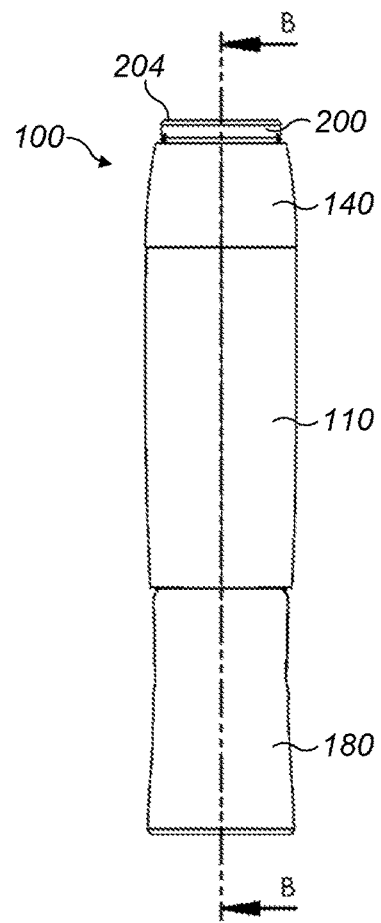
FIG. 1(a)      FIG. 1(b)
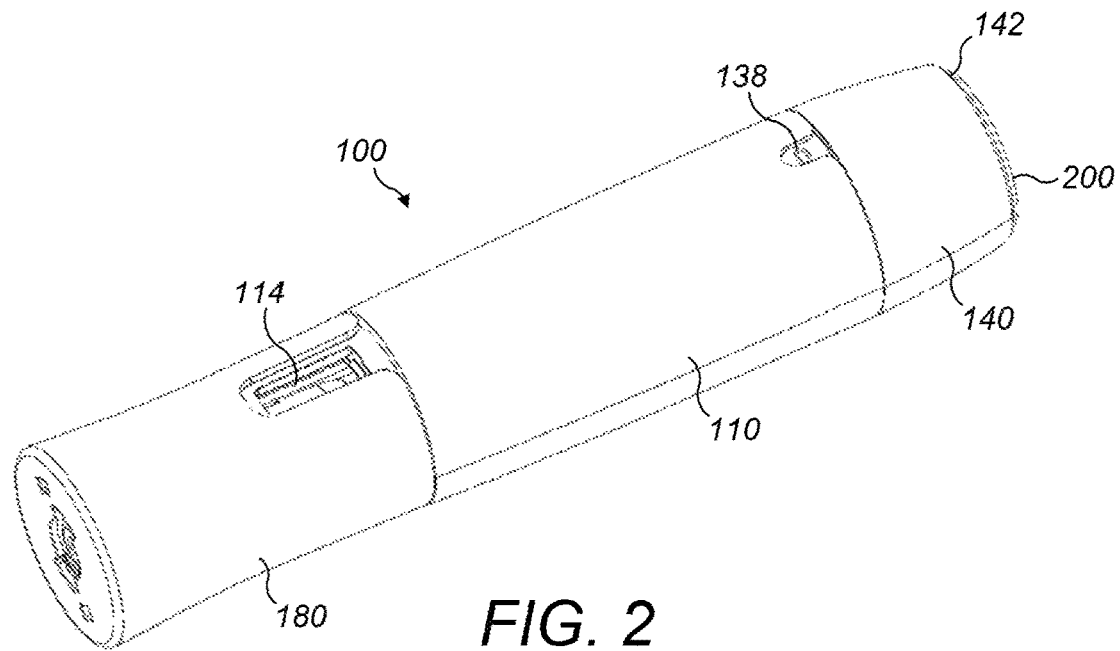
FIG. 2

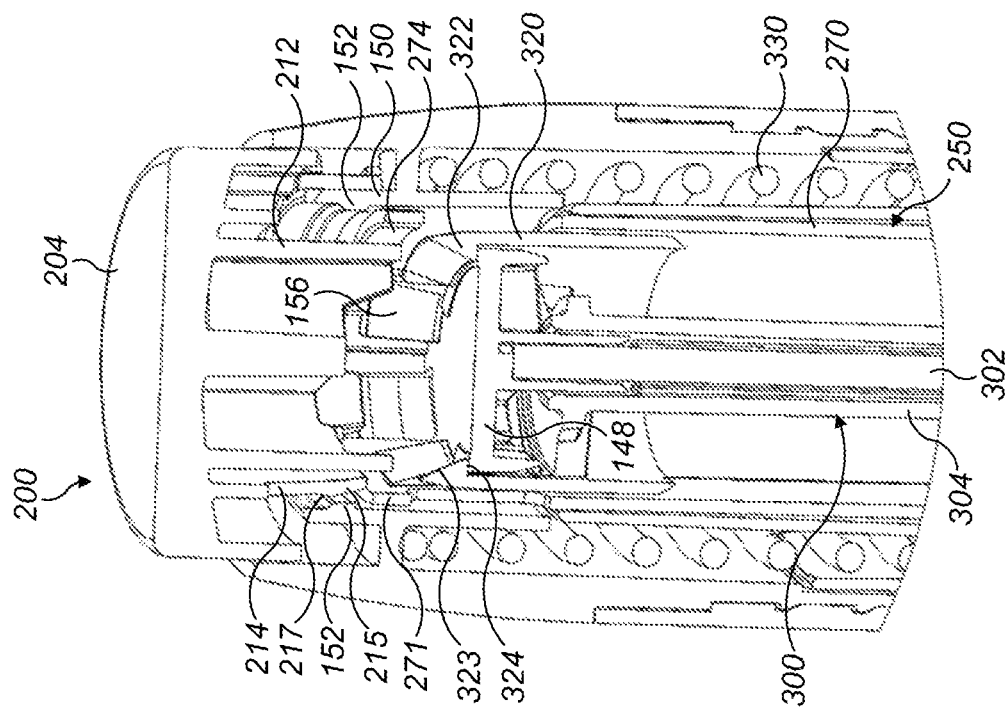
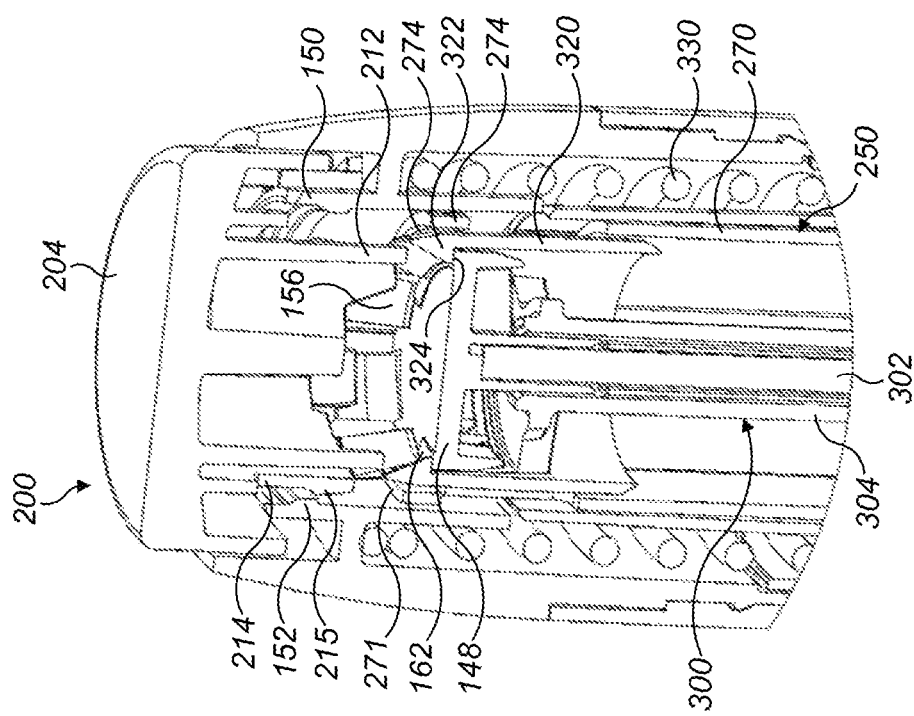
FIG. 20(a)
FIG. 20(b)

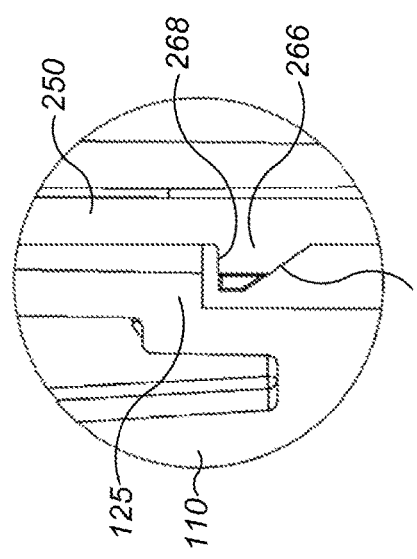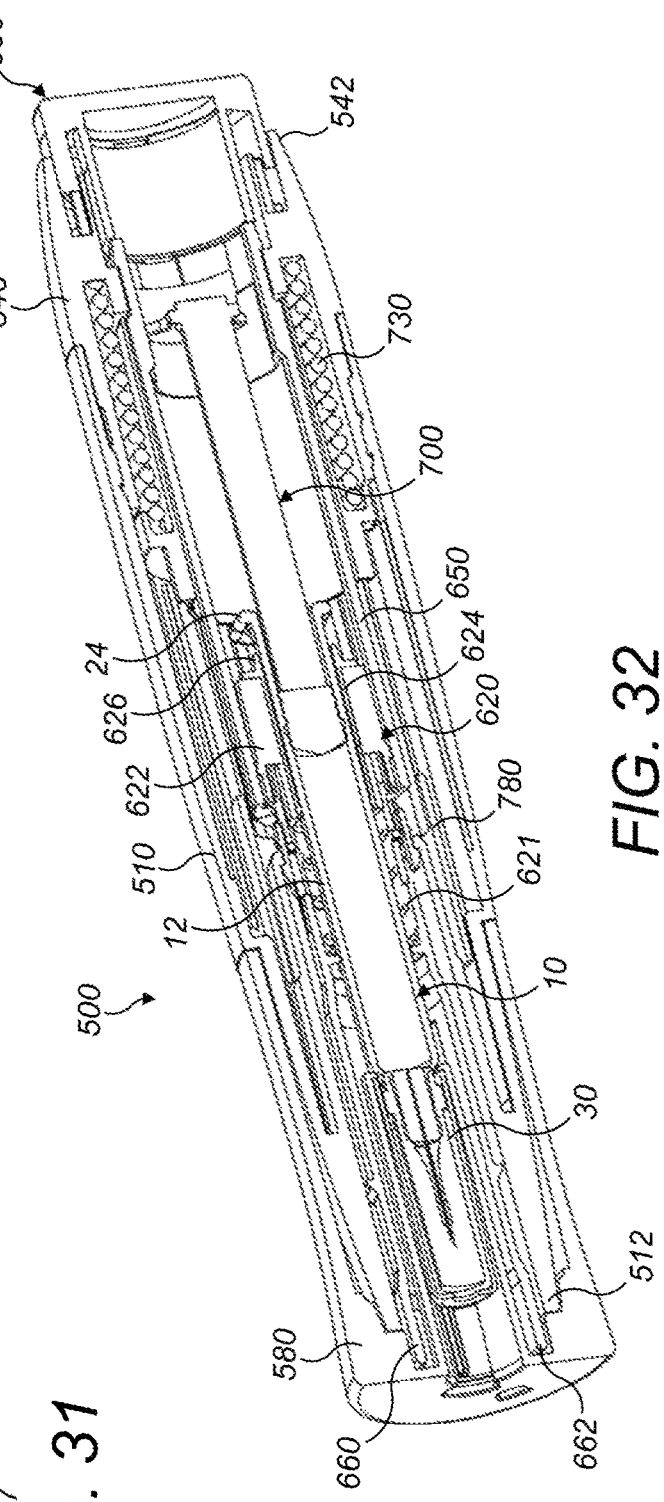

MEDICAMENT DELIVERY DEVICES

The present application is a § 371 submission of international application no. PCT/GB2016/052717, filed 2 Sep. 2016 and titled Medicament Delivery Devices, which was published in the English language on 9 Mar. 2017 with publication no. WO 2017/037470, and which claims the benefit of the filing date of GB 15 15650.8 filed 3 Sep. 2015, the contents of which are incorporated herein by reference.

The present invention relates to devices suitable for the delivery of a medicament to a patient. In particular, but not exclusively, the invention relates to variable-dose, single-use injection devices for hypodermic or subcutaneous injection of a medicament from a pre-filled container.

Injection devices designed for automatic or semi-automatic delivery of a single dose of a medicament are known in the art. Such devices typically include a housing that allows the user to grip the device, a pre-filled container containing the medicament, and a firing mechanism. The pre-filled container includes a tubular glass body, and a stopper slidably received in the barrel. A distal end of the container forms an outlet for the medicament. Commonly, the container is a pre-filled syringe, and a staked hypodermic needle is provided at the distal end of the syringe. A removable needle shield is typically provided to seal the needle prior to use. The needle shield is typically of two-part construction, with an elastomeric inner part for receiving the needle and a rigid outer cap or cover, for example of polypropylene, which is attached to the inner part and can be gripped by a user to pull the shield off the needle. This shield arrangement is known in the art as a rigid needle shield (RNS). One or more radially-projecting flanges are provided on the proximal end of the syringe body, which can be used to retain the syringe in the device. One example of a pre-filled syringe with a rigid needle shield is available under the registered trade mark Hypak (Becton Dickinson, N.J., USA).

With the syringe in place in the housing of the device, the distal end of the housing is closed by a cap. To prepare the device for use, the cap is removed. The cap is arranged to grip the rigid needle shield, so that removal of the cap pulls the rigid needle shield off the needle. The distal end of the housing is then placed against the skin. When activated, a spring-loaded plunger of the firing mechanism is released to push the stopper of the syringe distally towards the needle to inject the medicament.

In some devices, known as auto-injectors, needle insertion is also automatic. In such devices, the needle is initially retracted in the housing and the firing mechanism applies an insertion force to the syringe to cause the syringe to move distally with respect to the housing to an insertion position during an initial phase of operation of the firing mechanism. As a result, the needle advances out of the housing and into the patient's skin before injection of the medicament. By way of example, the present Applicant's International Patent Application Publication No. WO 2015/087090 describes an auto-injector in which the dosage of medicament delivered by the device can be selected by the user. The device described in WO 2015/087090 also includes an interlock arrangement that prevents accidental firing of the device.

In most auto-injectors, the syringe is guided for axial movement in the housing by a syringe carrier. The syringe carrier is arranged to hold the syringe and to move with the syringe to the insertion position of the syringe. When the cap is removed from the device to remove the needle shield from the syringe, the syringe and the syringe carrier may be pulled in the distal direction until the needle shield is released. Accordingly, the syringe carrier may be spring-biased in the proximal direction to return the syringe to its initial position relative to the housing after removal of the cap and the needle shield. In such arrangements, when the user of the device removes the cap, the user may be able to feel and hear the compression of the spring and the subsequent spring-back of the carrier and the syringe after the needle shield is released. These sensations can be unexpected and/or undesirable for the user.

In some auto-injectors, the insertion force is applied to the syringe by the action of the plunger on the stopper. When the plunger initially makes contact with the stopper, the stopper does not move relative to the syringe, but instead the syringe moves as a whole in the distal direction until it reaches an insertion position. Upon reaching the insertion position, further movement of the syringe body relative to the housing is blocked, and instead the stopper moves along the body to expel the medicament.

In such arrangements, the syringe carrier is arranged to contact a stop in the housing when the insertion position is reached. When the carrier hits the stop, the energy from the impact and from the deceleration of the plunger is dissipated through the syringe and the device and can cause breakage of the syringe and/or damage to the device.

Furthermore, whilst some known auto-injector designs include interlock arrangements to guard against accidental operation of the device, in some cases these interlock arrangements can fail to prevent firing of the device upon rough handling or dropping of the device.

Against this background, it would be desirable to provide improved medicament delivery devices that overcome or mitigate some of the above-described problems.

In a first aspect, the present invention resides in a device for delivery of a medicament from a container having an outlet at a distal end of the container and a stopper for containing the medicament in the container, the device comprising a housing, a drive element arranged to move in the distal direction to cooperate with the container, and a drive mechanism comprising a trigger component. The drive mechanism is arranged to hold the drive element in a starting position and to move the drive element in the distal direction from the starting position upon displacement of the trigger component from a working position to a firing position. The device further comprises an interlock component received in the housing and arranged for movement with respect to the housing from a first position to a second position, and at least one flexible locking member arranged to prevent displacement of the trigger component to the firing position when the interlock component is in the first position, wherein movement of the interlock component towards the second position causes bending of the flexible locking member to allow displacement of the trigger component to the firing position.

In this way, the trigger component can be moved to its firing position only when the interlock component has been moved out of its first position, so that accidental or premature operation of the device is avoided. The flexible locking member provides a simple and reliable means for positively blocking movement of the trigger component when the interlock component is in the first position and for subsequently releasing the trigger component.

Preferably, the flexible locking member is arranged to cooperate with a stop face, and movement of the interlock component towards the second position causes bending of the flexible locking member away from the stop face. In this arrangement, displacement of the trigger button can be reliably blocked by engagement between the stop face and the flexible locking member. The stop face may be associated with the housing. For example, the stop face may be disposed on or attached to the housing, or the stop face may be disposed on another component that is not axially movable with respect to the housing at least in an initial state of the device.

The flexible locking member may be arranged to abut the stop face when the interlock component is in the first position. Bending of the flexible locking member upon movement of the interlock component towards the second position may cause the flexible locking member to move clear of the stop face. The stop face may prevent distal movement of the flexible locking member when the interlock component is in the first position.

In an embodiment, the flexible locking member is associated with the trigger component, and the interlock component is arranged to contact the flexible locking member upon movement of the interlock component towards the second position. A proximlal part of the interlock component may contact the flexible locking member upon movement of the interlock component towards the second position.

In another embodiment, the flexible locking member is associated with the interlock component. In this case, the flexible locking member may comprise a blocking face arranged to block distal movement of the trigger component when the flexible locking member abuts the stop face.

The device may comprise a guide formation, which may be associated with the housing, that is arranged to cooperate with the flexible locking member to cause further bending of the locking member upon movement of the trigger component to the firing position.

The firing mechanism may comprise a latching arrangement for latching the plunger in the starting position, and the trigger component may comprise a latch release member for releasing the latching arrangement upon movement of the trigger component to the fired position. The interlock component may cooperate with the latching arrangement to block the release of the latching arrangement when the interlock component is in the first position. The latching arrangement may comprise at least one latching arm associated with the plunger, and the latching arm may be arranged to engage with the housing to latch the plunger in the starting position. The latch release member may be arranged to disengage the latching arm from the housing upon movement of the trigger component to the fired position.

Preferably, the interlock component cooperates with the latching arm to prevent disengagement of the latching arm from the housing when the interlock component is in its first position, and the interlock component moves to release the latching arm upon movement of the interlock component towards its second position. In this way, the interlock component prevents accidental operation of the device in two different ways, firstly by preventing movement of the trigger button to the fired position and secondly by preventing disengagement of the latching arm.

To guard against unintentional movement of the interlock component, the device may comprise a securing mechanism for securing the interlock component in the first position. The securing mechanism may be releasable upon movement of an operating member of the device to allow movement of the interlock component to the second position. Preferably, movement of the operating member causes turning movement of the interlock component relative to the housing thereby to release the securing mechanism. The operating member may comprise a dose selector of the device, and the securing mechanism may release the interlock component when a non-zero dose is selected. In an embodiment, the securing mechanism comprises a securing formation positioned for engagement with a stop formation to prevent movement of the interlock component out of the first position. The securing formation may be movable out of engagement with the stop formation to release the securing mechanism upon movement of the operating member.

Movement of the interlock component towards the second position may cause axial movement of the flexible locking member relative to the housing. The device may include a ramp formation arranged to cooperate with a control formation to bend the flexible locking member upon axial movement of the flexible locking member relative to the housing. Preferably, the ramp formation is disposed on the flexible locking member and the control formation is associated with the housing. The flexible locking member may comprise a guide surface disposed on a distal side of the ramp formation, and the guide surface may be arranged to cooperate with the control formation upon further axial movement of the flexible locking member relative to the housing.

In other embodiments, movement of the interlock component towards the second position causes a radial force to be applied to an end of the flexible locking member to bend the locking member in the radial direction with respect to the housing. In further embodiments, movement of the interlock component towards the second position causes a combination of axial movement and radial bending of the flexible locking member.

In an embodiment, movement of the interlock component towards the second position causes movement of the trigger component relative to the housing from a stowed position to the working position. Advantageously, movement of the trigger component from the stowed position to the working position provides a visual indication to the user that the trigger component has been unlocked and that the device is ready to be activated. The trigger component may be provided at the proximal end of the device and, preferably, the working position is proximal to the stowed position and the trigger position.

The interlock component may be axially movable with respect to the housing, and the second position may be disposed proximally with respect to the first position. A distal part of the interlock component may protrude from a distal end of the housing when the interlock component is in the first position, so that the interlock component can be moved from the first position towards the second position by pressing the distal end of the device against an injection site.

In a second aspect of the invention, there is provided a device for delivery of a medicament from a container having an outlet at a distal end of the container and a stopper for containing the medicament in the container, the device comprising a housing for receiving the container and a drive mechanism arranged to move a drive element in the distal direction with respect to the housing to cooperate with the container upon operation of the drive mechanism. The device further comprises an interlock component received in the housing and arranged for movement with respect to the housing from a first position to a second position to switch the drive mechanism from a locked state to an operating state, and a securing mechanism for securing the interlock component in the first position. The securing mechanism is releasable upon movement of an operating member of the device to allow movement of the interlock component to the second position. By securing the interlock component in the first position, the risk of unintentional movement of the interlock out of the first position, for example if the device were to be dropped, is reduced.

Preferably, movement of the operating member causes turning movement of the interlock component relative to the housing thereby to release the securing mechanism. The operating member may comprise a dose selector of the device, and the securing mechanism may release the interlock component when a non-zero dose is selected. In this way, the device cannot be operated until a dose has been selected. The securing mechanism may comprise a securing formation positioned for engagement with a stop formation to prevent movement of the interlock component out of the first position. The securing formation may be movable out of engagement with the stop formation to release the securing mechanism upon movement of the operating member.

According to a third aspect of the present invention, there is provided an injection device for injection of a medicament from a container through a needle disposed at the distal end of the container, the container having a container body and a stopper for containing the medicament in the container body. The device comprises a housing, a plunger for driving the stopper of the container in a distal direction to expel the medicament through the needle, a drive mechanism arranged to apply an insertion force to the container upon activation of the drive mechanism, thereby to move the container relative to the housing from a starting position in which the needle is shrouded to an insertion position in which the needle is exposed, and a carrier for receiving the container body, the carrier comprising a retardation element arranged to contact the container body. Upon activation of the drive mechanism, the container moves in the distal direction with respect to the carrier, and the retardation element is arranged to apply a frictional retardation force to the container body to retard movement of the container against the influence of the insertion force.

In this way, the velocity of the container can be limited during relative movement between the container and the carrier, thereby reducing the impact loads and other stresses experienced by the container and the device compared with prior art devices in which the carrier and the container move together. The frictional retardation force may retard movement of the container by reducing the acceleration of the container. For example, the frictional retardation force may decelerate the container.

The retardation element may comprise a bore for receiving the container body. To enhance the frictional retardation force, an internal surface of the bore may comprise at least one deformable projection arranged to press against the container body. For example, the or each deformable projection may comprise an annular rib. In another example, the or each deformable projection is wedge-shaped. The or each projection may be integrally formed with the retardation element.

The retardation element is preferably elastomeric. For example, the retardation element may be of a thermoplastic elastomer material. The carrier may comprise a carrier support for supporting the retardation element.

The movement of the container relative to the housing from the starting position to the insertion position may define an insertion stroke of the container. In the starting position of the container, the needle may be retracted in the housing, and in the insertion position, the needle may project from the distal end of the housing. The device is preferably arranged such that the container moves in the distal direction with respect to the carrier over a final part of the insertion stroke. The frictional retardation force may act to reduce the acceleration of the container during the final part of the insertion stroke. For example, the frictional retardation force may decelerate the container during the final part of the insertion stroke. In this way, the velocity of the container is relatively high during an initial part of the insertion stroke, to facilitate insertion of the needle through the skin, and then the velocity of the container is reduced to reduce impact loads as the container reaches the insertion position.

In one embodiment, the carrier is arranged to move axially with the container to a stop position of the carrier and to remain fixed with respect to the housing at the stop position over the final part of the insertion stroke. For example, the carrier may be arranged to contact a stop of the housing to define the stop position. The carrier is preferably guided for axial movement within the housing.

The carrier may be arranged to contact a locating flange of the container body at the end of the insertion stroke. For example, the container may be a pre-filled syringe, and the locating flange may be a finger flange disposed at the proximal end of the syringe body or barrel.

The carrier may comprise a damping element arranged to contact the locating flange at the end of the insertion stroke. The damping element may be resiliently deformable upon contact between the locating flange and the carrier. In this way, the damping element may assist in dissipating impact energy when the container hits the carrier.

The device may comprise a latch member for blocking proximal movement of the carrier with respect to the housing once the carrier has moved to the stop position. Advantageously, the latch member helps to prevent the container body moving in the proximal direction with respect to the stopper at the end of an injection, which might otherwise result in more medicament being delivered than intended. This is particularly useful in selectable-dose injection devices, in which some medicament remains in the container at the end of injection. The latch member may be arranged to cooperate with a stop. In one example, the latch member comprises a ramped face for deflecting the latch member to pass the stop upon distal movement of the carrier, and a blocking face for abutment with the stop to block subsequent proximal movement of the carrier. The latch member may be provided on the carrier and the stop may be provided on the housing.

The carrier may be disposed in an initial axial position relative to the housing before activation of the drive mechanism. Preferably, the carrier is lockable in the initial axial position. In this way, undesired movement of the carrier and the container with respect to the housing before operation of the device can be avoided.

To this end, the device may further comprise an interlock component received in the housing and arranged for movement with respect to the housing from a first position to a second position, and a carrier lock arrangement arranged to cooperate with the interlock component to lock the carrier in the initial axial position when the interlock component is in the first position, and to release the carrier upon movement of the interlock component towards the second position. The interlock component may be arranged concentrically around the carrier. The interlock component may be arranged for axial movement with respect to the housing. In the first position, a distal part of the interlock component may protrude from a distal end of the housing. The second position may be disposed proximally with respect to the first position.

In one example, the carrier lock arrangement comprises at least one beam element arranged to engage with a locking formation and to disengage from the locking formation upon deflection of the beam element, and the interlock component is arranged to brace the beam element against deflection when the interlock component is in the first position and to release the beam element for deflection when the interlock component moves towards the second position. The device may comprise a bracing formation for bracing the beam element. For example, the bracing formation may comprise a tab. The interlock component may comprise the bracing formation. The bracing formation may bear against a rail of the beam element. To brace the beam element, the interlock component may for example bear against an inner surface of the beam element, or against a side of the beam element. Preferably, the bracing formation moves into a clearance when the interlock component moves towards the second position to release the beam element for deflection. The beam element may be provided on the carrier, and the locking formation may be provided on the housing. In an embodiment, the carrier comprises a plurality of angularly-spaced beam elements, and the interlock component is arranged to bridge between adjacent beam elements to brace the beam elements against deflection.

The beam element may comprise a projection for cooperation with the locking formation. The projection may be arranged to cause deflection of the beam element upon distal movement of the carrier relative to the locking formation. For example, the projection may cooperate with an edge of the locking formation.

The device may comprise a securing mechanism for securing the interlock component in the first position. The securing mechanism may be releasable upon movement of an operating member of the device, to allow movement of the interlock component to the second position. By securing the interlock component in the first position in this way, the risk of accidental activation of the device, for example due to dropping of the device, can be reduced.

The injection device may further comprise a priming mechanism having an operating member which is movable with respect to the housing. The priming mechanism may be arranged to move the container body in the proximal direction with respect to the carrier upon movement of the operating member from a first position to a second position. Advantageously, the priming mechanism can be arranged to move the container body to the starting position before activation of the drive mechanism. In particular, when the container body comprises a locating flange, the priming mechanism can be used to ensure that there is a clearance between the locating flange and the carrier at the start of the insertion stroke, so that the container body can move distally with respect to the carrier during the insertion stroke.

The device may comprise blocking means arranged to prevent movement of the carrier in the proximal direction during proximal movement of the container body by the priming mechanism. For example, the blocking means may be a blocking projection on the carrier.

The device may comprise at least one holding member for preventing movement of a needle shield of the container in the proximal direction when the operating member is moved from the first position to the second position. In this way, operation of the priming mechanism can also deshield the needle.

The priming mechanism may comprise a carrier part arranged to cooperate with a shoulder of the container body when the operating member is moved from the first position to the second position.

Movement of the operating member from the first position to the second position may comprise a turning movement. The priming mechanism may comprise a shuttle member arranged to cooperate with the operating member and the container body. The shuttle member may comprise the carrier part. Preferably, the device comprises a cam element arranged to cooperate with the shuttle member to move the shuttle member in the proximal direction upon movement of the operating member from the first position to the second position. For example, the cam element may comprise a ramp formation for cooperation with a follower of the shuttle member.

Movement of the operating member from the first position to the second position may cause relative turning movement between the shuttle member and the cam element. The shuttle member may be coupled to a shuttle guide, such that relative turning movement of the shuttle member with respect to the shuttle guide is prevented. Conveniently, when an interlock component is present, the shuttle guide may comprise the interlock component.

The shuttle guide may be coupled to the operating member such that movement of the operating member from the first position to the second position causes turning movement of the shuttle member relative to the cam element. For example, the operating member may comprise a dose selector of the device.

When a dose selector is provided, the device may comprise a plurality of stop formations associated with the housing and disposed at different axial positions relative to the distal end of the housing, and a plunger guide formation associated with the plunger for cooperation with a selected one of the stop formations to limit the distal movement of the plunger. The dose selector may be coupled to the plunger to turn the plunger relative to the housing to align the plunger guide formation with the selected stop formation.

In another example, the cam element may be coupled to the operating member such that movement of the operating member from the first position to the second position causes turning movement of the cam element relative to the shuttle member. For example, the operating member may comprise a removable cap for closing a distal end of the housing. When the cap is in the first position, the cap may be locked against removal from the housing and, when the cap is in the second position, the cap may be unlocked for removal from the housing.

In one embodiment, the device comprises a first operating member and a second operating member. Each operating member may be movable with respect to the housing between respective first and second positions, and the priming mechanism may be arranged to move the container body in the proximal direction with respect to the carrier upon movement of the first or the second operating member from its respective first position to its respective second position while the other operating member is in a fixed position relative to the housing. The first operating member may comprise a removable cap for closing a distal end of the housing and the second operating member may comprise a dose selector. In this example, the priming mechanism can be operated either by removal of the cap or by selection of a dose.

The priming mechanism may be arranged to push the stopper of the container against a priming member upon movement of the operating member from the first position to the second position. In this way, the stopper of the container can be moved to a known primed position prior to medicament delivery, to avoid inaccuracy in the delivered dose due to variations in the initial position of the stopper after filling of the container with medicament.

The priming member may comprise the plunger. Alternatively, the priming member may be a separate component, and the plunger may be movable with respect to the priming member. For example, the plunger may comprise a bore, and the priming member may comprise a rod received in the bore. The priming member may be attached to the housing, and may be detachable from the housing upon movement of the plunger in the distal direction.

The injection device may comprise clamping means arranged to apply a clamping force to the retardation element to press the retardation element against the container body, thereby to restrict axial movement of the container body with respect to the carrier. Advantageously, the clamping means prevents movement of the container body before activation of the device, allowing the container to be set in the starting position with respect to the carrier during assembly of the device.

The device may include a removable deshielder, such as a cap, that is arranged to apply a deshielding force to a needle shield of the container for removal of the needle shield from the container. In this case, the clamping force applied by the clamping means may prevent axial movement of the container body with respect to the carrier upon application of the deshielding force.

The clamping means may be switchable between a clamped state in which the clamping force is applied, and a released state in which the clamping force is removed. The clamping means may comprise a clamping member attached to the carrier.

The clamping member may comprise a fixed part attached to the carrier and a free part, and the free part may be movable with respect to the fixed part to apply the clamping force to the retardation element when the clamping means is in the clamped state. The free part of the clamping member may be disposed distally with respect to the fixed part. When the retardation element includes a deformable projection arranged to press against the container body, the deformable projection may be adjacent to the free part of the clamping member.

The device may include a control element arranged to engage with a control surface of the clamping member when the clamping means is in the clamped state. The control element may be movable with respect to the carrier to disengage from the control surface to switch the clamping means to the released state. The control element is preferably movable to a clearance to disengage from the control surface. In one example, the clearance is defined by a recess in the carrier and/or the clamping member.

When an interlock component is provided, the interlock component preferably comprises the control element, such that movement of the interlock component from the first position towards the second position switches the clamping means from the clamped state to the released state. The control element may, for example, comprise a rib of the interlock component. In this way, the interlock component may simultaneously switch the clamping means and release the carrier lock arrangement to prepare the device for operation.

Conveniently, the insertion force may be applied to the container by the plunger. The drive mechanism may be arranged to hold the plunger in a starting position and to move the plunger in the distal direction from the starting position upon activation of the drive mechanism.

The drive mechanism may comprise a trigger component. The trigger component may be movable from a working position to a firing position to activate the drive mechanism. When the device includes an interlock component, the interlock component preferably cooperates with the trigger component to prevent movement of the trigger component to the firing position when the interlock component is in its first position and to allow movement of the trigger component to the firing position when the interlock component is in its second position. In this way, the interlock component may simultaneously unlock the trigger component, release a carrier lock arrangement and/or switch a clamping means of the device.

In one example, the device includes at least one flexible locking member arranged to prevent displacement of the trigger component to the firing position when the interlock component is in the first position. Movement of the interlock component towards the second position may cause bending of the flexible locking member to allow displacement of the trigger component to the firing position.

The device of the third aspect of the invention may be a device according to the first or the second aspect of the invention.

From a fourth aspect of the present invention, there is provided an injection device for injection of a medicament from a container through a needle disposed at the distal end of the container, the container having a container body and a stopper for containing the medicament in the container body, and the device comprising a housing, a plunger for driving the stopper of the container in a distal direction to expel the medicament through the needle, a drive mechanism arranged to move the container relative to the housing from a starting position in which the needle is retracted in the housing to an insertion position in which the needle projects from the distal end of the housing, and a carrier for receiving the container body. The carrier is guided for axial movement with respect to the housing. The device further comprises an interlock component arranged for movement from a first position to a second position, and a carrier lock arrangement arranged to lock the carrier in an initial axial position relative to the housing when the interlock component is in the first position, and to release the carrier from the initial axial position upon movement of the interlock component towards the second position.

In this way, when the interlock component is in the initial state, movement of the carrier with respect to the housing is prevented, which stops the carrier and the container from moving within the housing during transport of the device. To this end, the carrier lock arrangement can prevent movement of the carrier from the initial axial position in both the distal and proximal directions. Furthermore, if the container is fitted with a needle shield, a force can be applied to remove the needle shield without movement of the carrier or the container.

The carrier may be arranged for joint axial movement with the container from the initial axial position of the carrier to a stop position of the carrier. In this case, the device may comprise a latching arrangement for blocking proximal movement of the carrier with respect to the housing once the carrier has moved to the stop position. During assembly of the device, the carrier lock arrangement can prevent movement of the carrier during insertion of the container into the carrier, thus preventing premature latching of the carrier in the stop position. The latching arrangement may comprise a latch member arranged to cooperate with a stop. The or each beam element may be provided on the carrier.

In one example, the carrier lock arrangement comprises a beam element arranged to engage with a locking formation and to disengage from the locking formation upon deflection of the beam element, and the interlock component is arranged to brace the beam element against deflection when the interlock component is in the first position and to release the beam element for deflection when the interlock component moves towards the second position. The interlock component may for example bear against a side of the beam element, or against an inner surface of the beam element to brace the beam element. A bracing formation may be provided for bracing the beam element. The bracing formation may move into a clearance when the interlock component moves towards the second position to release the beam element for deflection. The interlock component may comprise the bracing formation, in which case the clearance may be provided by a recess in the beam element.

The carrier may comprise a plurality of angularly spaced beam elements, and the interlock component may be arranged to bridge between adjacent beam elements to brace the beam elements against deflection.

When the or each beam element is provided on the carrier, the locking formation may be provided on the housing. The beam element may comprise a projection for cooperation with the locking formation, and the projection may be arranged to cause deflection of the beam element upon distal movement of the carrier relative to the locking formation.

In one embodiment, when the interlock component is in the first position, a distal part of the interlock component protrudes from a distal end of the housing, and the second position is disposed proximally with respect to the first position. In this way, the interlock component can be moved towards the second position by placing the distal end of the device against an injection site.

The carrier may be arranged to couple with a locating flange of the container body. The carrier may comprise a frictional element arranged to contact the container body. Upon activation of the drive mechanism, the container may move in the distal direction with respect to the carrier during a final part of an insertion stroke of the container, and the frictional element may comprise a retardation element arranged to apply a frictional retardation force to the container body to retard movement of the container relative to the carrier.

When a frictional element is provided, the device may include clamping means arranged to apply a clamping force to the frictional element to press the frictional element against the container body, thereby to restrict axial movement of the container body with respect to the carrier. The clamping means may comprise a clamping member switchable between a clamped state in which the clamping force is applied, and a released state in which the clamping force is removed. The interlock component may comprise a control element arranged to engage with a control surface of the clamping member when the interlock component is in the first position to hold the clamping means in the clamped state, and the control element may be arranged to disengage from the control surface when the interlock component is moved to the second position to switch the clamping means to the released state.

The device of the fourth aspect of the invention may also be in accordance with the first, second and/or third aspects of the invention.

Aspects and embodiments of the present invention may be used for the delivery of medicaments comprising or including pharmaceutical products (active ingredients).

Pharmaceutical products (active ingredients) contemplated for use include small molecules, vaccines, live or attenuated cells, oligonucleotides, DNA, peptides, antibodies, and recombinant or naturally occurring proteins, whether human or animal, useful for prophylactic, therapeutic or diagnostic application. The active ingredient can be natural, synthetic, semi-synthetic or derivatives thereof. In addition, active ingredients of the present invention can be perceptible. A wide range of active ingredients are contemplated. These include but are not limited to hormones, cytokines, hematopoietic factors, growth factors, antiobesity factors, trophic factors, anti-inflammatory factors, and enzymes. One skilled in the art will readily be able to adapt a desired active ingredient to the necessary formulations encompassed by the present invention.

Active ingredients can include but are not limited to insulin, gastrin, prolactin, human growth hormone (hGH), adrenocorticotropic hormone (ACTH), thyroid stimulating hormone (TSH), luteinizing hormone (LH), follicle stimulating hormone (FSH), human parathyroid hormone (PTH), glucagon, glucagons-like peptide 1 (GLP-1), glucagons-like peptide 2 (GLP-2), insulin-like growth factors (IGFs) such as insulin growth factor I (IGF I), insulin growth factor II (IGF II), growth hormone-releasing factor (GRF), human chorionic gonadotropin (HCG), gonadotropin-releasing hormone, motilin, interferons (alpha, beta, gamma), interleukins (e.g., IL-1, IL-2, IL-4, IL-5, IL-6, IL-9, IL-11, IL-12, IL-13, IL-15, IL-16, IL-17, IL-18, IL-20 or IL-21), interleukin-1 receptor antagonists (IL-Ira), tumor necrosis factor (TNF), tumor necrosis factor-binding protein (TNF-bp), CD40L, CD30L, erythropoietin (EPO), plasminogen activator inhibitor 1, plasminogen activator inhibitor 2, von Willebrandt factor, thrombopoietin, angiopoietin, granulocyte-colony stimulating factor (G-CSF), stem cell factor (SCF), leptin (OB protein), brain derived neurotrophic factor (BDNF), glial derived neurotrophic factor (GDNF), neurotrophic factor 3 (NT3), fibroblast growth factors (FGF), neurotrophic growth factor (NGF), bone growth factors such as osteoprotegerin (OPG), transforming growth factors, epidermal growth factor (EGF), vascular endothelial growth factor (VEGF), macrophage colony stimulating factor (M-CSF), granulocyte macrophage colony stimulating factor (GM-CSF), megakaryocyte derived growth factor (MGDF), keratinocyte growth factor (KGF), platelet-derived growth factor (PGDF), novel erythropoiesis stimulating protein (NESP), bone morphogenetic protein (BMP), superoxide dismutase (SOD), tissue plasminogen activator (TPA), pro-urokinase, urokinase, streptokinase, kallikrein, a protease inhibitor e.g. aprotinin, an enzyme such as asparaginase, arginase, arginine deaminase, adenosine deaminase, ribonuclease, catalase, uricase, bilirubin oxidase, trypsin, papain, alkaline phosphatase, glucoronidase, purine nucleoside phosphorylase or batroxobin, an opioid, e.g. endorphins, enkephalins or non-natural opioids, a neuropeptide, neuropeptide Y, calcitonin, cholecystokinins, corticotrophin-releasing factor, vasopressin, oxytocin, antidiuretic hormones, thyrotropin releasing hormone, relaxin, peptideYY, pancreastic polypeptide, CART (cocaine and amphetamine regulated transcript), a CART related peptide, perilipin, melanocortins (melanocyte-stimulating hormones) such as MSH, melanin-concentrating hormones, natriuretic peptides, adrenomedullin, endothelin, secretin, amylin, vasoactive intestinal peptide (VIP), pituary adenylate cyclase activating polypeptide (PACAP), bombesin, bombesin-like peptides, thymosin, heparin-binding protein, soluble CD4, hypothalmic releasing factor, melanotonins, and human antibodies and humanized antibodies. The term proteins, as used herein, includes peptides, polypeptides, consensus molecules, analogs, derivatives or combinations thereof.

Active ingredients include any extended half-life variants of the active ingredient listed herein or analogues thereof. Thus, the active ingredients can be any long acting variants of the active ingredient listed herein or analogues thereof. In some embodiments, the active ingredient include any extended half-life or long acting variants of hGH, insulin, glucagon, glucagons-like peptide 1 (GLP-1), glucagons-like peptide 2 (GLP-2), insulin-like growth factors (IGFs). In some embodiments, the active ingredient is an extended half-life or long acting variant of hGH. Examples of extended half-life or long acting variants of hGH include, but are not limited to LB03002, NNC126-0883, NNC0195-0092, MOD-4023, ACP-001, Albutropin, somavaratan (VRS-317), and profuse GH.

Preferred and/or optional features of each aspect of the invention may be used, alone or in appropriate combination, in the other aspects of the invention also.

Embodiments of the present invention will now be described, by way of example only, with reference to the accompanying drawings in which like reference numerals are used for like features, and in which:

FIGS. 1(a) and 1(b) are front and side views, respectively, of an injection device according to the present invention;

FIG. 2 is an isometric view of the injection device of FIG. 1;

Figure 4A:
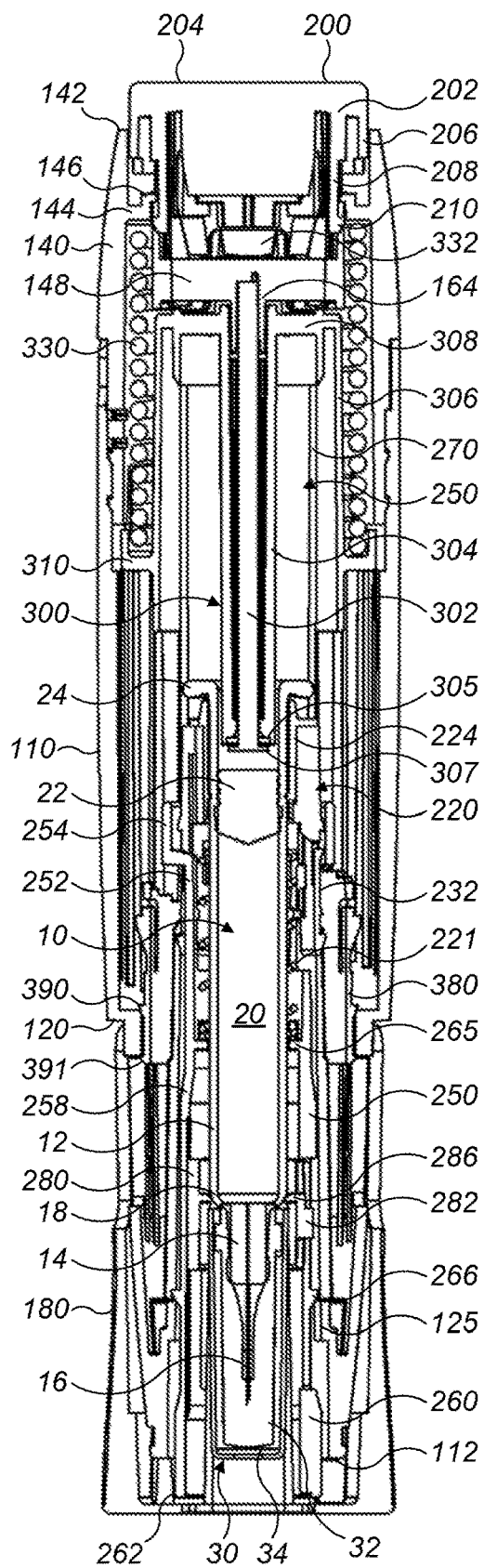
Figure 4B:
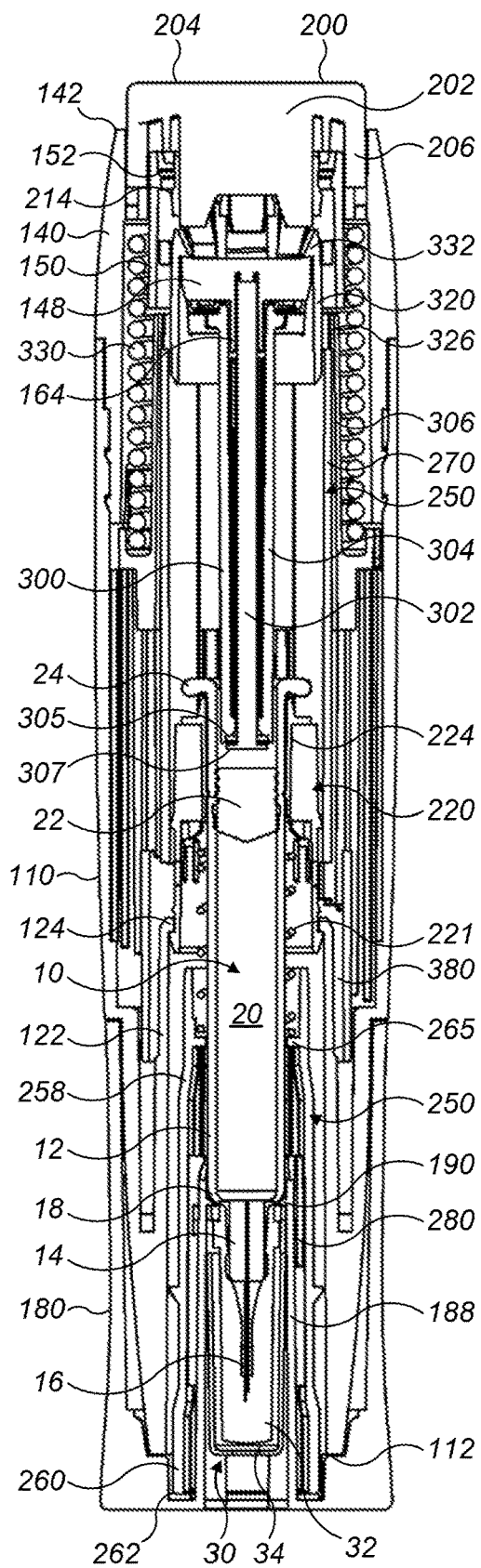
Figure 5A:
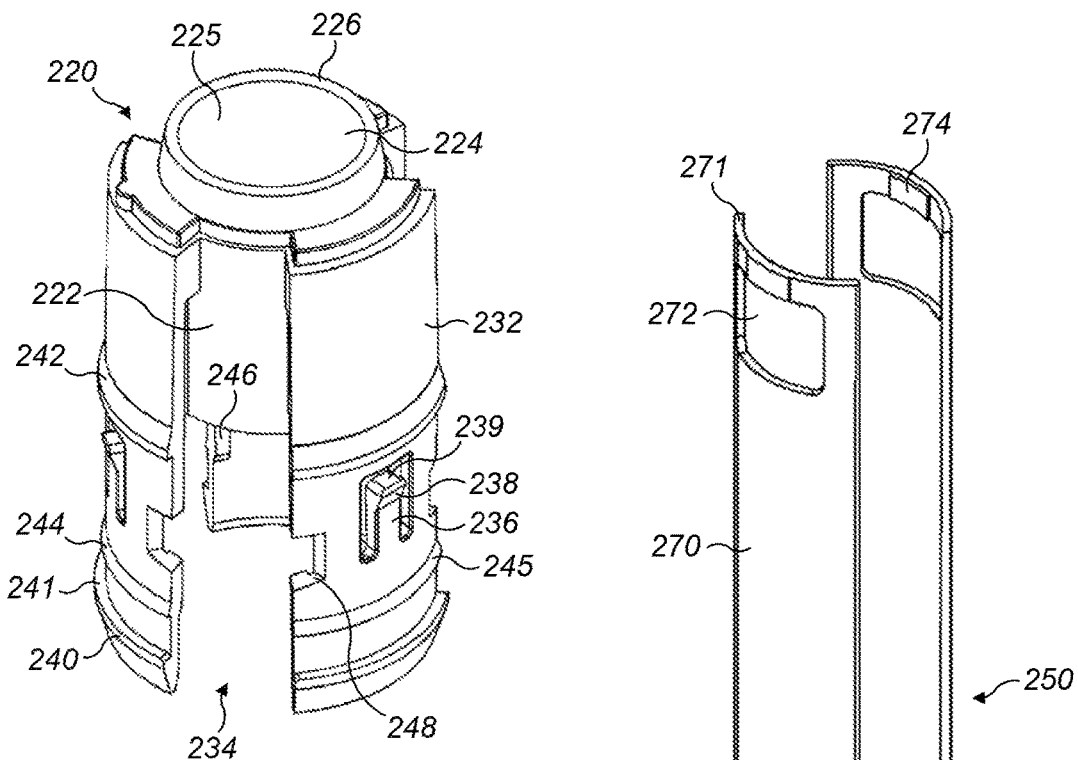
Figure 5B:
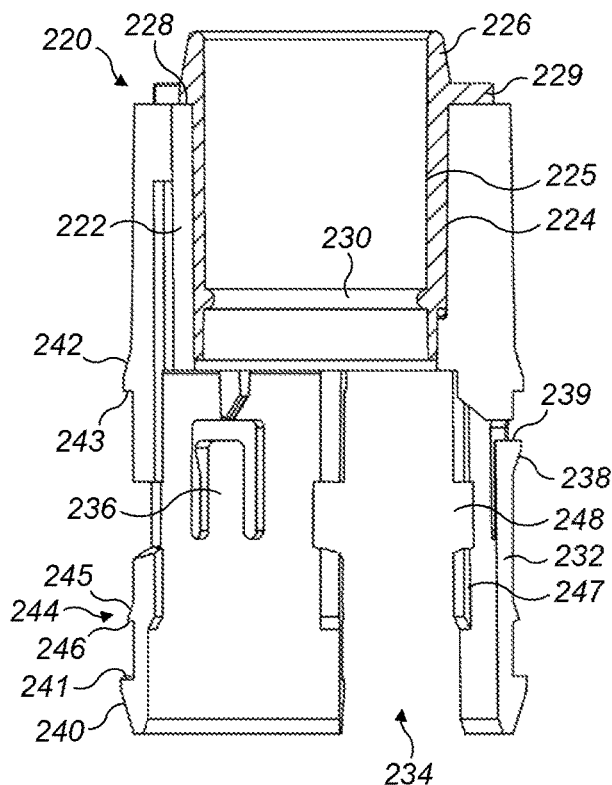
Figure 6:
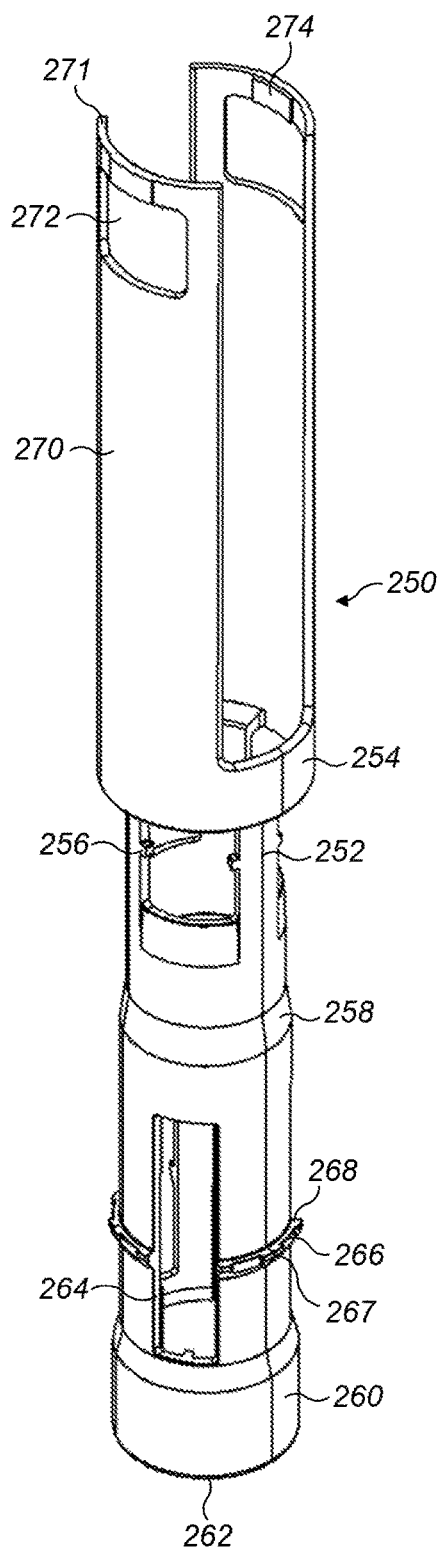
Figure 7:
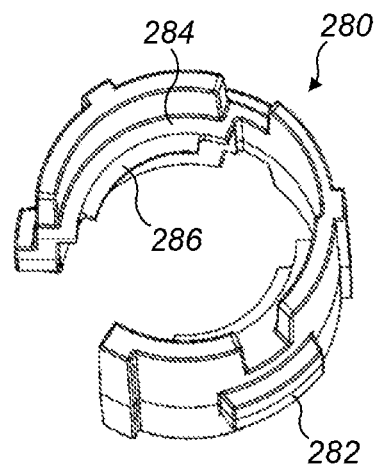
Figure 8:
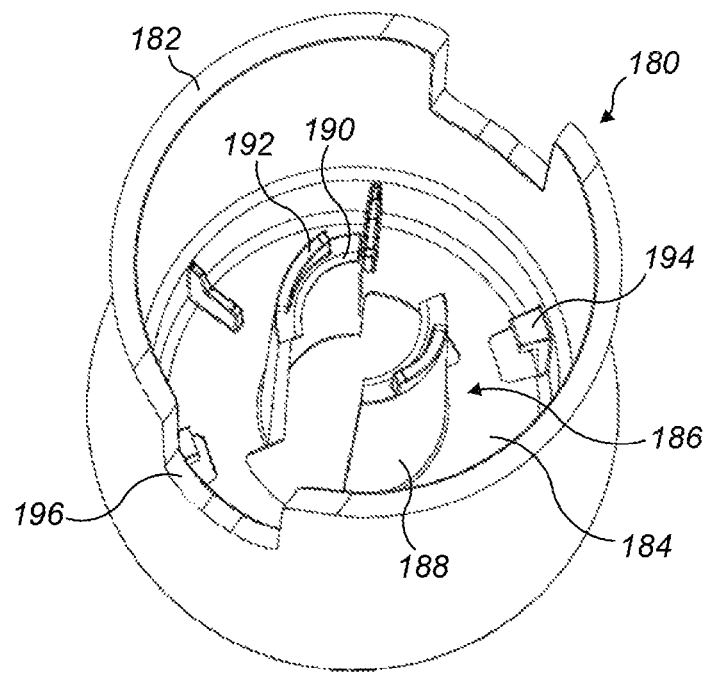
Figure 9A:
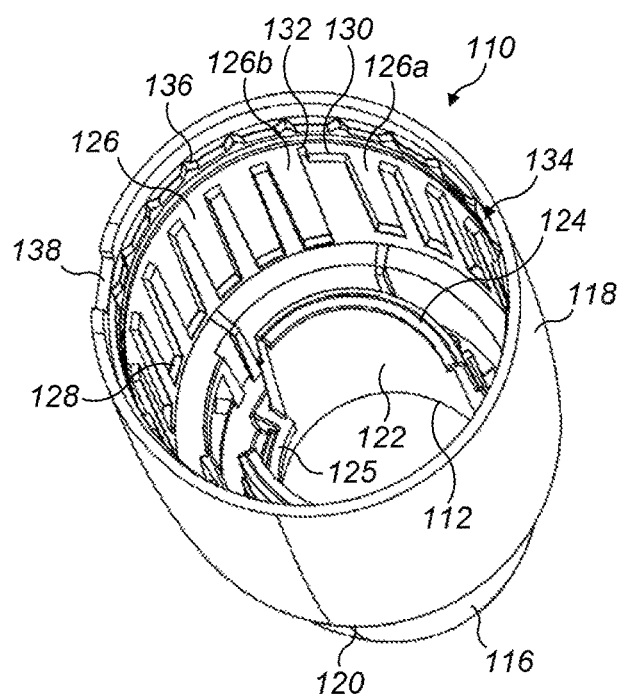
Figure 9B:
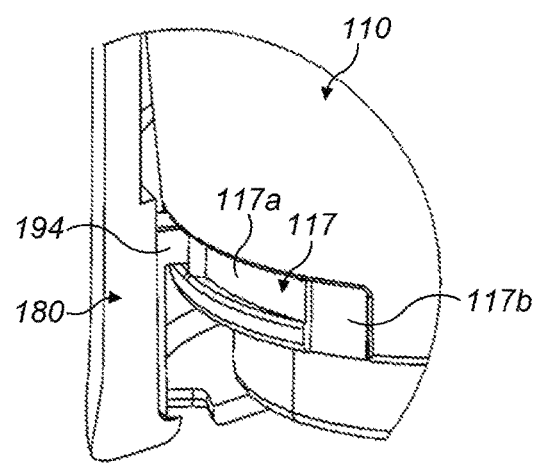
Figure 10:
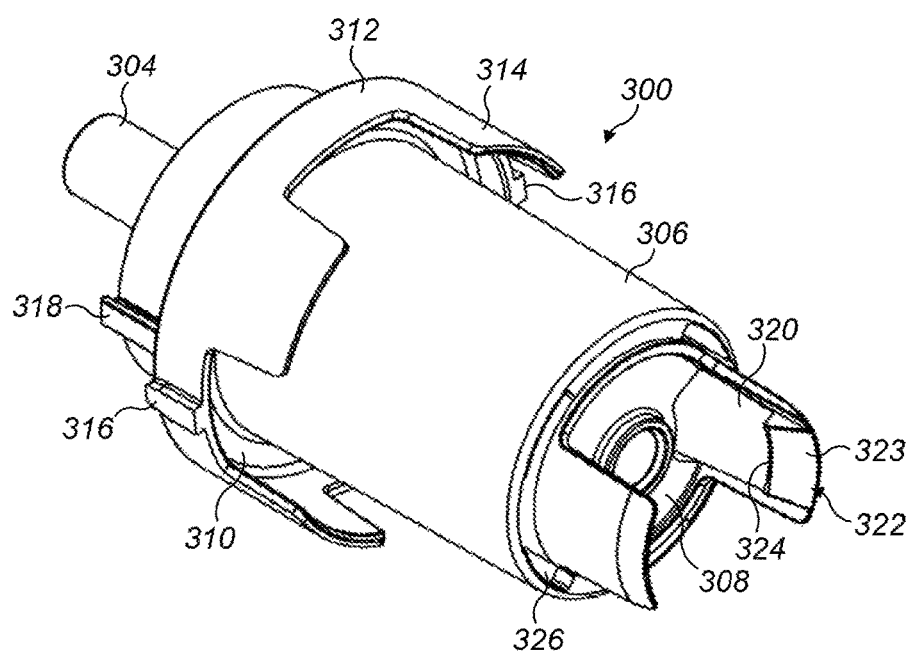
Figure 11:
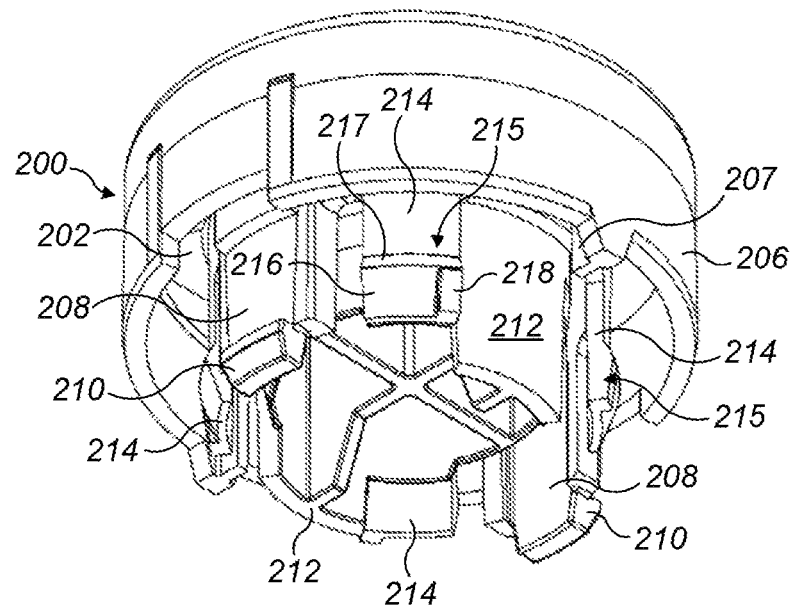
Figure 12:
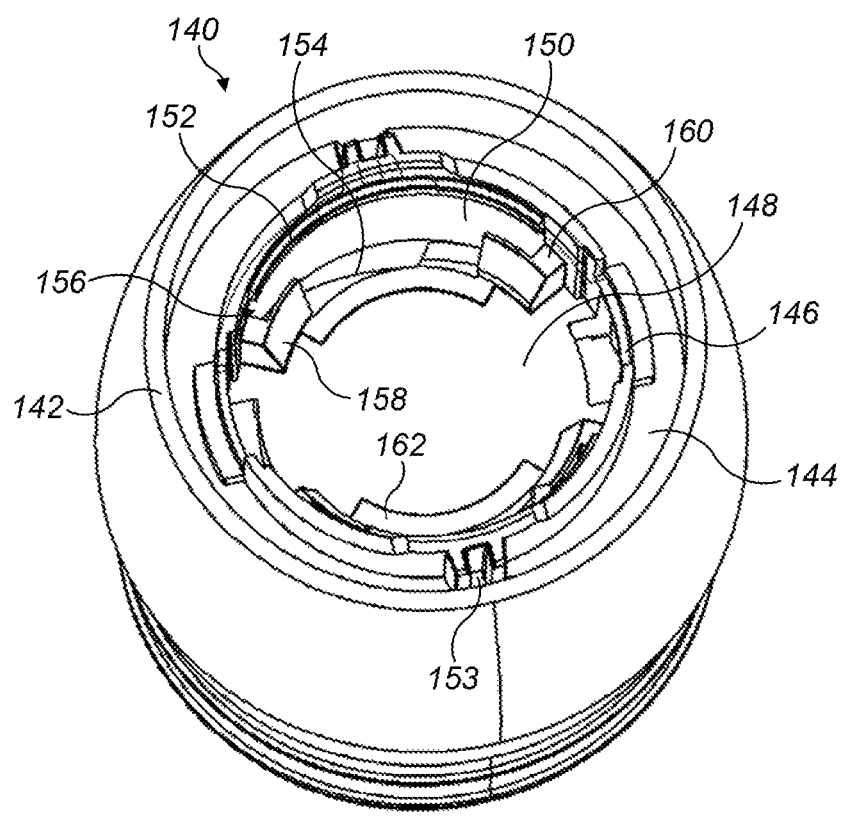
Figure 13:
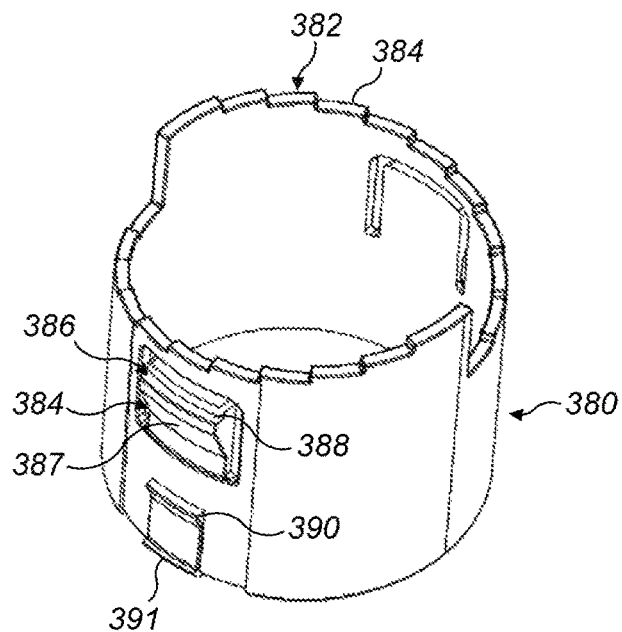
Figure 14:
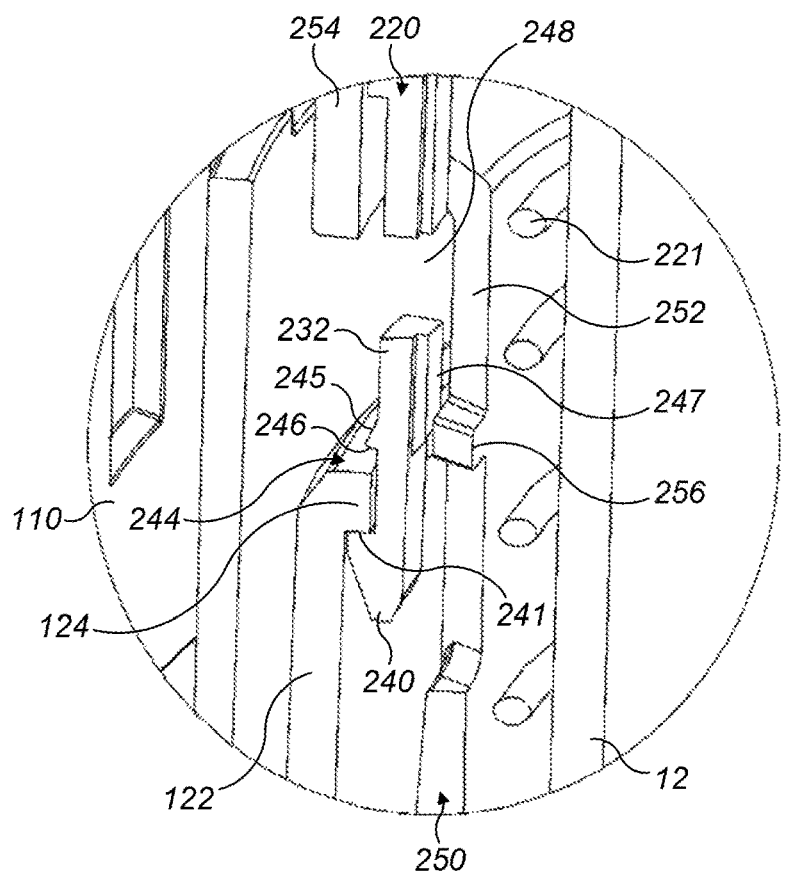
Figure 15:
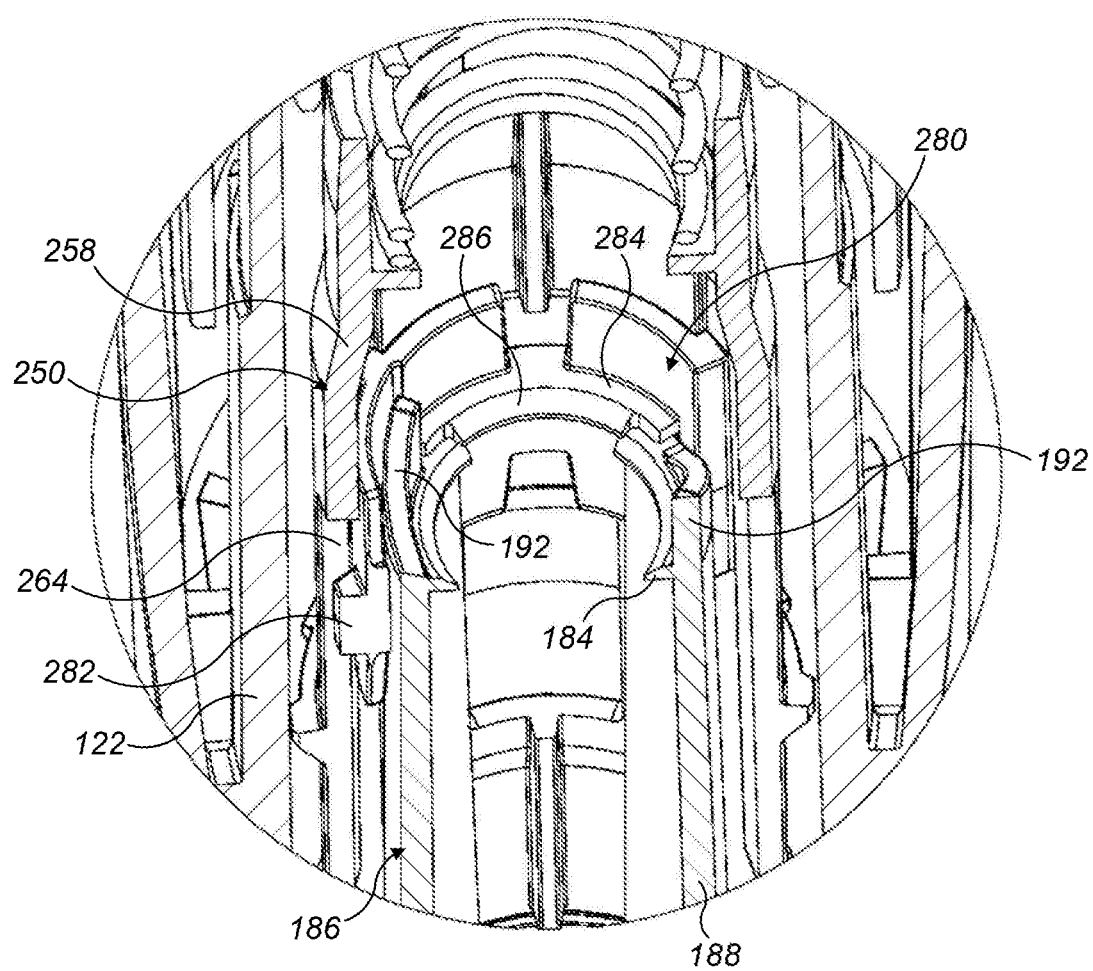
Figure 16B:
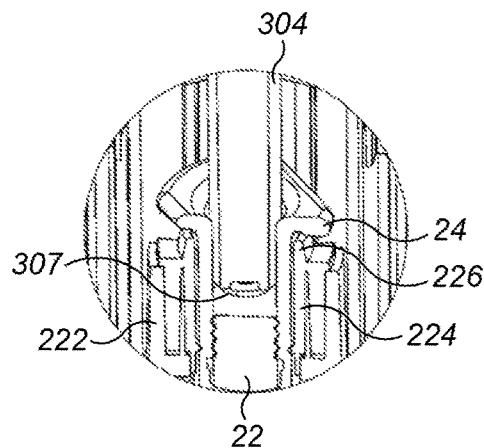
Figure 17B:
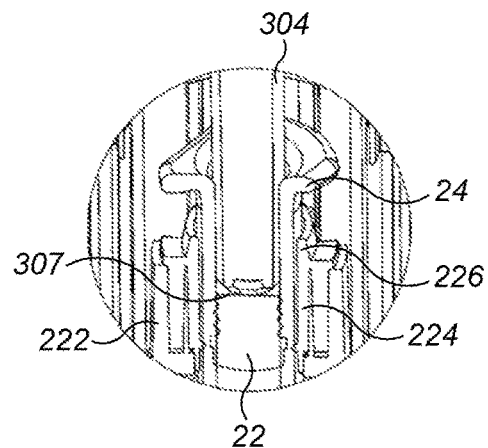
Figure 16A:
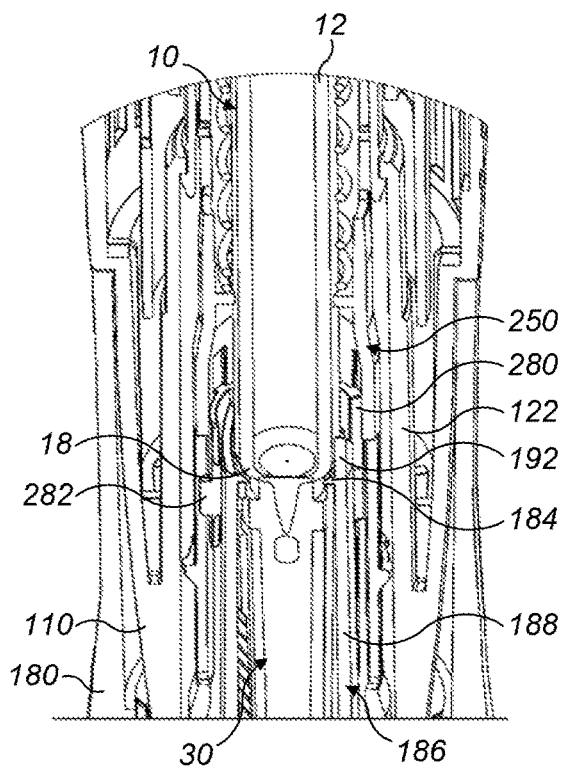
Figure 17A:
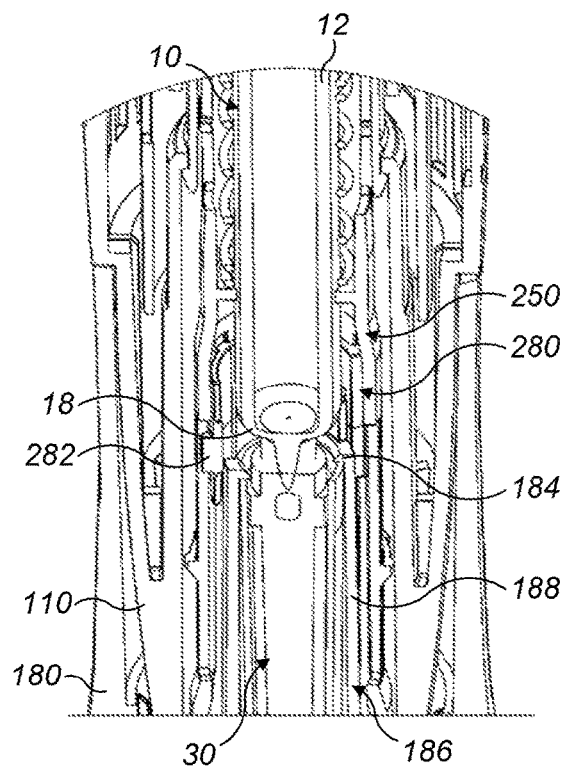
Figure 18A:
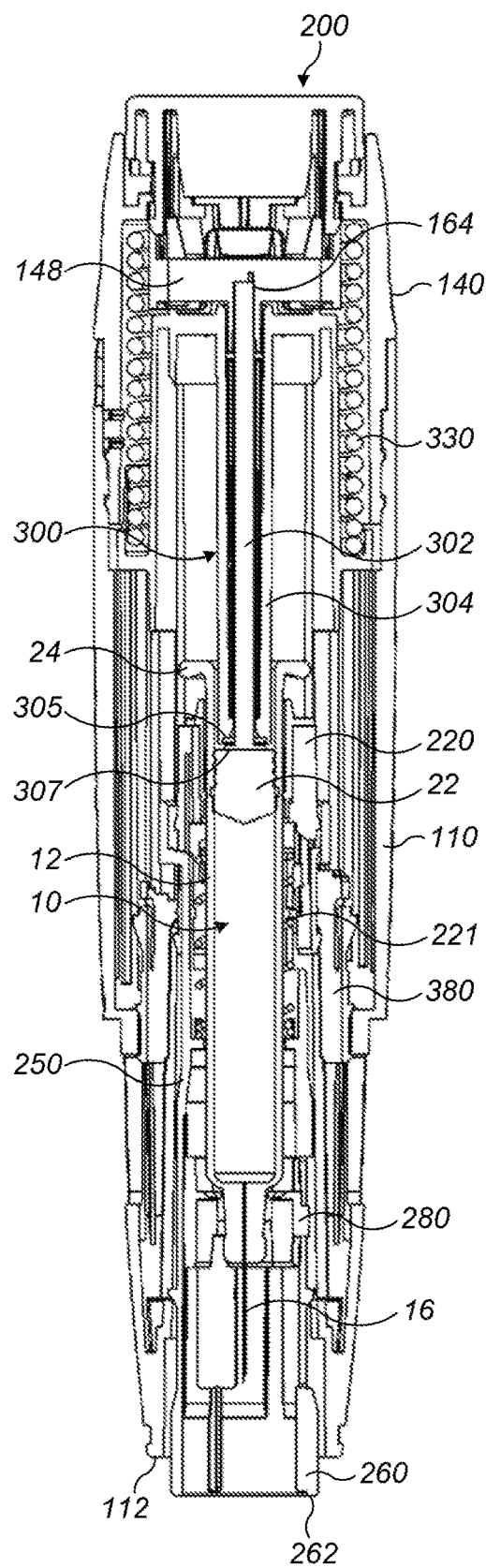
Figure 18B:
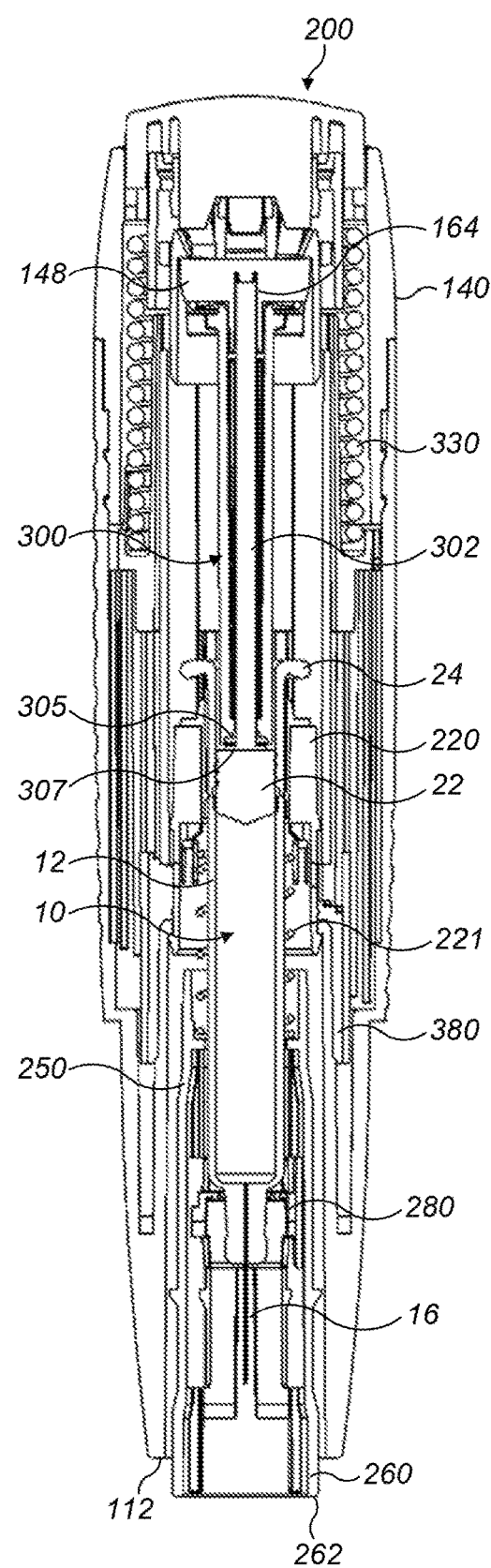
Figure 19B:
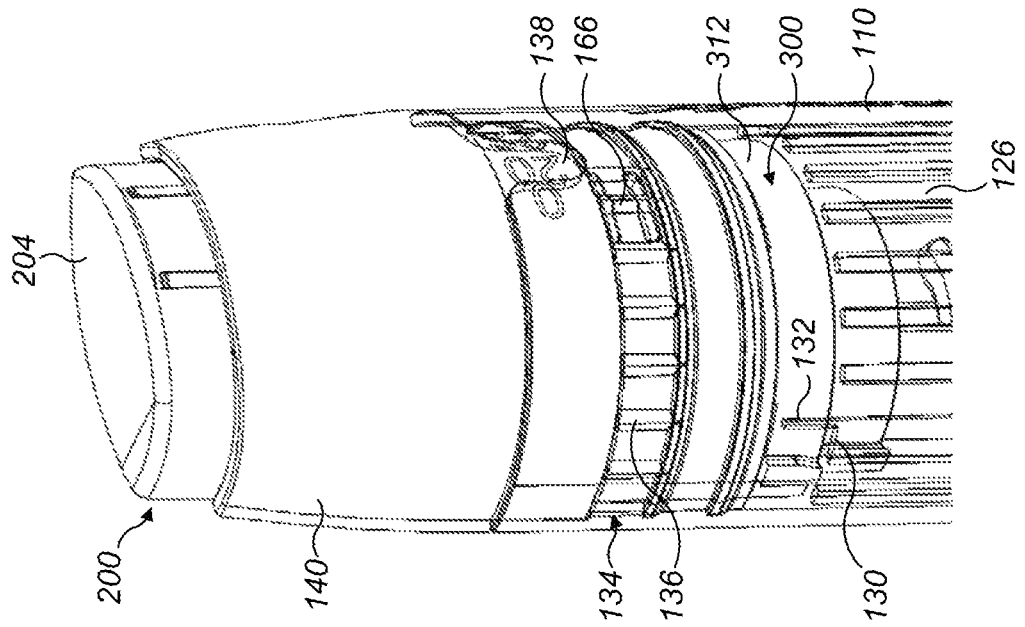
Figure 19A:
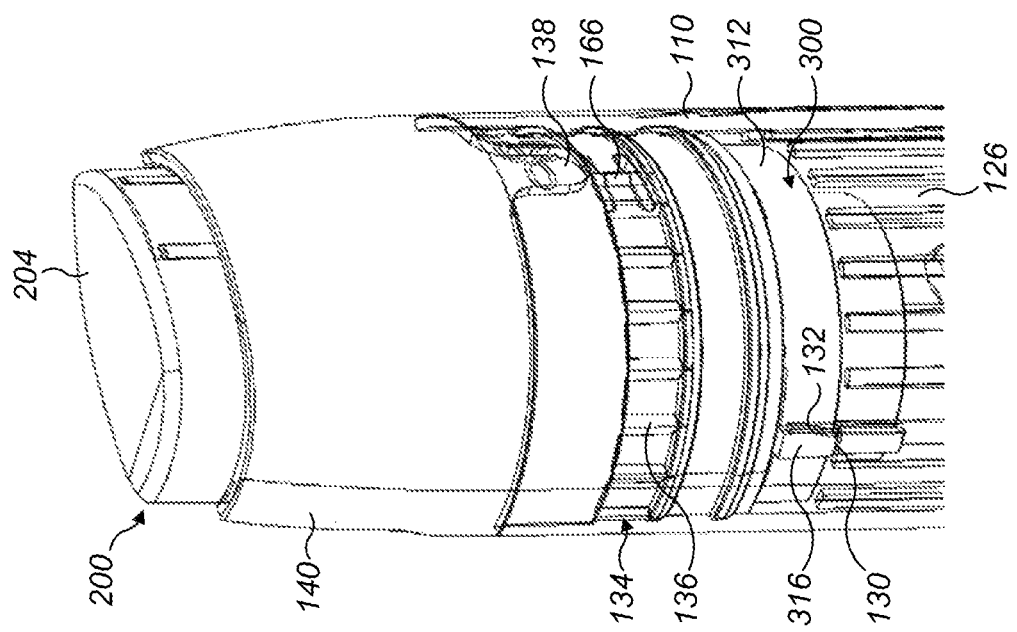
Figure 21A:
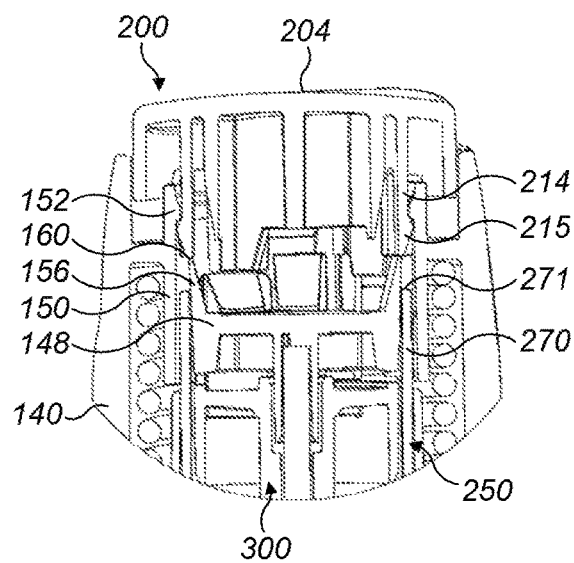
Figure 21B:
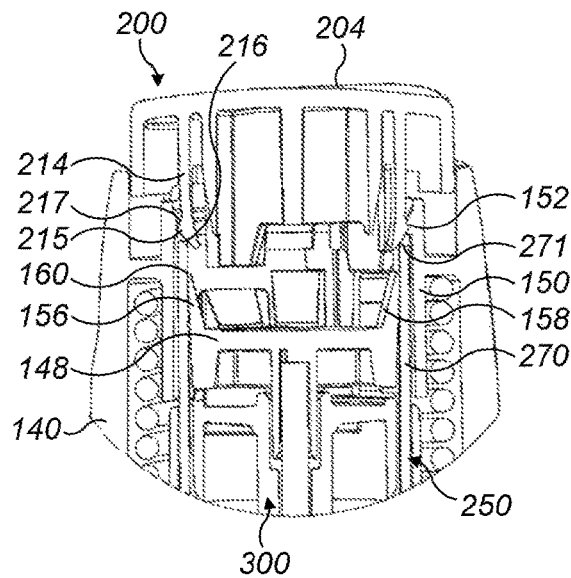
Figure 22A:
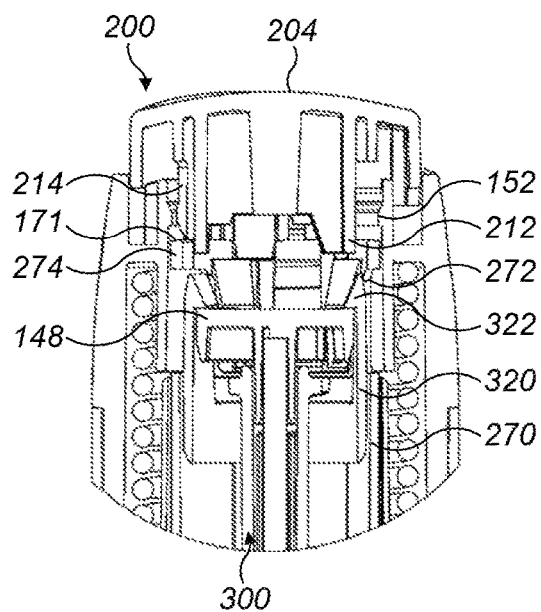
Figure 22B:
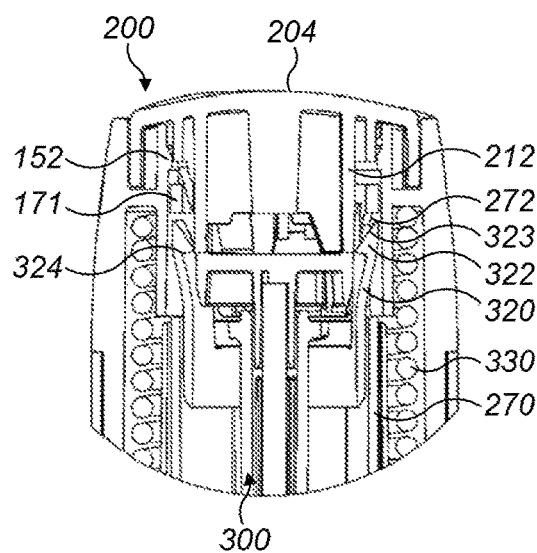
Figure 23A:
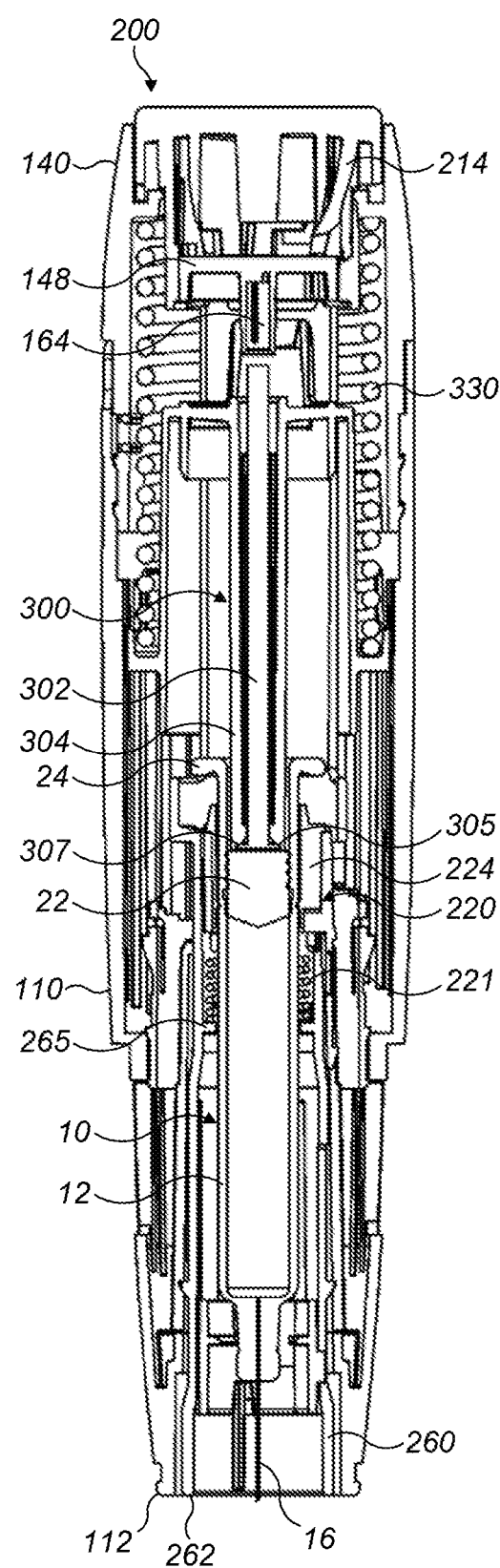
Figure 23B:
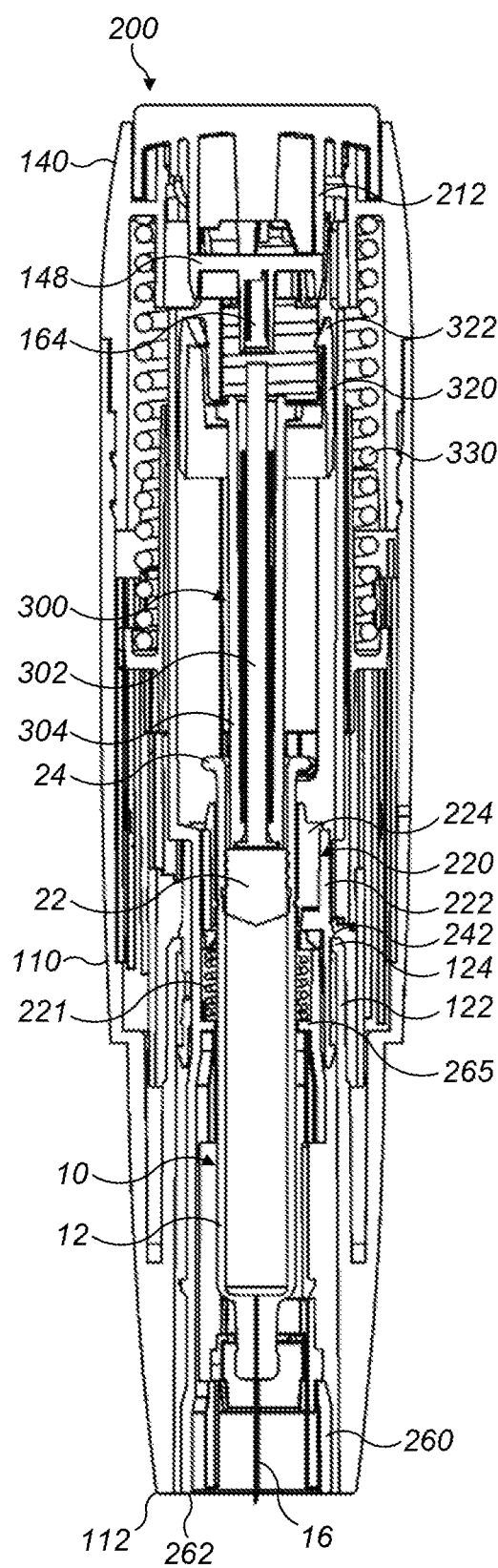
Figure 24A:
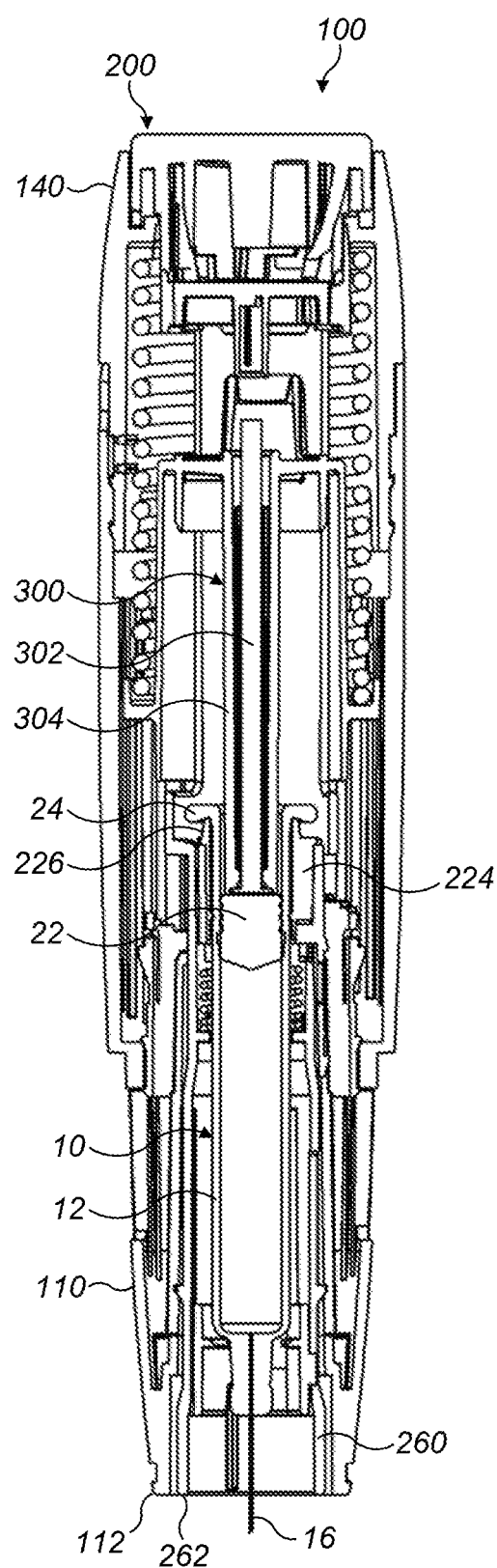
Figure 24B:
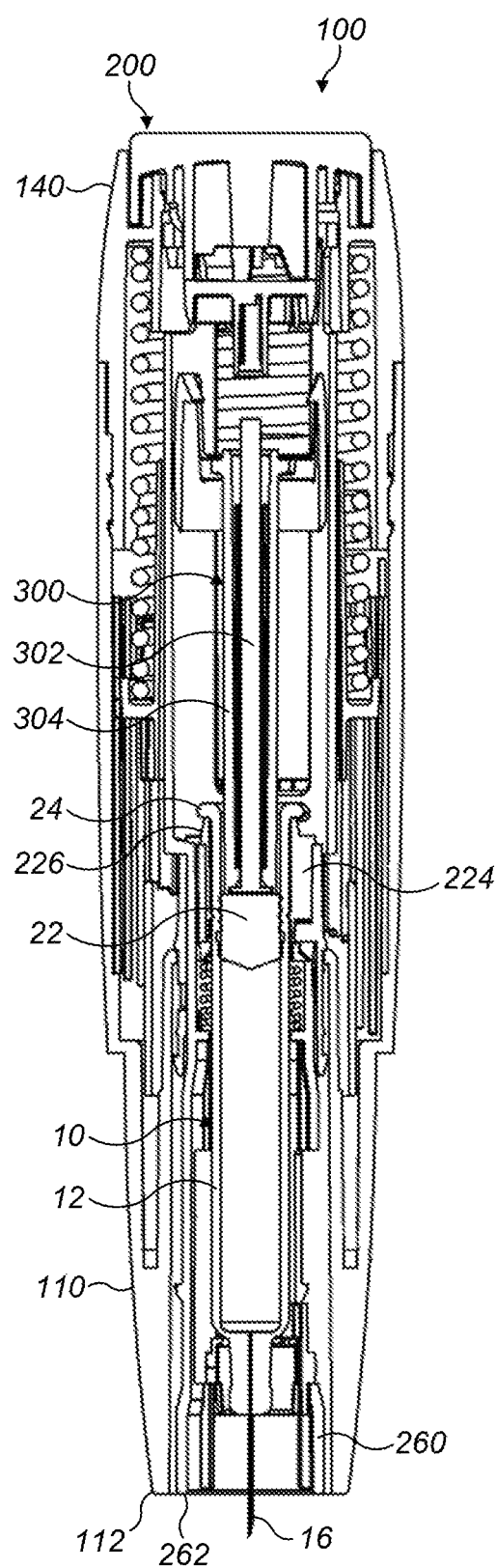
Figure 25A:
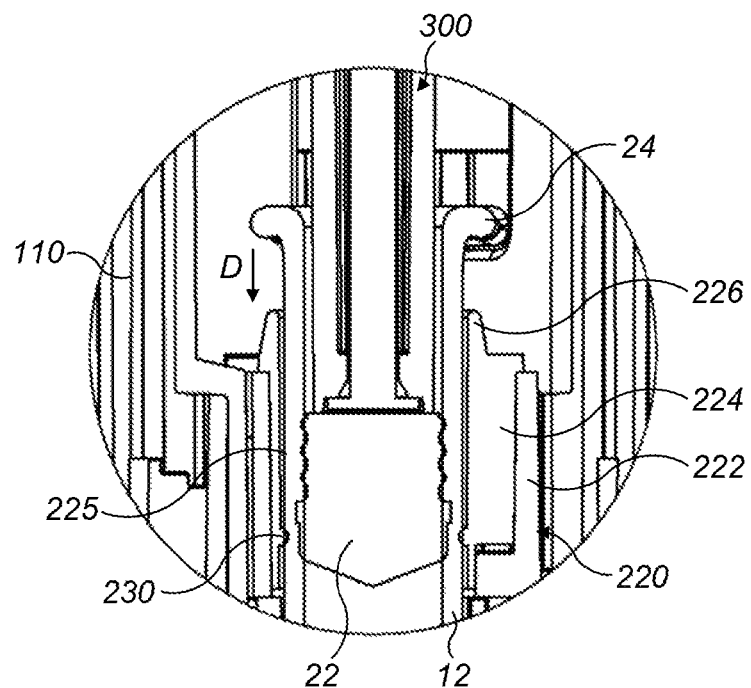
Figure 25B:
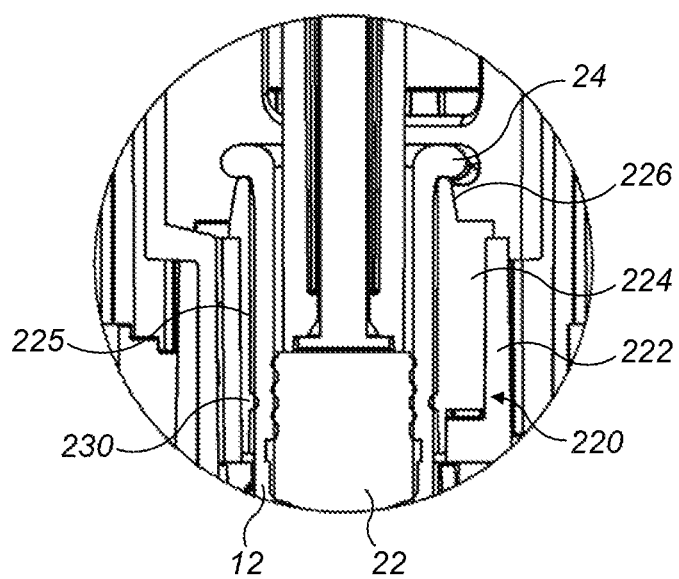
Figure 26A:
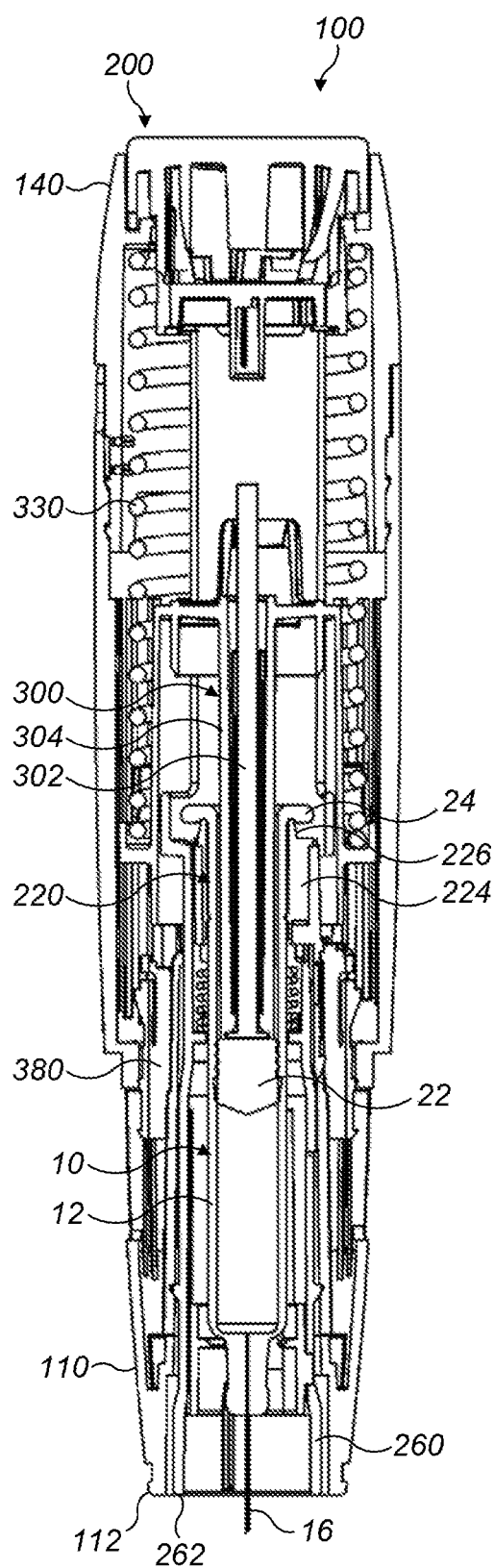
Figure 26B:
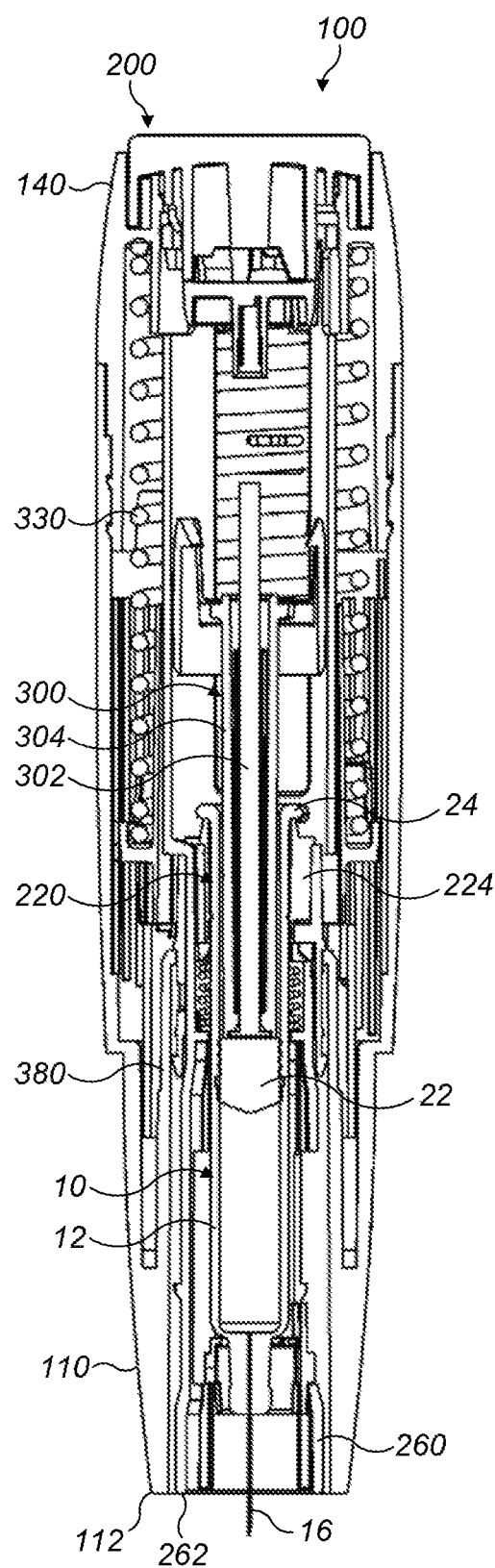
Figure 27:
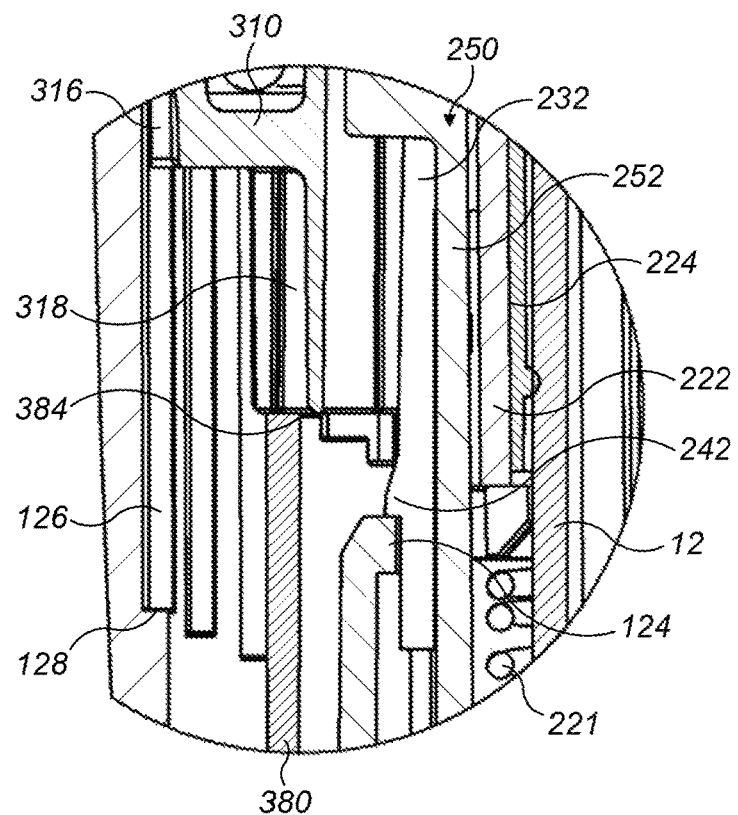
Figure 28:
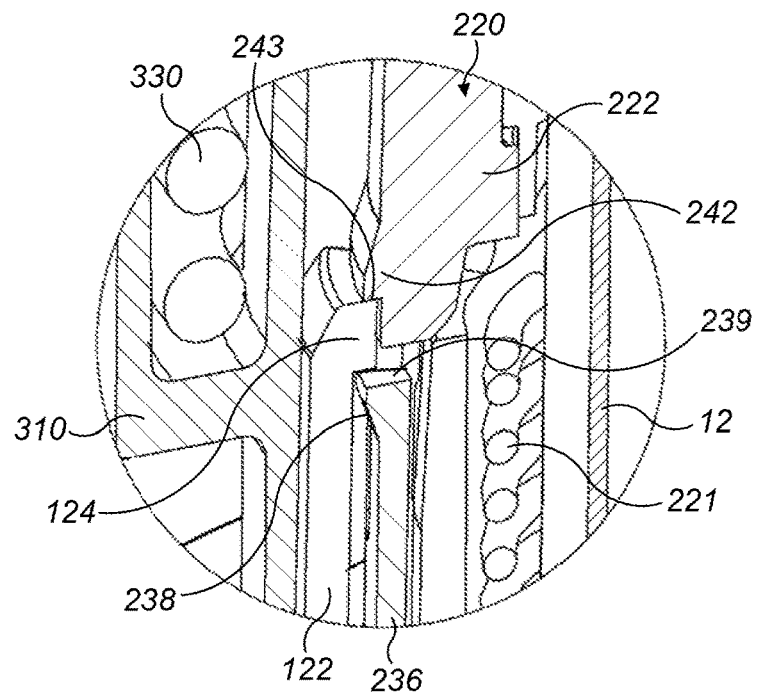
Figure 29A:
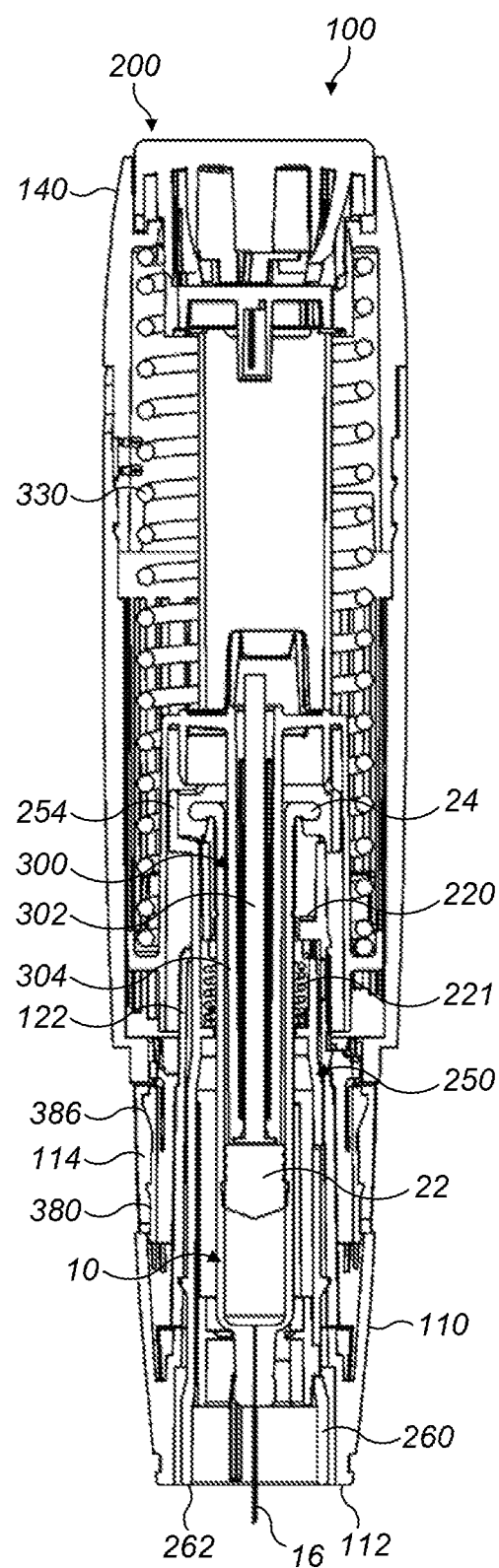
Figure 29B:
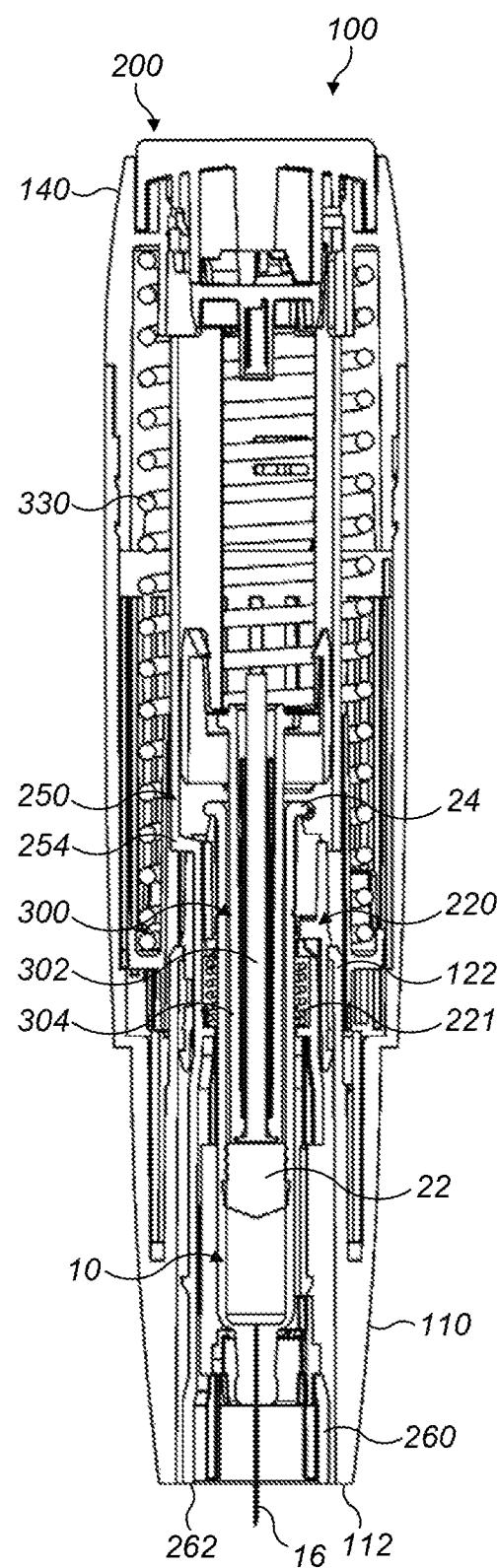
Figure 30A:
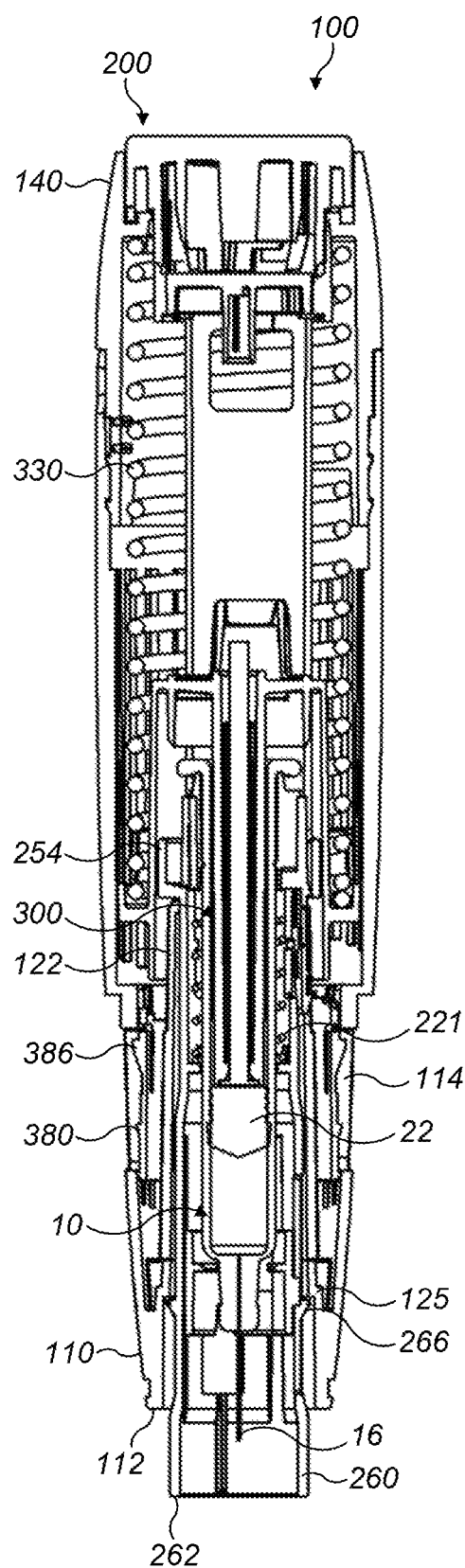
Figure 30B:
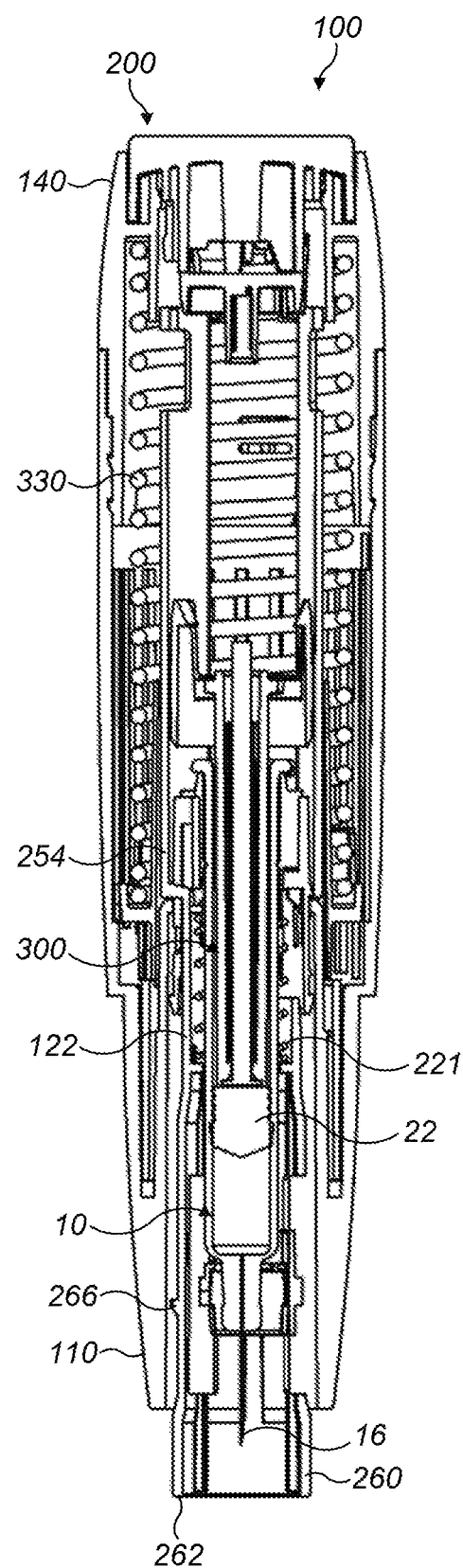
Figure 33:
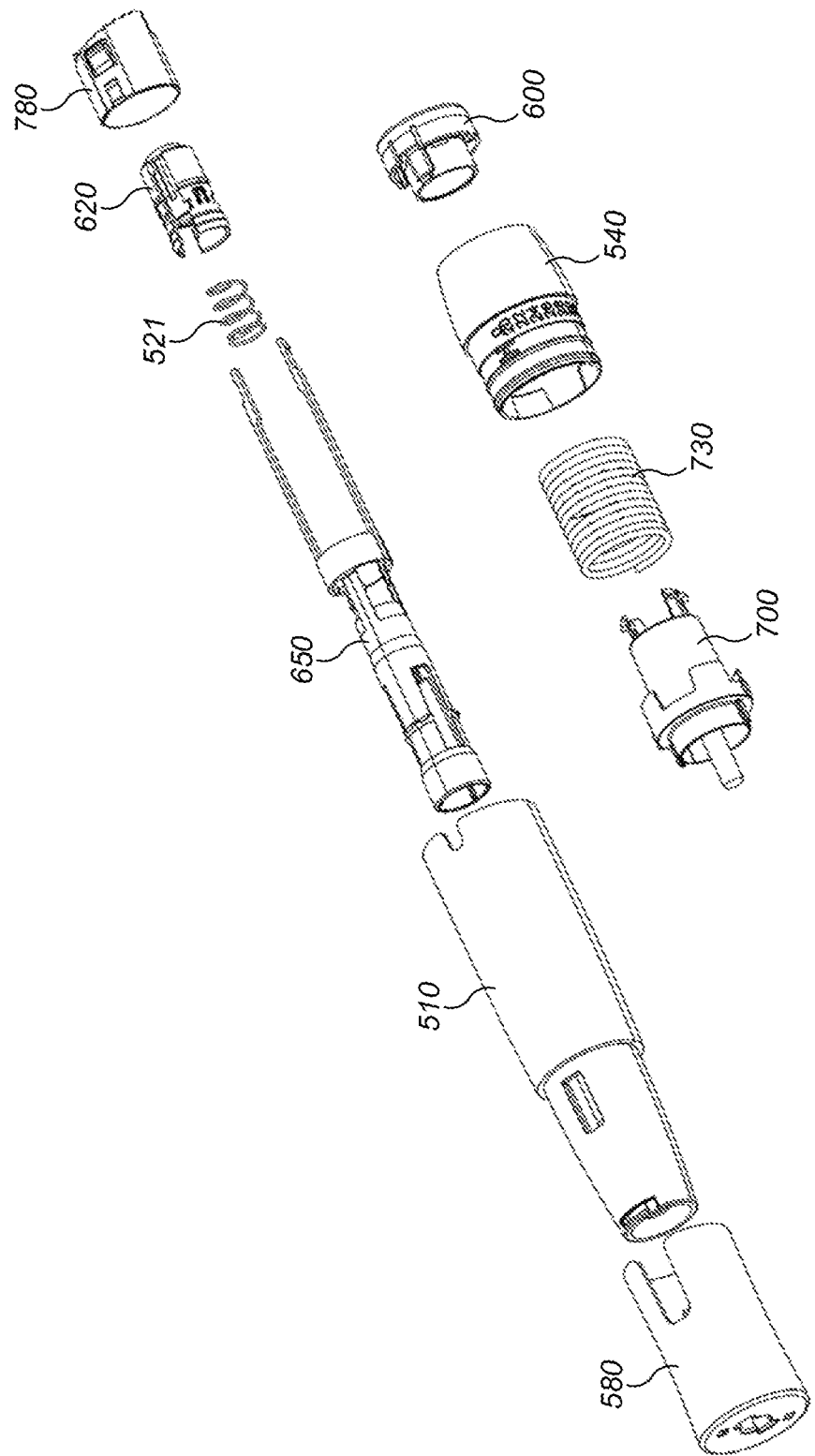
Figure 34A:
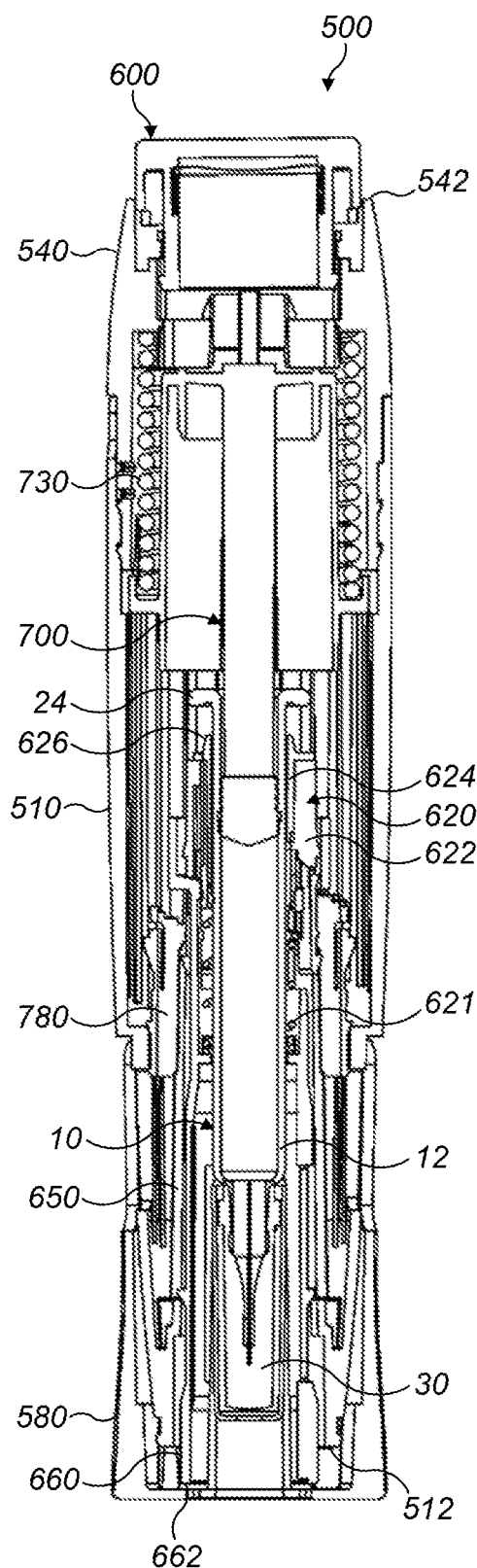
Figure 34B:
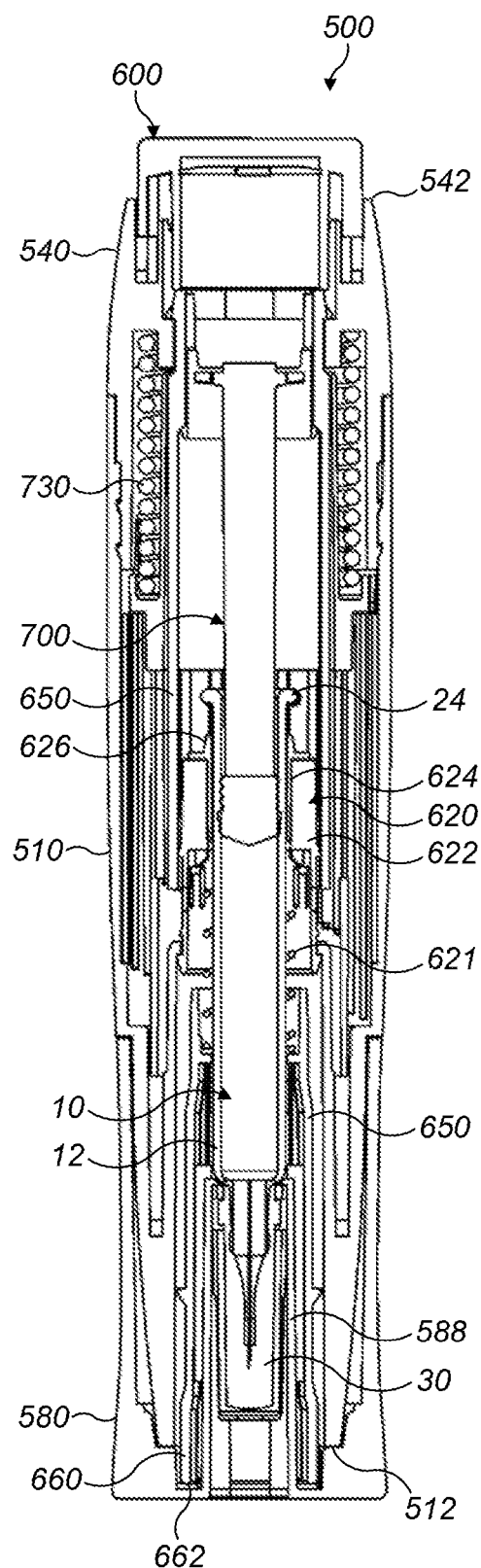
Figure 35A:
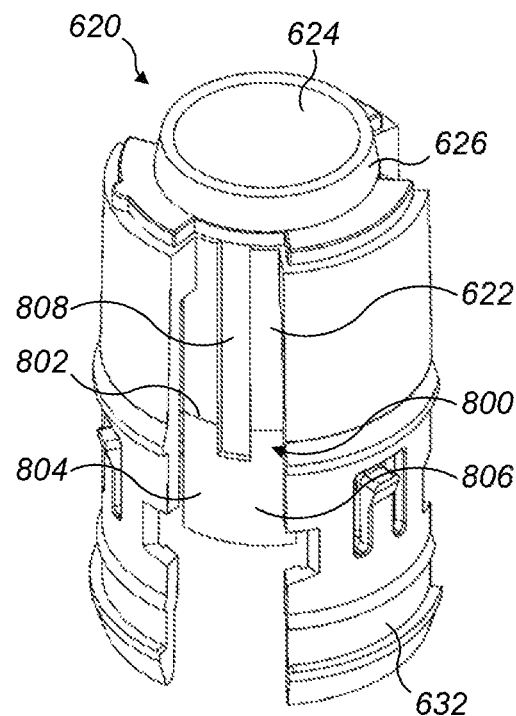
Figure 35B:
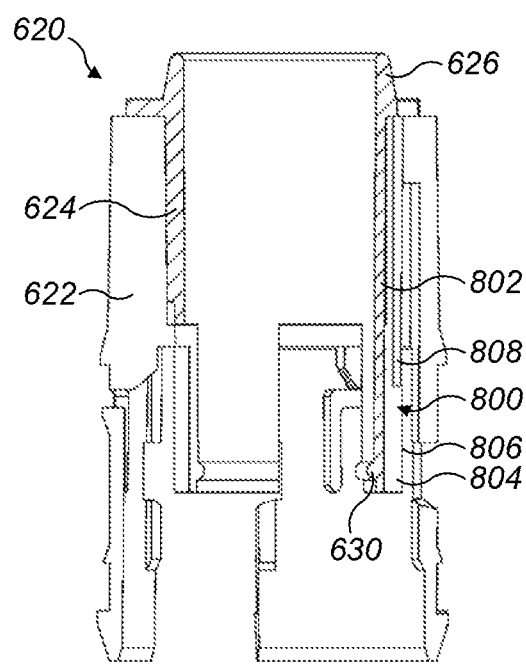
Figure 36:
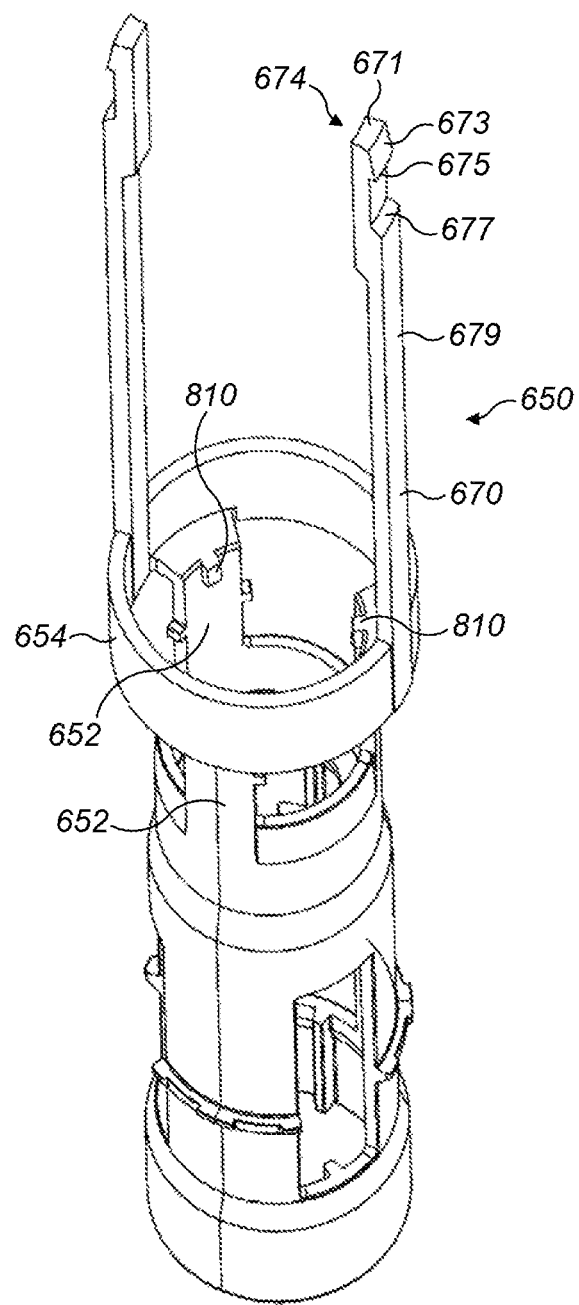
Figure 37:
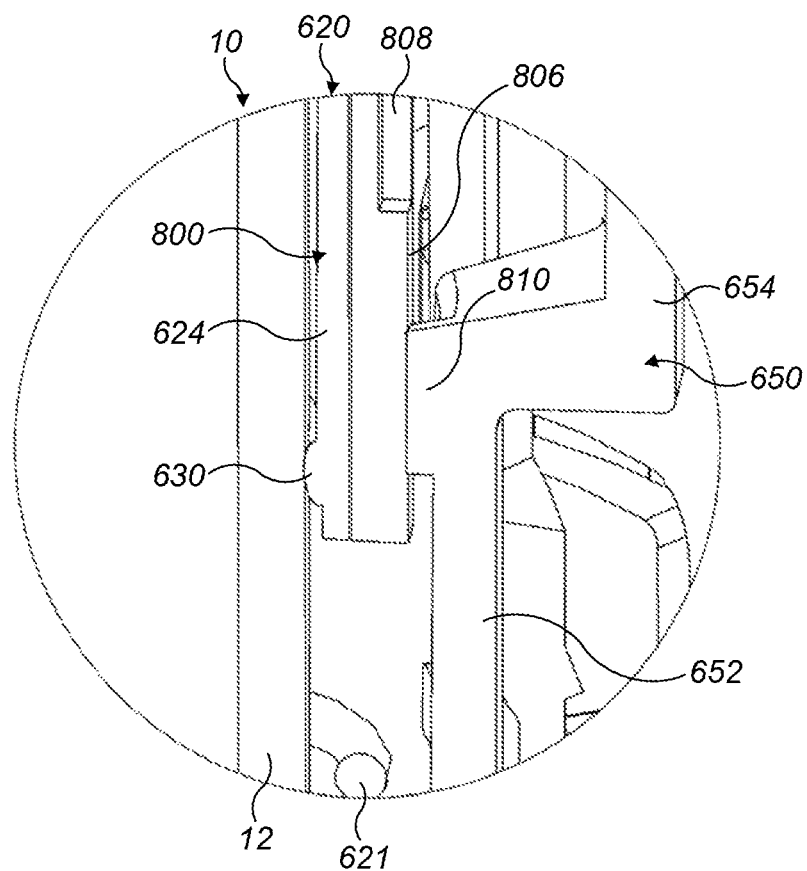
Figure 38A:
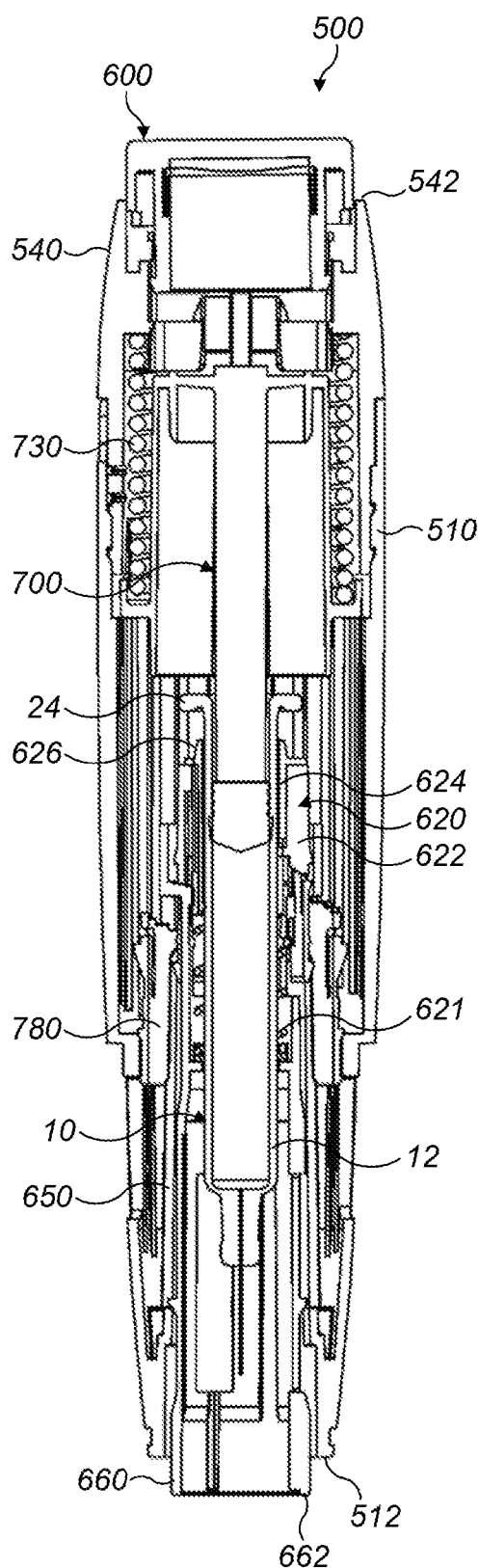
Figure 38B:
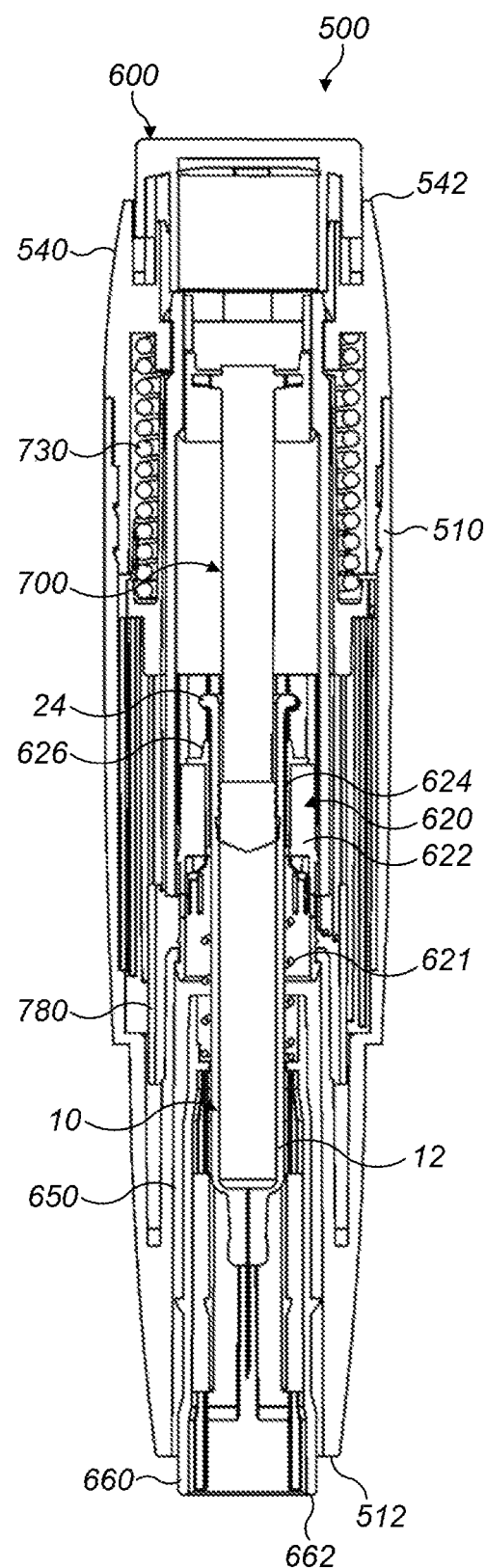
Figure 39:
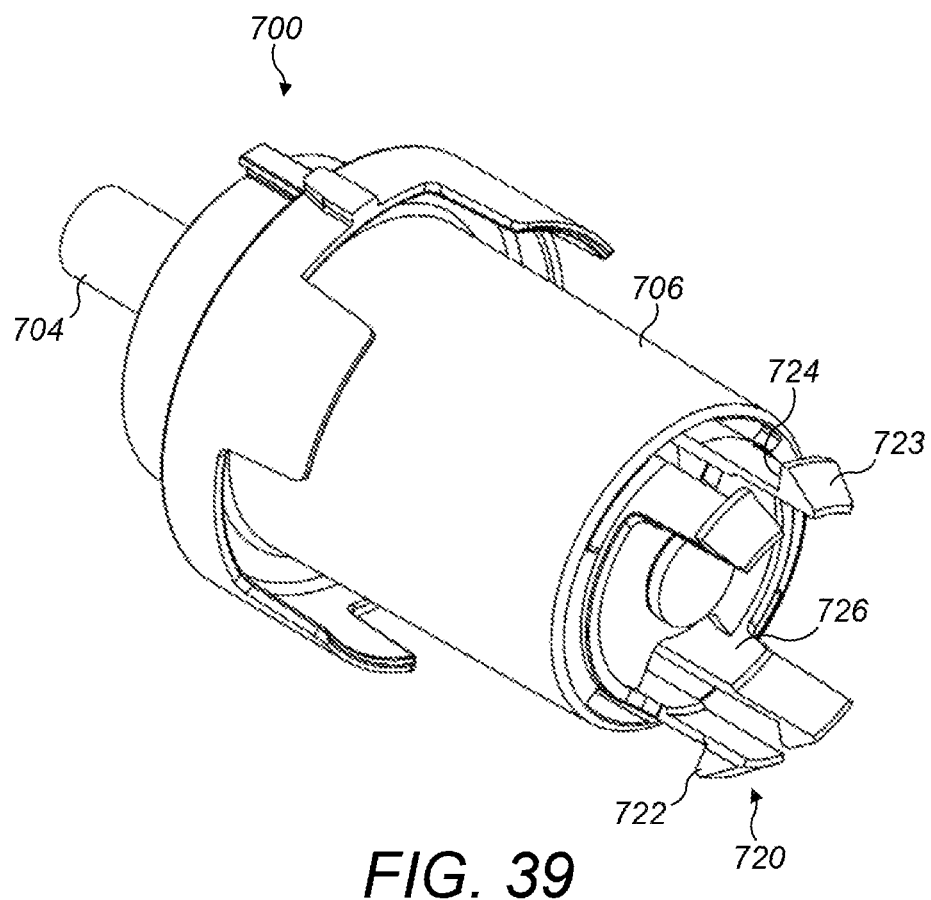
Figure 40:
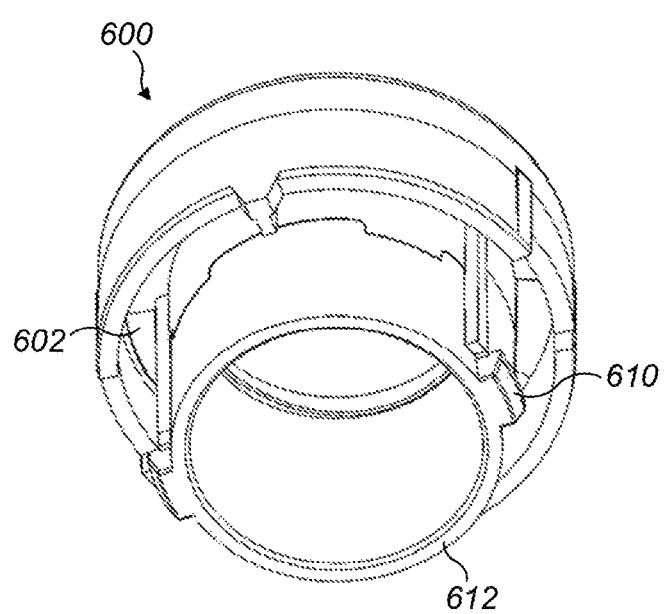
Figure 41:
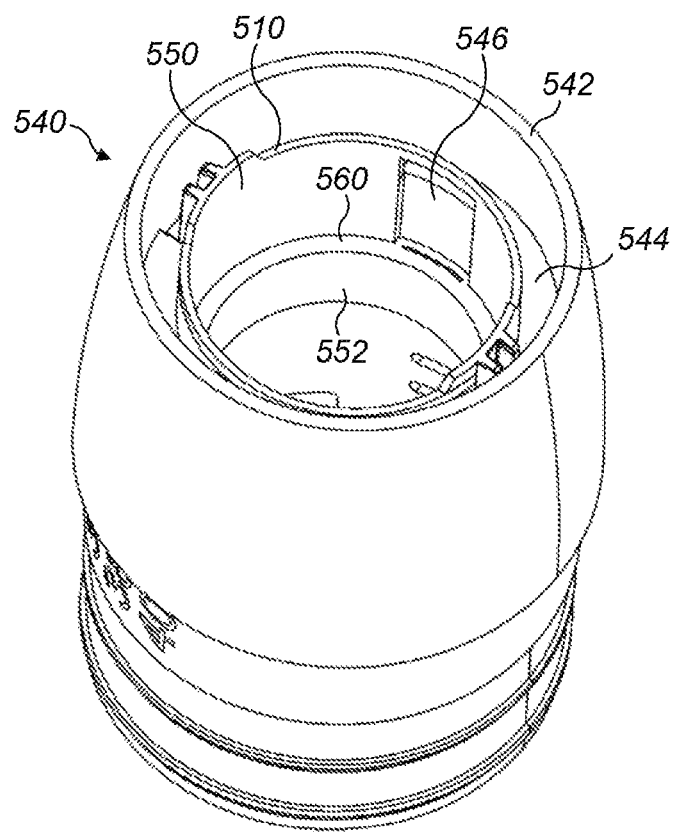
Figure 42:
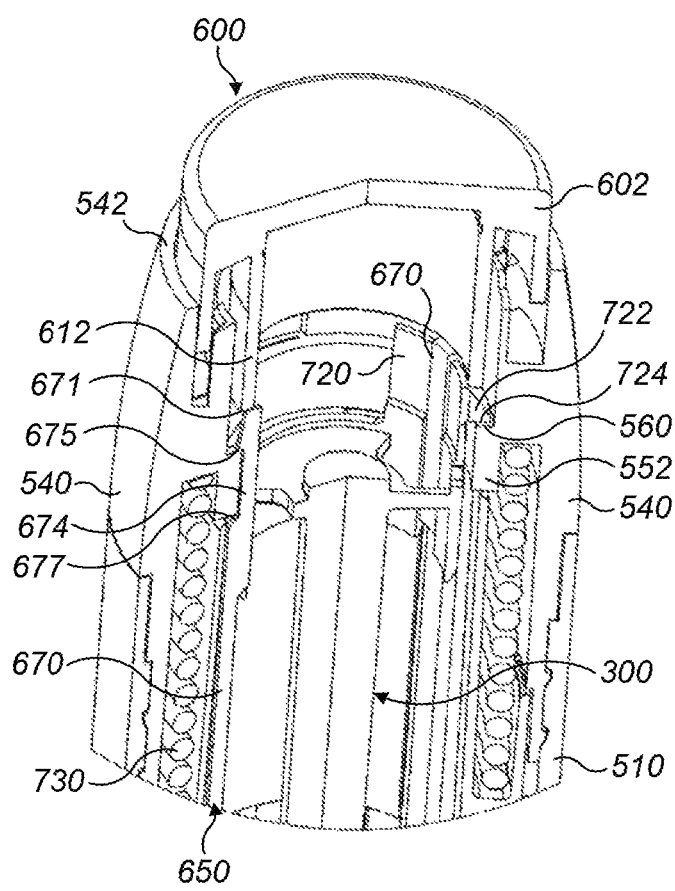
Figure 43:
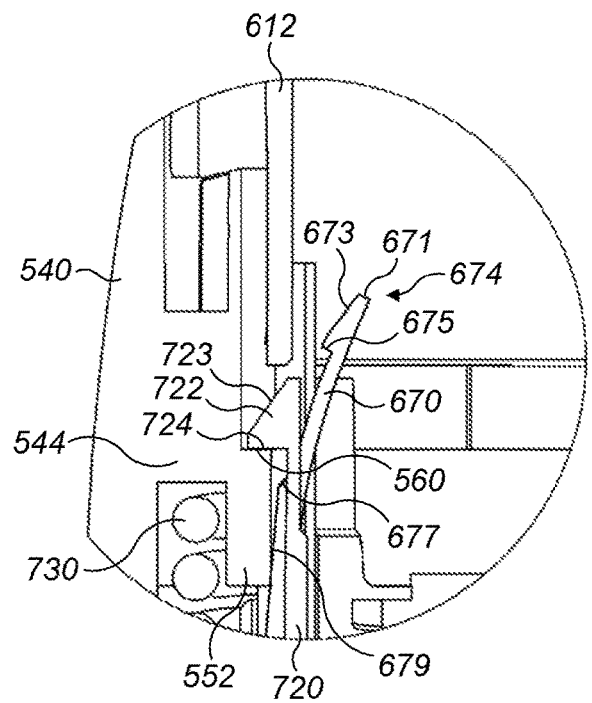
Figure 44:
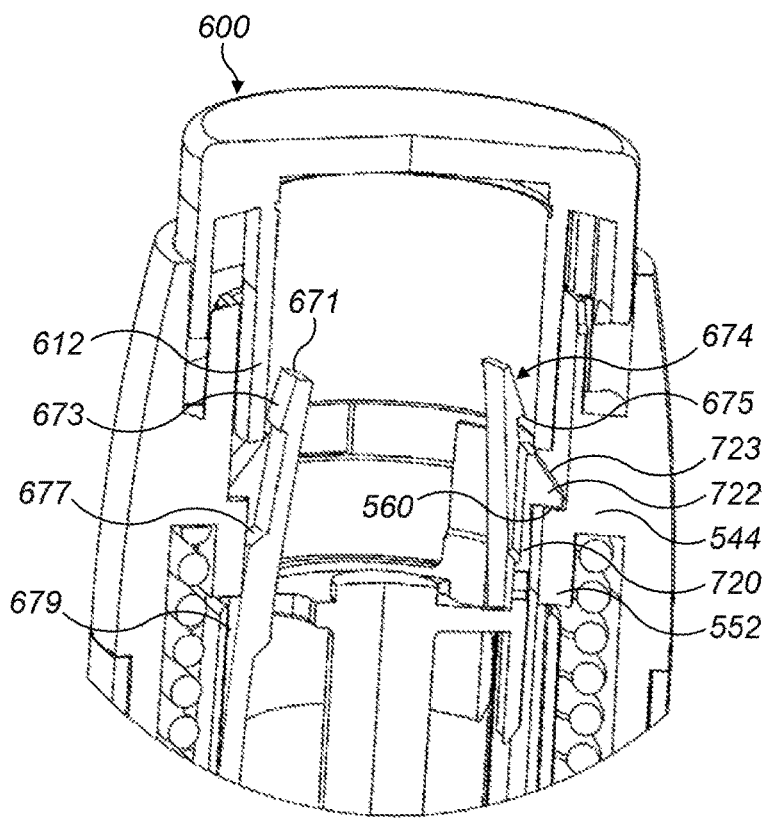
Figure 45A:
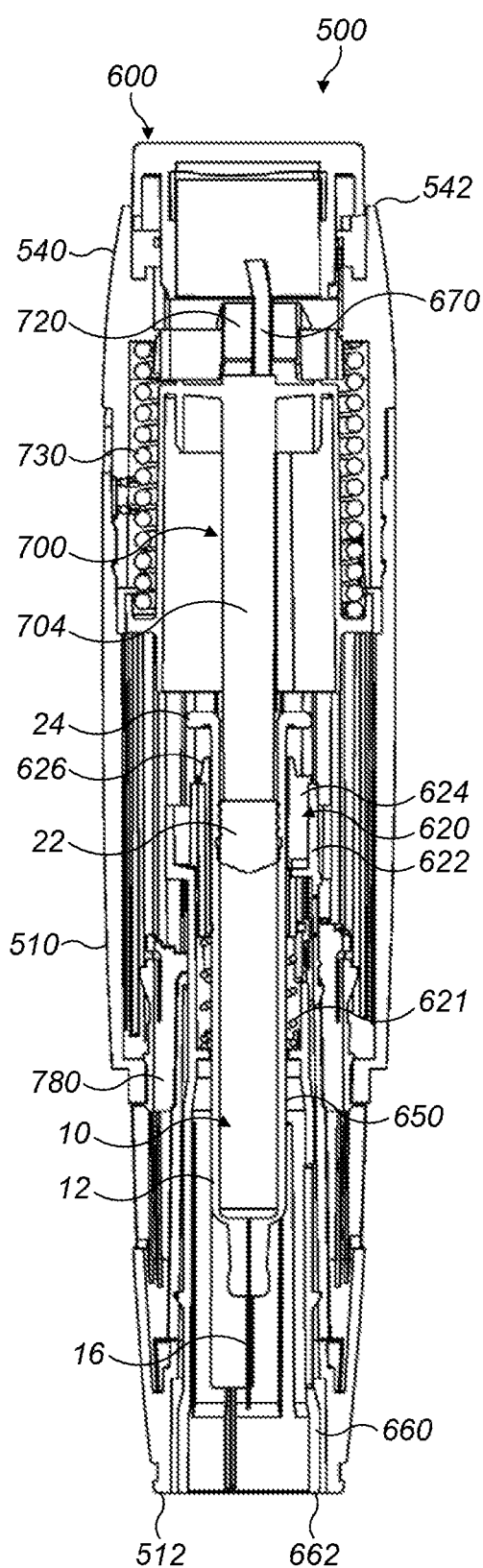
Figure 45B:
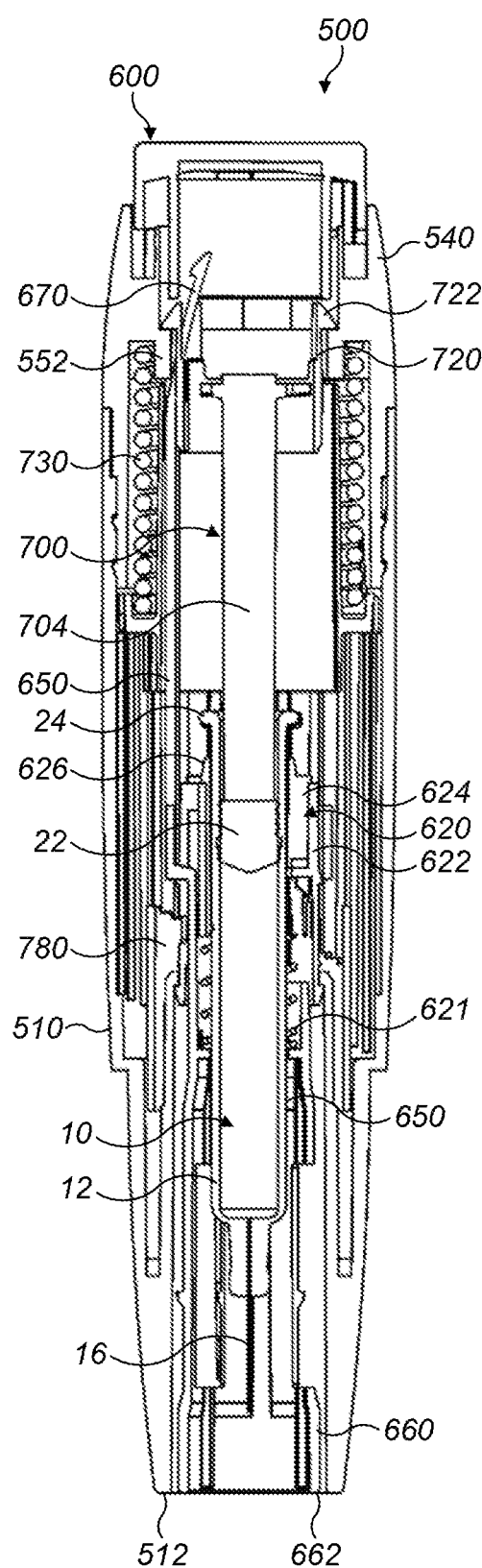
Figure 46A:
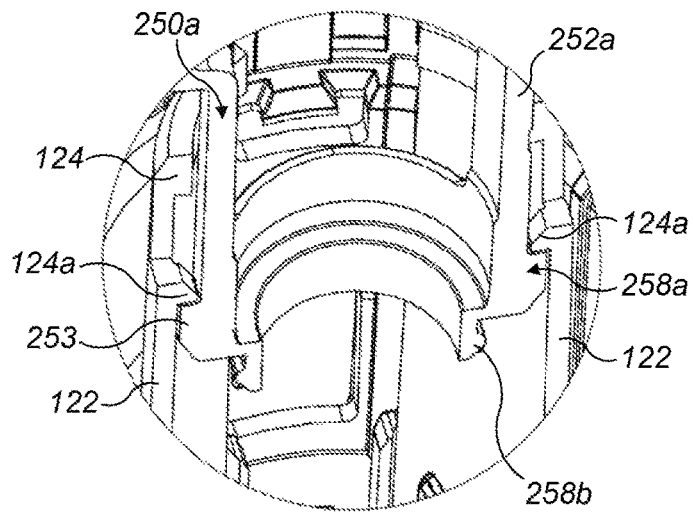
Figure 46B:
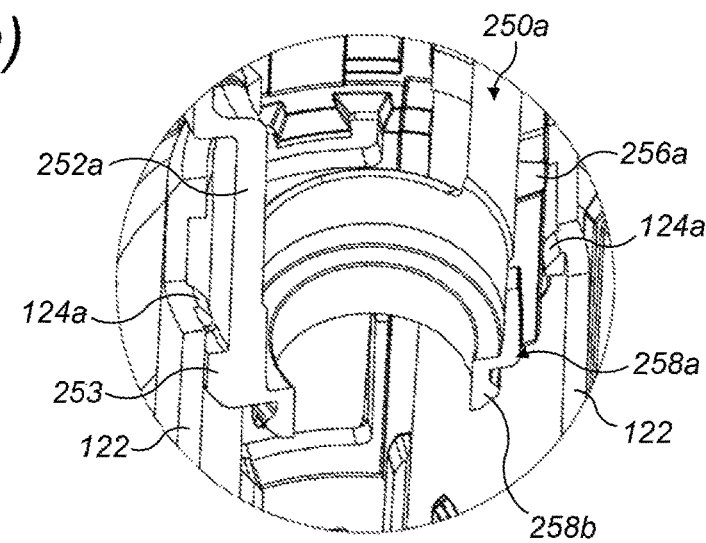
Figure 46C:
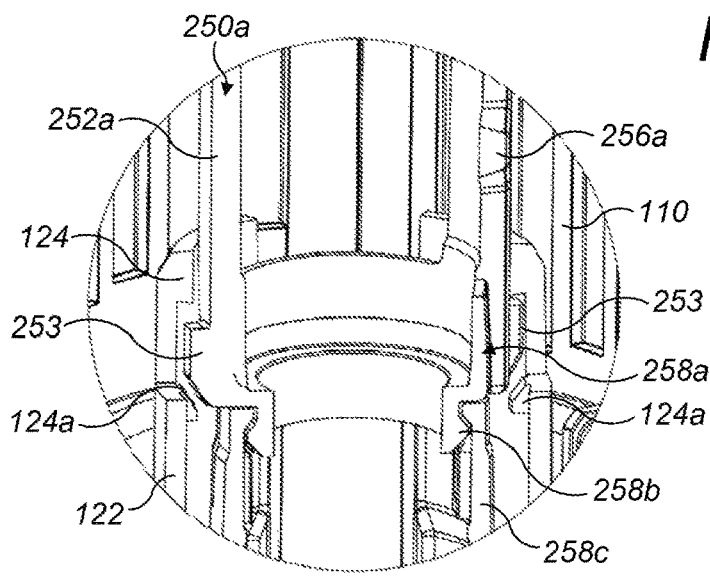
Figure 47:
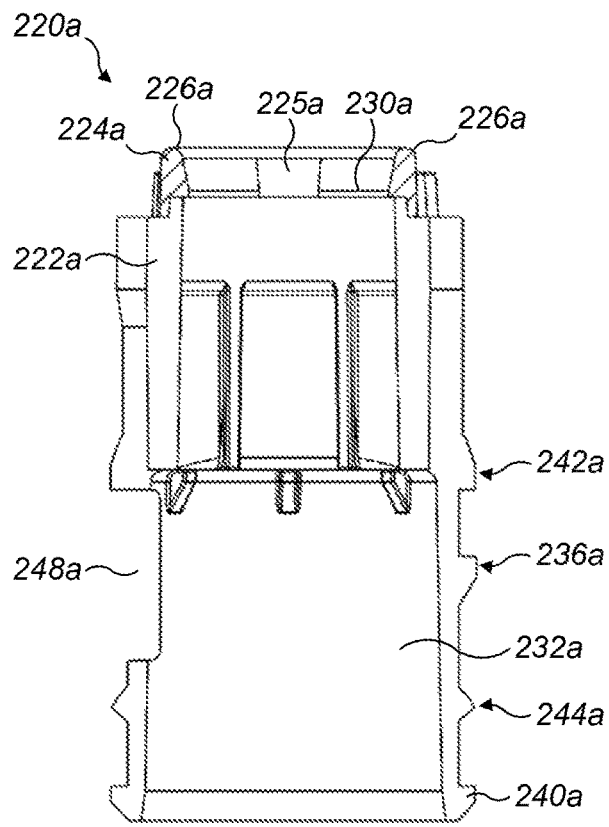
Figure 48:
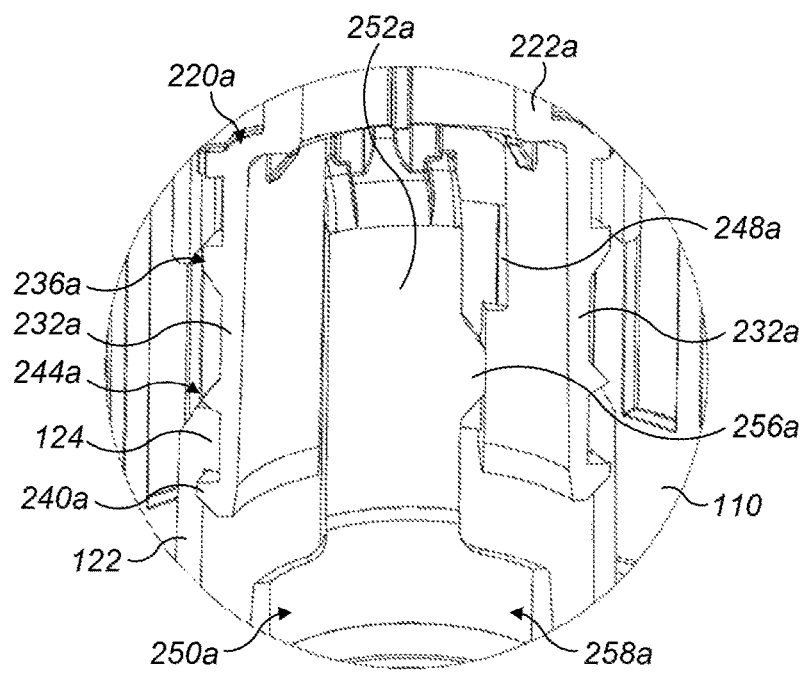

FIGS. 4(a) and 4(b) are cross-sectional views of the injection device of FIG. 1 on planes A-A and B-B, respectively, when the device is in an initial state;

FIGS. 5(a) and 5(b) are isometric and cross-sectional views, respectively, of a carrier assembly of the injection device of FIG. 1;

FIG. 6 is an isometric view of an interlock component of the injection device of FIG. 1;

FIG. 7 is an isometric view of a shuttle member of the injection device of FIG. 1;

FIG. 8 is an isometric view of a cap of the injection device of FIG. 1;

FIG. 9(a) is an isometric view of a front housing body of the injection device of FIG. 1, and FIG. 9(b) is a cut-away isometric view showing an interaction between the front housing body and the cap;

FIG. 10 is an isometric view of a plunger of the injection device of FIG. 1;

FIG. 11 is an isometric view of a trigger component of the injection device of FIG. 1;

FIG. 12 is an isometric view of a rear housing body of the injection device of FIG. 1;

FIG. 13 is an isometric view of a feedback component of the injection device of FIG. 1;

FIG. 14 is a cross-sectional view of part of the injection device of FIG. 1, showing a carrier lock arrangement;

FIG. 15 is a cross-sectional view of part of the injection device of FIG. 1, showing a priming mechanism;

FIGS. 16(a) and 16(b) are cross-sectional views of two parts of the injection device of FIG. 1 before operation of the priming mechanism;

FIGS. 17(a) and 17(b) are cross-sectional views corresponding to those shown in FIGS. 16(a) and 16(b) after operation of the priming mechanism;

FIGS. 18(a) and 18(b) are cross-sectional views of the injection device of FIG. 1 on planes A-A and B-B, respectively, when the device is in a primed state;

FIGS. 19(a) and 19(b) are isometric views of a proximal part of the injection device of FIG. 1, showing a dose selector in a first position and a second position, respectively;

FIGS. 20(a) and 20(b) are cross-sectional views of part of the injection device of FIG. 1 showing a trigger component locking mechanism in a locked state and an unlocked state, respectively;

FIGS. 21(a) and 21(b) are cross-sectional views of part of the injection device of FIG. 1 showing the trigger component locking mechanism in the locked state and the unlocked state, respectively, on a different plane to the views of FIGS. 20(a) and 20(b);

FIGS. 22(a) and 22(b) are cross-sectional views of part of the injection device of FIG. 1 showing the trigger component locking mechanism in the unlocked state and in a fired state, respectively, on a different plane to the views of FIGS. 21(a) and 21(b);

FIGS. 23(a) and 23(b) are cross-sectional views of the injection device of FIG. 1 on two perpendicular planes at the start of insertion stroke of the device;

FIGS. 24(a) and 24(b) are cross-sectional views of the injection device of FIG. 1 on two perpendicular planes at the end of an initial part of the insertion stroke of the device;

FIGS. 25(a) and 25(b) are cross-sectional views of part of the injection device of FIG. 1, showing the relationship of a syringe and the carrier assembly at the start of the insertion stroke and at the end of the initial part of the insertion stroke, respectively;

FIGS. 26(a) and 26(b) are cross-sectional views of the injection device of FIG. 1 on two perpendicular planes during injection of a medicament;

FIG. 27 is a cross-sectional view of part of the injection device of FIG. 1, showing cooperation between the plunger and the feedback component during injection of the medicament;

FIG. 28 is a cross-sectional view of part of the injection device of FIG. 1, showing cooperation between the carrier assembly and the front housing body at the end of the insertion stroke;

FIGS. 29(a) and 29(b) are cross-sectional views of the injection device of FIG. 1 on two perpendicular planes at the end of injection;

FIGS. 30(a) and 30(b) are cross-sectional views of the injection device of FIG. 1 on two perpendicular planes after removal of the device from an injection site;

FIG. 31 is a cross-sectional view of part of the injection device of FIG. 1, showing cooperation between the interlock component and the front housing body after removal of the device from the injection site;

FIG. 32 is an isometric cross-sectional view of another injection device according to the present invention;

FIG. 33 is an exploded view of the injection device of FIG. 32;

FIGS. 34(a) and 34(b) are cross-sectional views of the injection device of FIG. 32 on two perpendicular planes when the device is in an initial state;

FIGS. 35(a) and 35(b) are isometric and cross-sectional views, respectively, of a carrier assembly of the injection device of FIG. 32;

FIG. 36 is an isometric view of an interlock component of the injection device of FIG. 32;

FIG. 37 is a cross-sectional view of part of the injection device of FIG. 32, showing a container clamping arrangement;

FIGS. 38(a) and 38(b) are cross-sectional views of the injection device of FIG. 32 on two perpendicular planes when the device is in a locked state;

FIG. 39 is an isometric view of a plunger of the injection device of FIG. 32;

FIG. 40 is an isometric view of a trigger component of the injection device of FIG. 32;

FIG. 41 is an isometric view of a rear housing body of the injection device of FIG. 32;

FIG. 42 is a cut-away view of part of the injection device of FIG. 32 showing a trigger component locking mechanism in a locked state;

FIG. 43 is a cut-away view of part of the injection device of FIG. 32 showing the trigger component locking mechanism in an unlocked state;

FIG. 44 is a cross-sectional view of part of the injection device of FIG. 32 showing the trigger component locking mechanism in the unlocked state;

FIGS. 45(a) and 45(b) are cross-sectional views of the injection device of FIG. 32 on two perpendicular planes when the device is in an unlocked state;

FIGS. 46(a), 46(b) and 46(c) are sectional views of a variant of the injection device of FIG. 1, showing the operation of an interlock component when in a first, secured position, an unsecured position, and a second position, respectively;

FIG. 47 is a cross-sectional view of a carrier assembly of a variant of the injection device of FIG. 1; and FIG. 48 is a cut-away view of part of an injection device including the carrier assembly of FIG. 47.

FIGS. 1 to 4 show an injection device 100 according to a first embodiment of the invention. Throughout the following description, the terms "front", "distal" and related terms are used to refer to the end of the device 100 that is towards the patient's skin in use (i.e. the lower end of the device in FIGS. 1(a) and 1(b)), and the terms "rear", "proximal" and related terms are used to refer to the end of the device 100 that is furthest from the skin in use (i.e. the upper end of the device 100 in FIGS. 1(a) and 1(b)). Terms such as "turning" and "rotation" are intended to describe turning movement around the longitudinal axis of the device (i.e. the vertical axis in FIGS. 1(a) and 1(b)), except if the context demands otherwise.

Figure 3:
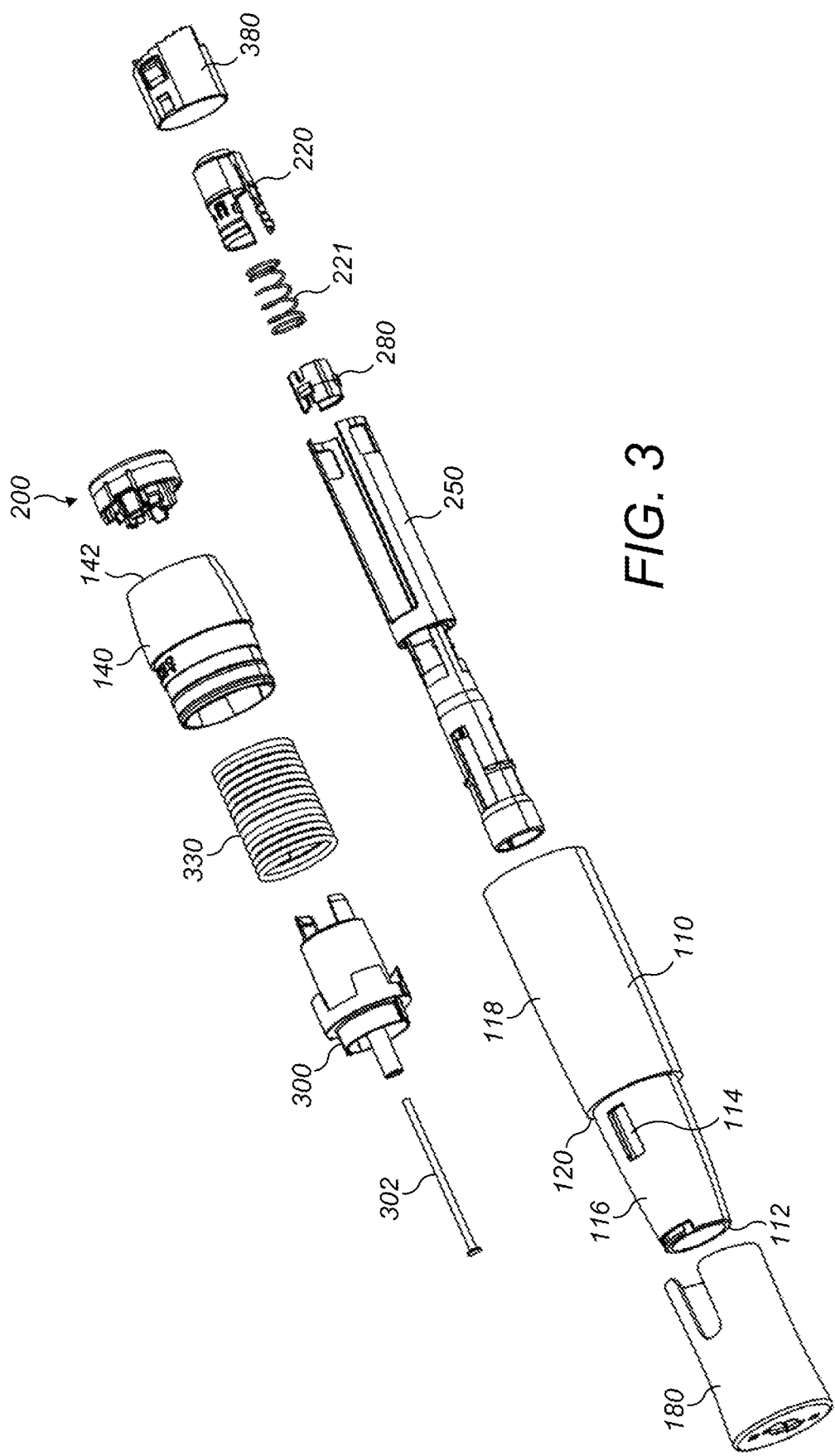
FIG. 3 is an exploded view of the injection device of FIG. 1.

Referring first to FIGS. 1 to 3, the device 100 includes an elongate two-part housing comprising a generally tubular front housing body 110 and a generally tubular rear housing body 140 rotatably attached to the proximal end of the front housing body 110. In an initial state of the device, the distal end 112 of the front housing body 110 is closed by a deshielder cap 180. A trigger component in the form of a trigger button 200 is retained in the proximal end 142 of the rear housing body 140.

Referring additionally to FIGS. 4(a) and 4(b), the front housing body 110 houses a medicament container, which in this case is a pre-filled syringe 10. The syringe 10 is preferably of a type known in the art, for example a Hypak syringe. The syringe 10 comprises a generally tubular glass barrel or body 12. At its distal end, the body 12 is formed into a reduced-diameter end portion 14 that carries a staked hypodermic needle 16. A shoulder 18 of the syringe body 12 is formed where the end portion 14 meets the remaining portion of the body 12. The body 12 is filled with a quantity of medicament 20 and is closed by a stopper 22 that is slidably received in the body 12. An outwardly-projecting flange 24 is provided at the proximal end of the body 12.

A shield 30 is removably attached to the distal end portion 14 of the syringe body 12. In this example, the shield 30 is of a type known in the art as a rigid needle shield and comprises an elastomeric insert or inner shield 32 having a funnel-shaped cavity into which the needle 16 is inserted, and a rigid outer cap or cover 34. The shield 30 serves to seal the needle 16 to preserve sterility of the needle 16 and to prevent leakage of medicament 20 during transport and storage of the device 100.

The syringe body 12 is received in a carrier assembly 220. The carrier assembly is guided for axial movement within the front housing body 110 by an interlock component 250, which is arranged concentrically around the carrier assembly 220. An interlock spring 221 acts to bias the carrier assembly 220 and the interlock component 250 apart. The carrier assembly 220 and the interlock component 250 are shown in isolation in FIGS. 5 and 6, respectively, and will be described in more detail below.

The interlock component 250 also guides a shuttle member 280 for axial movement with respect to the front housing body 110. The shuttle member 280 cooperates with the cap 180 to form part of a priming mechanism of the device 100, as will be explained below. In the initial state of the device, the shuttle member 280 is disposed concentrically around the shoulder 18 of the syringe body 12. The shuttle member 280 and the cap 180 are shown in isolation in FIGS. 7 and 8, respectively, and will be described in more detail below.

The device 100 also includes a piston or plunger 300 having a priming pin 302. The plunger 300 is rotatable with the rear housing body 140 and, in use, is guided for axial movement by the front housing body 110. The plunger 300 and the front housing body 110 are shown in isolation in FIGS. 9 and 10, respectively, and will be described in more detail below.

The device 100 is further provided with a drive mechanism arranged to hold the plunger 300 in a starting position relative to the front housing body 110 and to move the plunger 300 in the distal direction from the starting position to engage with the stopper 22 of the syringe 10. As will be explained in more detail below, the drive mechanism includes a drive spring 330 that acts between the plunger 300 and the rear housing body 140 to bias the plunger 300 in the distal direction, and a latching arrangement for latching the plunger 300 in the starting position and for releasing the plunger 300 when the trigger button 200 is depressed. FIGS. 11 and 12 show the trigger button 200 and the rear housing body 140, respectively, in isolation. A generally tubular feedback component 380, shown in isolation in FIG. 13, is disposed concentrically between the interlock component 250 and the front housing body 110 for interaction with the plunger 300 after release of the plunger 300. The front housing body 110 includes a window 114 for viewing of the feedback component 380 at the end of an injection.

Referring now to FIG. 5, the carrier assembly 220 comprises a generally tubular carrier support 222 that receives and supports an elastomeric insert or sleeve 224. The sleeve 224 defines a bore 225 for receiving the syringe body 12 and the sleeve 224 is sized so as to deform against syringe body 12 to create a frictional or interference fit. The sleeve 224 is made from a material with a suitably high coefficient of friction on the glass body 12, such as a thermoplastic elastomer.

A proximal end of the sleeve 224 extends beyond the proximal end of the carrier support 222 to define an annular damping element 226. Distal movement of the sleeve 224 with respect to the carrier support 222 is prevented by a shoulder 228 provided at the proximal end of the damping element 226. Rotation of the sleeve 224 with respect to the carrier support 222 is prevented by locating tabs 229 that extend radially from the damping element 226. The shoulder 228 and the locating tabs 229 abut the proximal end of the sleeve 224. The sleeve 224 may be further secured to the carrier support 222 by any suitable means, for example by chemical and/or mechanical bonding.

Adjacent to its distal end, the internal surface of the bore 225 of the sleeve 224 is provided with a deformable projection in the form of an annular rib 230. When the syringe body 12 is in place in the sleeve 224, the rib 230 deforms against the syringe body 12 to increase further the frictional force that acts between the sleeve 224 and the syringe body 12.

The carrier support 222 is provided with distally-extending guide legs 232. In this example, three guide legs 232 are present, but any suitable number of guide legs could be provided. Each guide leg 232 is arcuate in cross-section so that the three legs 232 together define a tubular form that is coaxial with the longitudinal axis of the device 100. The proximal end of each guide leg 232 is attached to the carrier support 222, with a proximal part of the inner face of each guide leg 232 in contact with a corresponding locating tab 229, while the distal end of each guide leg 232 is free. In this way, the distal ends of the guide legs 232 are able to flex radially with respect to the carrier support 222 so that each guide leg 232 defines a beam element of the carrier support 222.

The guide legs 232 are spaced angularly around the carrier support 222, so as to define longitudinally-extending channels 234 between the adjacent guide legs 232. Each guide leg 232 is provided with an elongate latch member 236 disposed in a cut-out 237 of the leg 236.

The distal end of each latch member 236 is attached to the leg 232. The proximal end of each latch member 236 is wedge-shaped to define a ramped face 238 that projects radially beyond the outer surface of the respective leg 232. The proximal end face of each latch member 232 defines a blocking face 239 disposed perpendicular to the axis of the device 100.

The outside surface of each guide leg 232 is provided with three axially-spaced, circumferentially-extending projections. A blocking projection 240 having a proximally-directed face 241 is disposed adjacent to the distal end of each guide leg 232. A stop projection 242 having a distally-directed face 243 is spaced proximally from each blocking projection 240 and approximately adjacent to the distal end of the sleeve 224. A lock projection 244, having ramped proximal and distal faces 245, 246, is disposed between the blocking projection 240 and the stop projection 242 on each guide leg 232.

A pair of elongate ribs or rails 247 are provided on the inner surface of each guide leg 232. One rail 247 is provided on each side of the guide leg 232, so that each rail 247 runs adjacent to one of the channels 234 between the guide legs 232. Each rail 247 starts adjacent to the lock projection 244 and extends proximally towards the fixed proximal end of the respective guide leg 232. The rails 247 are interrupted by notches 248 formed in the sides of each guide leg 232. Each notch 248 is positioned intermediate the lock projection 240 and the stop projection 242 on the respective guide leg 232.

Referring back to FIG. 4, the carrier assembly 220 is guided for axial movement in the device 100 by three longitudinally-extending guide arms 252 of the interlock component 250. Only one of the guide arms 252 can be seen in FIG. 4(a), and all of the guide arms 252 are out-of-plane in FIG. 4(b) and cannot be seen. Each guide arm 252 is accommodated in one of the channels 234 defined between the respective guide legs 232 of the carrier assembly 220.

Referring additionally to FIG. 6, the guide arms 252 of the interlock component 250 are arcuate in cross-section so that the three guide arms 252 together define a tubular form having a smaller outer diameter than the inner diameter of the tubular form defined by the guide legs 232 of the carrier assembly 220. The proximal ends of the guide arms 252 are attached to a tubular ring part 254 that has a larger inner diameter than the outer diameter of the carrier assembly 220. In this way, the carrier assembly 220 can be accommodated inside the ring part 254, with the guide legs 232 of the carrier assembly 220 interdigitated with the guide arms 252 of the interlock component 250. Projections or tabs 256 are disposed on each side of each guide arm 252 for cooperation with the rails 247 of the guide legs 232, as will be explained in more detail below.

The distal ends of the guide arms 252 are attached to a tubular sleeve part 258 of the interlock component 250. A distal end part of the sleeve part 258 forms a tubular needle shroud 260 having a distal end face 262. Three longitudinally-extending guide slots 264 are formed in the sleeve part 258 adjacent to the needle shroud 260.

The sleeve part 258 is also provided with a clip formation 266 in the form of an annular projection having a ramped distal face 267 and a proximal face 268 that lies perpendicular to the axis of the device 100. The clip formation 266 is spaced from the needle shroud 260 and is split into three arcuate parts by the guide slots 264.

A pair of interlock fingers 270 project proximally from the ring part 254 of the interlock component 250. Each interlock finger 270 has an aperture or cut-out 272 adjacent to its proximal end. A support pad 274 is disposed on the inside surface of each interlock finger 270 on a proximal side of the respective aperture 272. As will be explained in more detail below, the interlock fingers 270 form part of a locking mechanism for the trigger button 200.

Referring back to FIGS. 4(a) and 4(b), the sleeve part 258 of the interlock component is provided with an internal flange 265 (shown in FIGS. 4(a) and 4(b), not visible in FIG. 6). The flange 265 provides a seating surface for a distal end of the interlock spring 221.

The shuttle member 280 is guided for axial movement in the device 100 by the interlock component 250. Referring additionally to FIG. 7, the shuttle member 280 comprises a C-shaped split ring. The outer surface of the shuttle member 280 is provided with three arcuate guide tabs 282. Each guide tab 282 fits within a respective guide slot 264 of the interlock component 250 so that the shuttle member 280 is held captive by the sleeve part 258 of the interlock component 250. The C-shape of the shuttle member 280 allows the shuttle member 280 to be deformed to clip into the sleeve part 258 of the interlock component 250 during assembly of the device 100.

The inner surface of the shuttle member 280 is provided with a pair of circumferentially-extending collar projections or ribs 284. A central portion of each rib 284 is extended radially to form a carrier tab 286 for engagement with the shoulder 18 of the syringe body 12, as will be explained later.

Referring to FIG. 8, the cap 180 is generally cup-shaped and comprises an outer wall 182, a distal end face 184 and a shield retainer 186 that extends from the end face 184 in a proximal direction. The shield retainer 186 is a generally tubular formation that is split lengthwise on two opposite sides to form two shield retainer arms 188. A clip formation 190 (shown most clearly in FIG. 4(b)) is disposed at the proximal end of each shield retainer arm 188. A cam element in the form of an inclined ramp formation 192 (shown in FIG. 8, not visible in FIG. 4) is provided on the proximal end of each shield retainer arm 188 for cooperation with the shuttle member 280 during operation of the priming mechanism of the device 100, as will be explained in more detail below.

The cap 180 is dimensioned to fit over the front housing body 110 of the device 100. A guide key 194 is provided on the internal surface of the outer wall 182 of the cap 180 for engagement with the front housing body 110, and cut-outs 196 are provided in the outer wall 182 to allow the window 114 of the front housing body 110 to be seen when the cap 180 is in place.

Referring to FIGS. 3 and 9(a), the front housing body 110 is generally tubular and comprises a tapered distal part 116 for receiving the cap 180 and a generally cylindrical proximal part 118 that meets the distal part 116 at a step 120. As shown in FIG. 9(b), the outer surface of the distal part 116 is provided with a channel form or keyway 117 for engagement with the guide key 194 of the cap 180. The keyway 117 has a circumferentially-extending part 117a and a longitudinally-extending part 117b at one end of the circumferentially-extending part 117a, so that the key 194 engages with the keyway 117 in the manner of a bayonet fitting.

Referring back to FIG. 9(a), a pair of part-tubular internal support arms 122 are attached to the distal part 116 of the front housing body 110. The support arms 122 project proximally into the proximal part 118 of the front housing body 110. The inside face of each support arm 122 is provided with a collar 124 at its proximal end for engagement with the guide legs 232 of the carrier assembly 220 (see FIG. 4(b)). A pair of support tabs 125 are disposed towards the distal end of the front housing body 110, with each support tab 125 being positioned between the two support arms 122.

The proximal part 118 of the front housing body 110 serves as a guide for the plunger 300. To this end, the internal surface of the proximal part 118 (shown most clearly in FIG. 9(a)) is provided with a plurality of parallel elongate recess or channels 126. Each channel 126 has a different length to the adjacent channels 126. In this way, the distal end 128 of each channel 126, which provides a stop formation for the plunger 300, is at a different axial position relative to the distal end 112 of the front housing body 110 compared to the neighbouring channels 126. The channels 126 are arranged in pairs, with the channels 126 of each pair being diametrically opposite one another and having equal lengths. The channels 126 are arranged in order of increasing length, moving around the circumference of the front housing body 110.

The channels 126 are equally spaced around the circumference, except that the spacing between the shortest channel 126a and the longest channel 126b is increased to define a proximally-directed surface or land 130 on each side of the front housing body 110. A stop rib 132 extends proximally from one side the land 130, adjacent to the longest channel 126b.

A detent ring 134 is disposed adjacent to the proximal ends of the channels 126, at the proximal end of the front housing body 110. A plurality of V-shaped indents 136 are arranged around one half of the detent ring 134, with one indent 136 being provided for each opposite pair of channels 126. The spacing of the indents 136 corresponds to the spacing of the channels 126. A cut-out is provided in the proximal end of the front housing body 110 to form an indicator window 138 adjacent to the detent ring 134.

Referring back to FIG. 4(a) and additionally to FIG. 10, the plunger 300 comprises a tubular plunger rod 304 and a can-shaped plunger body 306. The plunger body 306 is closed at its proximal end by an end plate 308 to which the plunger rod 304 is attached. The priming pin 302 (not shown in FIG. 10) is received in the bore of the plunger rod 304. As best shown in FIGS. 4(a) and 4(b), the distal end of the plunger rod 304 includes a recess 305 for receiving a contact disc 307 formed at the distal end of the priming pin 302.

The plunger body 306 extends distally from the end plate 308 to act as a guide for the drive spring 330. The plunger body 306 has an external flange that provides a spring seat 310 for the distal end of the drive spring 330. The spring seat 310 is provided with a proximally-extending outside rim 312 having four extended parts 314 that help to retain the drive spring 330 on the spring seat 310.

As shown most clearly in FIG. 10, a pair of plunger guide formations 316, in the form of longitudinally-extending ribs, are disposed diametrically opposite to one another on the rim 312 of the spring seat 310. The guide formations 316 are arranged to cooperate with the channels 126 in the front housing body 110, as will be explained in more detail below.

A distal end part of the plunger body 306 projects beyond the spring seat 310. A feedback projection or tab 318 is disposed on the outer surface of the distal end part for engagement with the feedback component 380 upon operation of the device 100, as will be described below.

Two proximally-projecting latching arms 320 are attached to the end plate 308 of the plunger 300. An inwardly-facing clip formation 322 is provided at the proximal end of each latching arm 320. Each clip formation 322 has a ramped proximal face 323 and a distal face 324 that is substantially perpendicular to the axis of the device 100. Two arcuate slots 326 are formed at the peripheral edge of the end plate 308 adjacent to the latching arms 320. The slots 326 are shaped to allow the interlock fingers 270 of the interlock component 250 to pass through the slots 326 to extend towards the trigger button 200.

Referring to FIGS. 4 and 11, the trigger button 200 comprises a button chassis 202 having a proximal end face 204 (see FIG. 4, not shown in FIG. 11) and a distally-extending, generally tubular skirt 206.

A pair of retaining arms 208 extend distally from the chassis 202. Each retaining arm 208 is provided with an outwardly-facing clip formation 210 at its distal end, and the retaining arms 208 are arranged diametrically opposite one another on the chassis 202. A pair of latch release pins 212 also extend distally from the chassis 202. The latch release pins 212 are arcuate in cross-section and are arranged diametrically opposite one another and at right angles to the retaining arms 208.

As shown most clearly in FIG. 11, four locking fingers 214 also extend distally from the chassis 202. Each locking finger 214 is thickened at its distal end to define a generally V-shaped tip part 215 that protrudes radially outwards from the remaining part of the locking finger 214. The tip part 215 has a ramped distal surface 216 and a ramped proximal surface 217, with the proximal surface 217 being at a steeper inclined angle than the distal surface 216. A longitudinally-extending rib 218 is disposed along one side of the distal surface 213 of each tip part 215. Each locking finger 214 is disposed between respective ones of the retaining arms 208 and the latch release pins 212, with the rib 218 on the distal surface 216 of the tip part 215 on the side closest to the respective latch release pin 212.

Referring to FIGS. 4 and 12, the rear housing body 140 is generally tubular and includes an internal flange 144 that acts as a spring seat for the proximal end of the drive spring 330. The flange carries a pair of clip supports 146 to cooperate with the clip formations 210 of the retaining arms 208 to retain the button 200 in the distal end 142 of the rear housing body 140, as best seen in FIG. 4(a).

Proximal to the flange 144, a bridge part 148 extends across the bore of the rear housing body 140. The bridge part 148 is attached to the flange 144 by way of a pair of upstanding arcuate guide walls 150, shown most clearly in FIG. 4(b). Each guide wall 150 is provided with a circumferentially-extending projection or control rib 152 on its inside surface, and a pair of parallel ribs on its outside surface to define a guide channel 153 for a corresponding guide rib 207 formed on the inside of the skirt 206 of the trigger button 200.

Arcuate slots 154 are formed in the bridge part 148 adjacent to the inside surface of each guide wall 150 to accept the interlock fingers 170 of the interlock component 170 and the latching arms 320 of the plunger 300. At each end of each slot 154, a guide ramp 156 is provided. The guide ramps 156 extend proximally from the bridge part 148, and each guide ramp 156 has a ramped inside face 158 and a proximal end face 160 that lies perpendicular to the axis of the device 100. The proximal side of the bridge part 148 is provided with two raised contact pads 162 disposed adjacent to the inside edge of each slot 154. As shown in FIGS. 4(a) and 4(b), the distal side of the bridge part 148 is provided with a tubular socket 164 for engagement with the proximal end of the priming pin 302.

FIG. 13 shows the feedback component 380 of the device. The feedback component 380 is generally tubular, and the proximal end of the feedback component 380 is shaped to define two stepped helical forms 382, with the adjacent steps 384 of the helical forms 382 having the same axial spacing as the distal ends 128 of the corresponding channels 126 in the front housing body 110.

The feedback component 380 is provided with a pair of clip arms 384 disposed on opposite sides of the feedback component 380. Each clip arm 384 is attached to the feedback component 380 at its distal end and has an outwardly-facing clip formation 386 at its proximal end. Each clip formation 386 has a ramped distal face 387 and a proximal face 388 that lies perpendicular to the axis of the device 100. Distal to each clip arm 384, the outer surface of the feedback component 380 is provided with a pair of retaining ribs 390, 391 that are spaced apart in the axial direction.

Referring back to FIGS. 4(a) and 4(b), in an initial state of the device, the cap 180 is in place to close the distal end 112 of the front housing body 110, with the key 194 of the cap 180 engaged with the keyway 117 to lock the cap 180 to the front housing body 110.

The shield retainer arms 188 embrace the needle shield 30 and the clip formations 190 of the retainer arms 188 are clipped to the proximal end of the needle shield 30. The shuttle member 280 is supported by the proximal ends of the retainer arms 188, with the carrier tabs 286 projecting between the shoulder 18 of the syringe body 12 and the proximal end of the needle shield 30.

The clip formation 266 of the sleeve part 258 of the interlock component 250 is engaged with the support tabs 125 of the front housing body 110, so that the interlock component 250 is held in a first position with respect to the front housing body 110, in which the distal end face 262 of the needle shroud 260 projects beyond the distal end face 112 of the front housing body 110.

The plunger 300 is retained in a starting position by engagement of the clip formations 322 of the latching arms 320 with the bridge portion 148 of the rear housing body 140. The drive spring 330 is compressed between the spring seat 310 of the plunger 300 and the flange 144 of the rear housing body. When the plunger 300 is in its starting position, the priming pin 302 is received in the socket 164 of the bridge part 148 of the rear housing body. The length of the priming pin 302 is such that the contact disc 307 of the priming pin 302 is disposed distally with respect to the distal end of the plunger rod 304.

The feedback component 380 is retained in a stowed position in the device 100 by engagement of the retaining ribs 390, 391 with the front housing body 110. The distal retaining rib 391 engages with a proximal end of the window 114, and the proximal retaining rib 390 engages with an internal step in the front housing body 110, adjacent to the external step 120.

The carrier assembly 220 is locked in an initial axial position by a carrier lock arrangement. Referring to FIG. 14, which is an enlarged view of the carrier lock arrangement, in the initial state of the device 100, each of the guide legs 232 of the carrier support 222 is positioned adjacent to one of the collars 124 of the support arms 122 of the front housing body 110. On each guide leg 232, the proximal face 241 of the blocking projection 240 abuts a distal side of the collar 124 to prevent proximal movement of the carrier assembly 220 relative to the front housing body 110. Similarly, the distal face 246 of the lock projection 244 engages with the proximal side of the collar 124 to prevent distal movement of the carrier assembly 220 relative to the front housing body 110. In this way, the collar 124 provides a locking formation of the carrier lock arrangement.

To ensure that the guide legs 232 cannot deflect inwardly to allow the lock projection 244 to move past the collar 124, the interlock component 250 braces the guide legs 232, as follows. With the interlock component 250 in its first position, as in the initial state of the device, the tabs 256 provided on the sides of the guide arms 252 of the interlock component 250 are positioned to bear against the rails 247 of the guide legs 232. The interaction between the tabs 256 and the rails 247 serves to brace the guide legs 232 against deflection and to wedge each leg 232 against the respective collar 124, so that the tabs 256 act as bracing formations.

In the initial state of the device, the cap 180 is locked to the front housing body 110 by virtue of the engagement between the key 194 of the cap 180 and the keyway 117 of the front housing body 110. To prepare the device 100 for use, the cap 180 must be removed. As shown in FIG. 9(b), the key 194 is initially positioned at the end of the circumferentially-extending part 117a of the keyway 117 furthest from the longitudinally-extending part 117b. The cap 180 must therefore be turned with respect to the front housing body 110 from its first, initial position to a second position to bring the key 194 into alignment with the longitudinally-extending part 117b to unlock the cap 180 for axial movement with respect to the front housing body 110.

Unlocking of the cap 180 operates the priming mechanism of the device 100, in which the shuttle member 280 moves the syringe body 12 in the proximal direction with respect to the front housing body 110.

Referring to FIG. 15, which shows an enlarged view of part of the device 100 with the syringe 10 omitted for clarity, the ramp formations 192 at the ends of the retainer arms 188 of the shield retainer 186 of the cap 180 are initially disposed between the ribs 284 of the shuttle member 280. When the cap 180 is turned, the ramp formations 192 come into contact with and bear against the ends of the ribs 284, in the manner of a cam and follower. The shuttle member 280 cannot rotate due to the engagement of the guide tabs 282 of the shuttle member 280 with the corresponding guide slots 264 of the interlock component 250. Accordingly, the shuttle member 280 is forced to move in the proximal direction with respect to the front housing body 110. The carrier tabs 286 act upon the shoulder 18 of the syringe 10 (not shown in FIG. 15), so that the syringe body 12 moves proximally along with the shuttle member 280.

Movement of the syringe in the proximal direction has several effects, as will now be explained with reference to FIGS. 16 and 17, which show enlarged views of parts of the device 100 before and after operation of the priming mechanism, respectively.

As shown in FIG. 16(*a*), before operation of the priming mechanism, the needle shield 30 of the syringe 10 is attached to the distal end syringe body 12 to seal the needle (not visible in FIG. 16(*a*)). The needle shield 30 is retained by the retainer arms 188 of the cap 180. Therefore the axial position of the syringe 10 in the device 100 is fixed by the shield retainer 186 of the cap 180. Both the clip formations 184 of the retainer arms 188 and the carrier tabs 286 (not visible in FIG. 16(*a*), see FIG. 15) of the shuttle member 280 project inwardly between the distal end of the needle shield 30 and the shoulder 18 of the syringe body 12.

Referring to FIG. 16(*b*), when in this initial position, the stopper 22 of the syringe 10 is spaced apart from the distal end of the plunger rod 304 and the contact disc 307 of the priming pin 302 (the priming pin 302 is not visible in FIG. 16(*b*)).

Turning to FIG. 17(*a*), during operation of the priming mechanism, the shuttle member 280 moves proximally with respect to the front housing body 110. The carrier tabs 286 (not visible in FIG. 17(*a*), see FIG. 15) act against the shoulder 18 of the syringe body 12 to move the syringe body 12 in the proximal direction to a starting position. The needle shield 30 is retained by the retainer arms 188 of the shield retainer 186, so that the syringe 10 is released from the needle shield 30.

Proximal movement of the syringe body 12 also causes the stopper 22 to move against the contact disc 307 of the priming pin 302, as shown in FIG. 17(*b*). The priming pin 302 prevents further proximal movement of the stopper 22, so that the stopper 22 moves relative to the syringe body 12 upon continued proximal movement of the syringe body 12. This has the effect of ejecting a small quantity of medicament from the syringe 10, and of moving the stopper 22 to a pre-determined primed position relative to the shoulder 18.

Advantageously, movement of the stopper 22 from its initial position to the known, primed position ensures that the quantity of medicament injected upon subsequent activation of the drive mechanism of the device 100 is not dependent on the initial position of the stopper 22 after manufacture of the syringe 20, thereby increasing the accuracy of the dose delivered.

Proximal movement of the syringe body 12 to its starting position also causes the flange 24 of the syringe 10 to become spaced from the damping element 226 of the sleeve 224 of the carrier assembly 220. This ensures that, upon subsequent activation of the drive mechanism, the syringe body 12 will move in the distal direction with respect to the carrier assembly 220 during a final part of an insertion stroke of the syringe 10, as will be discussed further below.

Referring back to FIG. 9(*b*), once the cap 180 has been turned to bring the key 194 into register with the longitudinally-extending part 117*b* of the keyway 117, the cap 180 can be pulled in the distal direction relative to the front housing body 110 to remove the cap 180 and the needle shield 30 from the device 100.

FIGS. 18(*a*) and 18(*b*) show the primed device after removal of the cap 180. The syringe 10 is held in its starting position by the locked carrier assembly 220, with the needle 16 of the syringe 10 retracted in the front housing body 110 (i.e. the distal end of the needle 16 is spaced proximally from the distal end 112 of the front housing body 110). The interlock component 250 is in its first position, with the distal end face 262 of the needle shroud 260 spaced distally from the distal end 112 of the front housing body 110. The interlock spring 221 acts to bias the interlock component 250 to return to its first position in the event that the interlock distal end face 262 of the needle shroud 260 is displaced towards the front housing body 110.

The next stage in operation of the device 100 is to set the dosage to be delivered. Referring to FIG. 19, the rear housing body 140 acts as a dose selector for the device 100. To this end, the rear housing body 140 is rotatable with respect to the front housing body 110 (shown in a transparent rendering in FIG. 19), and is marked with indicia to indicate the selected dose in the window 138 of the front housing body 110. The plunger 300 and the interlock component 250 are coupled to rotate with the rear housing body 140, as a result of the engagement between the plunger latch arms 320 with the bridge part 148 of the rear housing body 140, and the engagement of the interlock fingers 170 with the arcuate slots 154 in the bridge part 148.

FIG. 19(*a*) shows the device 100 before selection of a dose. In this state, a "0" indicia is displayed in the window 138, and each of the plunger guide formations 316 (only one of which is shown in FIG. 19(*a*)) is aligned with the respective land 130 on the inner surface of the front housing body 110. Engagement between the guide formations 316 and the lands 130 prevents movement of the plunger 300 in the distal direction, so that the device 100 can only be fired once a dose has been selected. The stop rib 132 prevents rotation of the rear housing body 140 in the anticlockwise direction (viewed towards the proximal end of the device), either by a user or as a result of rotation of the cap 180 during removal of the cap 180.

To select a dose, the rear housing body 140 is rotated with respect to the front housing body 110, as shown in FIG. 19(*b*), to bring the guide formations 316 into line with the appropriate pair of channels 126 of the front housing body 110, thereby to set the stroke length of the plunger 300. A detent member 166 is provided for engagement with the grooves 136 in the detent ring 134 to provide a tactile indication that the guide formations 316 are correctly aligned with a pair of channels 126, and the indicia corresponding to the selected dose is displayed in the window 138.

It will be appreciated that the dose could instead be selected before removal of the cap 180. In this case, the rear housing body 140 acts as the operating member for the priming mechanism. Referring back to FIG. 15, if the rear housing body 140 is turned to select a dose with the cap 180 still in place, the resulting turning movement of the interlock component 250 about the device axis causes the shuttle member 280 to turn with respect to the retainer arms 188, driving the ribs 284 of the shuttle member 280 against the ramp formations 192 of the retainer arms 188 and causing proximal movement of the shuttle member 280 and priming movement of the syringe 10. The direction of rotation of the rear housing body 140 during dose selection is in the opposite sense to the direction that the cap 180 must be turned to unlock the cap 180, so the cap remains stationary when the rear housing body 140 is turned. In the event that the rear housing body 140 is not turned sufficiently to move the syringe body 12 all the way to its starting position, the remaining movement of the syringe body 12 to its starting position will take place with the cap 180 is subsequently removed.

In any event, once the cap 180 has been removed and the dose has been selected, the distal end of the device 100 can be placed against an injection site ready for injection. To prevent accidental operation of the device 100 before the device has been placed against the injection site, a locking mechanism for the trigger button is provided, as will now be explained with reference to FIGS. 20 to 22.

FIGS. 20(a) and 21(a) are enlarged views of the proximal end of the device 100 when the interlock component 250 is in its first position (as shown in FIG. 18). The clip formations 322 of the latching arms 320 of the plunger 300 are engaged with the bridge part 148 of the rear housing body 140, with the distal faces 324 of the clip formations 322 against the contact pads 162 of the bridge part 148. In this way, the plunger 300 is latched in its starting position against the biasing force of the drive spring 330. The proximal ends of the interlock fingers 270 are positioned adjacent to the clip formations 322 of the latching arms 320, so that the support pads 274 of the interlock fingers 270 contact the latching arms 320 to keep the clip formations 322 engaged with the bridge part 148.

As seen most clearly in FIG. 21(a), the proximal end faces 271 of the interlock fingers 270 are spaced distally from the locking fingers 214 of the trigger button 200. In this state, the trigger button 200 is in a stowed position with respect to the rear housing body 140. The trigger button 200 is retained in the stowed position by engagement of the tip part 215 of each locking finger 214 with the distal side of the control rib 152 of the respective guide wall 150 of the rear housing body 140. Depression of the trigger button 200 in the distal direction is not possible because the distal ends of the locking fingers 214 abut the proximal end faces 160 of the guide ramps 156 of the rear housing body 140. In this way, the proximal end faces 160 of the guide ramps 156 act as stop faces for the locking fingers 214. The ribs 218 (not visible in FIGS. 20 and 21) on the locking fingers 214 provide an increased contact area at the distal end of each locking finger 214.

Referring back to FIG. 18, to unlock the trigger button 200, the device 100 is pressed against the injection site, which causes the interlock component 250 to move proximally with respect to the front housing body 110 to a second position, in which the distal end face 262 of the needle shroud 260 is approximately aligned with the distal end 112 of the front housing body 110. FIGS. 20(b), 21(b) and 22(a) show the proximal end of the device 100 when the interlock component 250 has been moved to its second position.

As the interlock component 250 moves towards its second position, the proximal end faces 271 of the interlock fingers 270 contact the distal ends of the locking fingers 214. Further proximal movement of the interlock component 250 pushes the locking fingers 214, and therefore the trigger button 200, in the proximal direction. As shown most clearly in FIG. 21(b), the ramped proximal surfaces 217 of the tip parts 215 are therefore caused to ride over the control rib 152 on the respective guide wall 150, bending the locking fingers 214 inwardly.

As a result, the distal ends of the locking fingers 214 move radially inwards with respect to the proximal end faces 160 of the guide ramps 156. At the same time, the trigger button 200 moves proximally to a working position. This proximal movement of the trigger button 200 from the stowed position to the working position provides a visual indication to the user that the trigger button 200 has been unlocked and that the device 100 is ready for injection. In some variants of the invention, however, the trigger button 200 is initially in the working position and does not move proximally upon movement of the interlock component 250. For example, the control rib 152 may be omitted and the distal ends of the locking fingers 214 may be shaped to wedge behind the locking fingers 214 to bend the locking fingers 214 inwardly to clear the proximal faces 160 of the guide ramps 156.

As shown in FIG. 22(a), when the interlock component 250 is in the second position, the interlock fingers 170 have moved proximally with respect to the latch arms 320, so that the support pads 274 of the interlock fingers 270 are now clear of the clip formations 322 and the clip formations 322 are adjacent to the apertures 272 in the interlock fingers 270.

Because the locking fingers 214 have been bent inwardly by the control rib 152, the distal ends of the locking fingers 214 now clear the proximal end faces 160 of the guide ramps 156, so that distal movement of the firing button 200 with respect to the rear housing body is no longer blocked.

It is now possible for the user to depress the trigger button 200 to displace the button 200 in the distal direction from the working position to a firing position, as shown in FIG. 22(b). As the trigger button 200 moves distally, the latch release pins 212 bear against the ramped proximal faces 323 of the clip formations 322 of the latching arms 320. This causes the latching arms 320 to splay outwardly into the apertures 272 of the interlock fingers 270, allowing the distal faces 324 of the clip formations 322 to clear the bridge part 148 of the rear housing body 140. The plunger 300 can then move distally under the influence of the drive spring 330.

Although not shown in FIG. 22(b), as the firing button 200 is moved distally towards its firing position, the ramped distal surfaces 216 of the locking fingers 214 ride against the ramped inside faces 158 of the guide ramps 156, causing further bending of the locking fingers 214 as the trigger button 200 is moved to its fired position.

Movement of the interlock component 250 into its second position also serves to unlock the carrier lock arrangement. Referring back to FIG. 14, when the interlock component 250 moves in the proximal direction, the tabs 256 move off the rails 247 and into the clearance provided by the notches 248 in the guide legs 232 of the carrier assembly 220. In this way, the guide legs 232 are no longer braced and, upon application of a sufficient force to the carrier assembly 220, the guide legs 232 can deflect inwardly to allow the lock projections 244 to pass the collar 124. Interaction between the ramped distal face 246 of each lock projection 244 with the proximal inner edge of the collar 124 helps to deflect the legs 232.

Referring back to FIG. 18, once the firing button 200 has been depressed to release the plunger 300, the plunger begins to move distally. The recess 305 at the distal end of the plunger rod 304 engages with the contact disc 307 of the firing pin 302 to couple the firing pin 302 to the plunger rod 304. The proximal end of the firing pin 302 disengages from the socket 164 on the bridge part 148 so that the firing pin 302 can be carried distally with the plunger 300 for the remainder of the plunger stroke.

The distal end of the plunger rod 304 transfers the force of the drive spring 330 to the stopper 22 of the syringe 10. Initially, as a result of the friction between the stopper 22 and the syringe body 12 and the fluid flow resistance through the needle 16, the syringe body 12 moves together with the stopper 22 to displace the syringe body 12 distally from its starting position to begin an insertion stroke of the syringe 10.

A distal force is also applied to the carrier assembly 220 by the syringe body 12, as a result of the frictional gripping force applied to the syringe body 12 by the carrier sleeve 224. This distal force is sufficient to allow the lock projections 244 to pass the collar 124 as described above. The carrier assembly 220 therefore moves distally, together with the syringe 10, until the carrier assembly 220 reaches a stop position.

FIG. 23 shows the device 100 at the point during the insertion stroke when the carrier assembly 220 has reached the stop position, in which the distally-directed faces of the stop projections 242 on each guide leg 232 abut the proximal sides of the collars 124 on the support arms 122 of the front housing body 110 (see FIG. 23(b)). In this way, the collars 124 provide stops that define the stop position of the carrier assembly 220. At this point, the needle 16 is starting to protrude from the distal end 112 of the front housing body 112 to pierce the injection site. During distal movement of the carrier assembly 220, the latch members 236 (see FIG. 5, not shown in FIG. 23) on the guide legs 232 bend inwardly as the ramped faces 238 pass over the collars 124, allowing the latch members 236 to pass the collars 124. Distal movement of the carrier assembly 220 also compresses the interlock spring 221 against the flange 265 of the interlock component 250.

After the carrier assembly 220 has reached the stop position, further distal movement of the plunger 300 causes movement of the syringe body 12 in the distal direction with respect to the carrier assembly 220. Distal movement of the syringe body 12 relative to the carrier assembly 220 and the front housing body 110 continues until the flange 24 of the syringe 10 abuts the damping element 226 of the sleeve 224 of the carrier assembly 220, as shown in FIG. 24. At this point, the syringe 10 has reached its final insertion position at the end of the insertion stroke and the needle 16 has been advanced to its full penetration depth.

FIGS. 25(a) and 25(b) are enlarged views of the device 100 illustrating the final part of the insertion stroke in more detail. In FIG. 25(a), which corresponds to FIG. 23, the carrier assembly 220 is in the stop position but the flange 24 of the syringe 10 is still spaced from the damping element 226.

As the insertion stroke continues, the syringe body 12 moves distally with respect to the carrier assembly 220 by a distance D, to bring the flange 24 of the syringe 10 into contact with the damping element 226, as shown in FIG. 25(b).

Advantageously, when the syringe body 12 moves relative to the carrier assembly 220, the sleeve 224 of the carrier assembly 220 acts to reduce the velocity of the syringe 10 before the flange 24 contacts the damping element 226. This is because the sleeve 224, and in particular the annular rib 230 of the bore 225 of the sleeve 224, applies a frictional retardation force to the syringe body 12 that retards the movement the syringe 10 against the influence of the insertion force. As a result, the momentum of the syringe 10 is reduced before the flange 24 contacts the damping element 226, to reduce the impact forces experienced by the syringe 10 and the device 100 at the end of the insertion stroke. Once the flange 24 contacts the damping element 226, the damping element 226 deforms to help absorb some of the impact energy, further reducing the risk of damage to the syringe 10 and the device 100.

Once the syringe 10 has reached the insertion position, the stopper 22 is moved distally by the plunger rod 304 in a medicament delivery stroke to eject medicament through the needle 16 for injection. FIG. 26 shows the device 100 part-way through the medicament delivery stroke, with the stopper 22 travelling towards the needle 16. As shown in more detail in FIG. 27, at this point, the feedback tab 318 of the plunger 300 contacts one of the steps 384 of the feedback component 380, thereby to unlatch the feedback component 380 from the front housing body 110 and to displace the feedback component 380 in the distal direction. This brings the feedback component 380 into view in the window 114 of the front housing body 110. The step 384 that engages with the feedback tab 318 is determined by the angular position of the feedback tab 318, which in turn corresponds to the dose set before activation of the device 100. The steps 384 are arranged so that the feedback component 380 is moved through the same axial distance by the plunger 300 irrespective of the stroke of the plunger 300, which is determined by the position of the distal end of the selected channel 126.

Once the plunger guide formations 316 reach the distal ends 128 of the selected channels 126, axial movement of the plunger 300 stops and the delivery stroke ends.

To avoid proximal movement of the syringe 10, which could push the stopper 22 against the plunger rod 304 and cause an overdose of medicament, the carrier assembly 220 is arranged to lock in its stop position. As shown in FIG. 28, when the syringe carrier 220 reaches the stop position, with the distal face 243 of each stop projection 242 abutting the proximal side of the respective collar 124, the corresponding latch member 236 is disposed on a distal side of the collar 124 and the blocking face 239 of the latch member 236 can cooperate with the collar 124 to stop proximal movement of the carrier assembly 220.

FIG. 29 shows the device 100 in an end-of-dose condition, at the end of the delivery stroke. The plunger 300 has reached the distal extent of its travel, defined by the plunger guide formations 316 reaching the distal ends 128 of the selected channels 126. As can be seen, not all of the medicament in the syringe 10 has been injected, but instead the stopper 22 has been driven distally to deliver the selected dose of medicament.

As seen most clearly in FIG. 29(a), in the end-of-dose state, the feedback component 380 has moved to block the window 114 in the front housing body 110, giving the user a visual indication of the end of dose. In addition, as the feedback component 380 moves into position, the clip formation 386 is first deflected by engagement of its ramped distal face 387 (see FIG. 13) with the front housing body 110, and then snaps into the window 114, providing an audible click or snap to give an audible end-of-dose indication. The proximal face 388 of the feedback component 380 engages with the edge of the window 114 to prevent subsequent proximal movement of the feedback component 380.

After the end-of-dose indications have occurred, the user can remove the device 100 from the injection site by moving the device 100 in the proximal direction to withdraw the needle 16. As the distal end 112 of the front housing body 110 moves away from the injection site, the interlock component 250 moves in the distal direction, under the influence of the interlock spring 221, to keep the distal end face 262 of the needle shroud 260 in contact with the injection site.

Distal movement of the interlock component 250 relative to the front housing body 110 continues until the ring part 254 of the interlock component 250 fouls the support arms 122 of the front housing body 110, as shown in FIG. 30. In this state, the needle shroud 260 is fully deployed such that the distal end of the needle 16 is proximal with respect to the distal end face 262 of the needle shroud 260.

To avoid proximal movement of the interlock component 250, which could otherwise expose the needle 16, the interlock component 250 locks into the fully-deployed position under the influence of the interlock spring 221. As shown most clearly in FIG. 31, the interlock spring 221 pushes the ramped distal face 267 of the clip formation 266 of the interlock component 250 over the support tabs 125 of the front housing body 110 to locate the clip formation 266 on the distal side of the tabs 125. Proximal movement of the interlock component 250 is then prevented by abutment of the proximal face 268 of the clip formation 266 with the distal side of the tabs 125.

With the device 100 in the locked-out state, shown in FIG. 30, the needle 16 is shrouded by the needle shroud 260 to prevent needle stick injuries. The plunger 300 is retained in its most distal position, with the plunger guide formations 316 against the distal ends 128 of the selected channels 126, under the residual force applied to the plunger 300 by the expanded drive spring 330. The feedback component 380, the interlock component 250 and the carrier assembly 330 are all locked in their respective final positions, as described above. With the device components in these locked-out positions, the device 100 can no longer be used, and can be safely disposed of.

The exemplary device 100 described with reference to FIGS. 1 to 31 features several mechanisms and arrangements for improved functionality, safety and user experience, including (but not limited to) the carrier lock arrangement described with reference to FIG. 14, the priming mechanism described with reference to FIGS. 15 to 17, the dose selector described with reference to FIG. 19, the trigger button locking mechanism described with reference to FIGS. 20 to 22, retardation of the movement of the syringe by the carrier assembly as described with reference to FIG. 25, operation of the feedback component described with reference to FIG. 27, locking of the carrier assembly in the stop position as described with reference to FIG. 28, and locking of the interlock component to shroud the needle as described with reference to FIG. 31. It will however be appreciated that each of these features could be used alone or in suitable combinations in other injection devices and/or auto-injectors as may be appropriate for a particular device design or intended use.

By way of example, a device 500 according to a second embodiment of the invention will now be described with reference to FIGS. 32 to 45. The device 500 is generally similar to the device 100 of the first embodiment of the invention, and only the differences will be described in detail. Notably, the device 500 of FIGS. 32 to 45 does not include a priming mechanism, but instead is provided with a syringe clamping arrangement. The device 500 also includes an alternative trigger button locking mechanism and plunger latch arrangement.

Referring first to FIGS. 32 to 34, as in the first embodiment of the invention, the device 500 of the second embodiment includes a generally elongate two-part housing comprising a generally tubular front housing body 510, a generally tubular rear housing body 540 rotatably attached to the proximal end of the front housing body 510, and a cap 580 that closes the distal end 512 of the front housing body 510 in an initial state of the device. A trigger component in the form of a trigger button 600 is retained in the proximal end 542 of the rear housing body 540.

The front housing body 510 houses a pre-filled syringe 10 having a needle shield 30. The body 12 of the syringe 10 is received in a carrier assembly 620. As in the first embodiment, in this second embodiment the carrier assembly 620 is guided for axial movement within the front housing body 510 by an interlock component 650, which is arranged concentrically around the carrier assembly 620. An interlock spring 621 acts to bias the carrier assembly 620 and the interlock component 650 apart. In the initial state of the device 500, illustrated in FIGS. 32 and 34, the interlock component 650 is in a first position, in which the distal end face 662 of needle shroud 660 of the interlock component 650 is disposed distally with respect to the distal end 512 of the front housing body 510.

As in the first embodiment, the interlock component 250 can be moved proximally to a second position to prepare the device for operation. The carrier assembly 620 and the interlock component 650 of the device 500 of the second embodiment are shown in isolation in FIGS. 35 and 36, respectively, and will be described in more detail below.

The rear housing body 540 houses the latch arrangement for the plunger 700 and the interlock mechanism for the trigger button 600. A drive spring 730 acts between the rear housing body 540 and the plunger 700 to bias the plunger 700 in the distal direction, and a feedback component 780 is cooperable with the plunger 700 to provide an end-of-dose indication. The plunger 700, the interlock button 600 and the rear housing body 540 are shown in isolation in FIGS. 39, 40 and 41 respectively, and will be described in more detail below.

The components of the device 500 are generally similar to the corresponding components of the device 100 of the first embodiment and cooperate in similar ways during operation. As noted above, however, the device 500 of the second embodiment of the invention does not include a priming mechanism. Accordingly, as best seen in FIG. 34(*b*), the shield retainer arms 588 of the deshielder cap 580 do not have ramp formations at their distal ends, and no shuttle member is present. To remove the cap 580 from the device 500, the cap 580 can be simply pulled axially in the distal direction with respect to the front housing body 510, such that the shield retainer arms 588 apply a deshielding force to remove the needle shield 30 from the syringe 10.

It is however still desirable to ensure that the syringe 10 is positioned in a starting position with the flange 24 of the syringe 10 spaced from the proximal end of the carrier assembly 620 before operation of the device 500. As in the first embodiment, with the syringe 10 positioned in this way before operation of the device 500, relative movement of the syringe 10 with respect to the carrier assembly 620 during the final part of the insertion stroke of the syringe 10 causes retardation of the movement of the syringe 10 due to the frictional retardation force applied to the syringe body 12 by the sleeve 624 of the carrier assembly 620.

Accordingly, in the device 500 of the second embodiment of the invention, the syringe 10 is positioned in its starting position during assembly of the device 500. To guard against movement of the syringe 10 out of the staring position before operation of the device 500, particularly during removal of the needle shield 30 by the cap 580, the carrier assembly 620 is modified to include clamping means arranged to apply a releasable clamping force to the syringe body 12, by way of the sleeve 624, to restrict axial movement of the syringe 10 with respect to the carrier assembly 620.

To this end, referring to FIG. 35, the carrier support 622 of the carrier assembly 620 is provided with three clamping members or legs 800. The clamping legs 800 are arcuate in cross-section and extend distally from the carrier support 622, between the guide legs 632.

The proximal end 802 of each clamping leg 800 is attached to the carrier support 622. A distal part 804 of each clamping leg 800 is free to move with respect to the fixed proximal end 802, so that the clamping legs 800 can flex or bend. The outer surface of the distal part 804 of each clamping leg 800 defines a control surface 806 of the clamping leg 800.

As seen most clearly in FIG. 35(a), an elongate recess or channel 808 extends from the carrier support 622 along each clamping leg 800 towards the respective distal part 804. Each channel 808 stops short of the distal end of the respective clamping leg 800, to leave the control surface 806 uninterrupted by the channel 808.

Referring again to FIG. 35(b), the sleeve 624 of the carrier assembly 620 is extended proximally along the inside surface of each clamping leg 800. A deformable projection or rib 630 is provided on the internal surface of each of the extended parts of the sleeve 624, adjacent to the distal part 804 of the respective clamping leg 800. The three ribs 630, taken together, describe an annular form around the sleeve 624.

Each of the control surfaces 806 of the clamping legs 800 cooperate with a corresponding control element provided on the interlock component 650. Referring to FIG. 36, each control element comprises a protuberance or rib 810 provided at the proximal end of each of the guide arms 652 of the interlock component 650, adjacent to the ring part 654.

FIG. 37 shows the interaction between one of the guide arms 652 of the interlock component 650 with one of the clamping legs 800 of the carrier assembly 620 when the interlock component 650 is in its first position. In this state, each of the ribs 810 on the guide arms 265 of the interlock component 650 presses against the control surface 806 of the respective clamping arm 800 of the carrier assembly 620. The clamping arms 800 therefore apply a clamping force to the elastomeric sleeve 624 of the carrier assembly 620, pressing the sleeve 624 and the rib 630 against the syringe body 12 to restrict axial movement of the syringe 10 with respect to the carrier assembly 620.

As in the first embodiment of the invention, in this second embodiment the interlock component 650 also cooperates with the guide legs 624 of the carrier assembly 620 to lock the carrier assembly 620 in its initial position with respect to the front housing body 510 when the interlock component 650 is in its first position. In this way, when the interlock component 650 is in the first position, movement of the syringe 10 with respect to the front housing body 510 is prevented by a combination of two features, namely the carrier lock arrangement which locks the carrier assembly 620 relative to the front housing body 510, and the clamping mechanism described above with reference to FIG. 37.

Upon removal of the cap 580, the syringe 10 therefore remains fixed in its starting position, with the flange 24 of the syringe body 12 spaced from the damping element 626 at the proximal end of the carrier assembly 620. FIG. 38 shows the device 500 with the cap 580 removed, and the interlock component 650 still in the first position. The dose of medicament to be delivered can be selected at this stage, by rotating the rear housing body 540 with respect to the front housing body 510 as described above with reference to the first embodiment of the invention.

To allow the device 500 to be fired, the carrier assembly 620 must be released from its locked state to allow the syringe 10 and the carrier assembly 620 to move distally during the insertion stroke. Also, the clamping force applied by the clamping legs 800 must be removed, to allow the syringe 10 to move distally with respect to the carrier assembly 620 at the end of the insertion stroke, after the carrier assembly 620 has reached its stop position. Release of the carrier lock mechanism and removal of the clamping force are both achieved by movement of the interlock component 650 towards its second position when the device 500 is pressed against the injection site, moving the distal end face 662 of the needle shroud 660 proximally with respect to the front housing body 510.

Referring back to FIG. 37, when the interlock component 650 moves in the proximal direction towards its second position, the rib 810 on each guide arm 652 of the interlock component 250 slides along the control surface 806 and then into the clearance provided by the channel 808 on the proximal side of the control face 806. This movement disengages the rib 810 from the control surface 806 and removes the clamping force on the clamping leg 800, thereby switching the clamping leg 800 from its clamped state to an unclamped state.

It will be appreciated that, although a clamping force is no longer applied to the sleeve 624 by the clamping leg 800 under the influence of the rib 810, the syringe body 12 is still retained in position with respect to the carrier assembly 620 by the residual elastomeric clamping force that results from compression of the sleeve 624 between the syringe body 12 and the carrier support 622.

As in the first embodiment of the invention, movement of the interlock component 650 from the first state to the second state also unlocks the trigger button 600 to allow the trigger button to be moved to a firing position to release the plunger. As noted above, the device 500 of the second embodiment of the invention includes a modified locking mechanism for the trigger button 600, as will now be described.

Referring back to FIG. 36, in this embodiment, the interlock component 650 includes a pair of elongate interlock fingers 670 that project proximally from the ring part 654. Each interlock finger 670 terminates with a head part 674 having a proximal end face 671 with a chamfered outer side 673. Moving distally, the outer surface of the head part 674 is stepped inwardly to define a proximally-directed blocking face 675, and then outwardly to define a distally-directed ramp formation 677. The outer surface of each interlock finger 670 forms a guide surface 679 on the distal side of the ramp formation 677.

Turning to FIG. 39, in this second embodiment of the invention, the plunger 700 is modified to provide four latching arms 720 that project proximally from the end plate 708 of the plunger body 706. The latching arms 720 are arranged in diametrically-opposite pairs, with the adjacent latching arms 720 in each pair being spaced apart to accommodate the interlock fingers 670 of the interlock component 650 therebetween, as will be explained below.

An outwardly-facing clip formation 722 is provided at the proximal end of each latching arm 720. Each clip formation 722 has a ramped proximal face 723 and a distal face 724 that is substantially perpendicular to the axis of the device 500. A slot 726 is formed in the end plate 308 between each of the latching arms 720 in each pair of latching arms 720. The slots 726 allow the interlock fingers 670 of the interlock component 650 to pass through the slots 726 to extend towards the trigger button 600.

The plunger 700 is otherwise similar to the plunger 300 of the first embodiment of the invention, except that, in the second embodiment, the plunger rod 704 is solid and no priming pin is provided.

Referring to FIG. 40, the trigger button 600 in this second embodiment of the invention is simplified. A tubular latch release sleeve 612 extends distally from the button chassis 602. A pair of outwardly-directed clip formations 610 are provided at the distal end of the latch release sleeve 612, to clip the trigger button 600 to the rear housing body.

The rear housing body 540 is also of a simplified design in this second embodiment of the invention. As shown in FIG. 41, the rear housing body comprises an internal flange 544 that acts as a spring seat for the proximal end of the drive spring 730. A tubular guide wall 550 extends proximally from the flange 544, and a pair of diametrically-opposed apertures 546 are formed in the guide wall 550. The apertures 546 accept the clip formations 610 of the trigger button 600 so as to retain the button 600 in the distal end 542 of the rear housing body 540. A control collar 552 is disposed at the distal end of the guide wall 550. The control collar 552 has a reduced internal diameter compared to the guide wall 550. The proximal face of the control collar 552 provides a stop face 560 for the interlock fingers 670, as will now be explained.

Referring now to FIG. 42, when the device 500 in its initial state with the interlock component 650 is in its first position, the clip formations 722 of the latching arms 720 of the plunger 700 are engaged with the control collar 552. The distal faces 724 of each clip formation 722 abut the stop face 560 of the control collar 552, so that the plunger 700 is latched in its starting position.

The interlock fingers 670 extend between the adjacent latching arms 720 of each pair of latching arms 720, through the slots 726 in the plunger end plate 308, so that the head part 674 of each interlock finger 670 is located between the opposing side faces of the adjacent latching arms 720. With the head parts 674 in this position, inward flexing of the latching arms 720 cannot occur, so that the interlock fingers 670 help to prevent premature disengagement of the latching arms 720 from the control collar 552.

The interlock fingers 670 also engage with the control collar 552. The blocking face 675 of each interlock finger 670 abuts the stop face 560 of the control collar 552, which blocks distal movement of the interlock fingers 670 relative to the rear housing body 540. In turn, distal movement of the trigger button 600 is prevented, because the distal end of the release sleeve 612 of the trigger button 600 contacts the proximal end face 671 of each interlock finger 670.

Accordingly, distal movement of the trigger button 600 to its firing position is blocked when the interlock component 650 is in its first position.

When the device 500 is placed against the injection site, the interlock component 650 moves proximally with respect to the rear housing body 540, towards the second position. This causes the distally-facing ramp formations 677 of the interlock fingers 670 to ride over the distal edge of the control collar 552, which bends the distal parts of the interlock fingers 670 inwardly, moving the proximal end faces 671 away from the release sleeve 612 of the trigger button 200, with the chamfered outer sides 673 allowing the interlock fingers 670 to clear the release sleeve 612.

Initially, cooperation between the ramp formations 677 and the control collar 552 causes a relatively large amount of inward radial displacement of the end faces 671 of the interlock fingers 670. On continued proximal movement of the interlock fingers 670, the ramp formations 677 clear the control collar 552, and the distal edge of the control collar 552 instead cooperates with the guide surface 679 of each interlock finger 670. This results in further bending of the interlock fingers 670 as they move proximally with respect to the control collar 552.

FIGS. 43 and 44 show the proximal end of the device 500 when the interlock component 650 has moved to its second position, and FIG. 45 shows the whole device in the same condition (with only one of the interlock fingers 670 being visible in FIGS. 45(*a*) and 45(*b*)).

With the interlock fingers 670 bent inwardly, the blocking faces 675 of the interlock fingers 670 are now clear of the stop face 560 of the control collar 552, and are moved to a position in which the head parts 674 of the interlock fingers 670 no longer prevent inward flexing of the latching arms 720.

Accordingly, with the interlock component 650 in its second position, the trigger button 600 is unlocked for movement in the distal direction to its firing position. Distal movement of the trigger button 600 with respect to the rear housing body 540 causes the latch release sleeve 612 to bear against the ramped proximal face 723 of the clip formation 722 of each latching arm 720, bending the latching arms 720 radially inwardly. In this way, the distal face 724 of the clip formation 722 of each latching arm 720 moves to clear the stop face 560 of the control collar 552, allowing the plunger 700 to move distally under the influence of the drive spring 730.

As in the first embodiment of the invention, movement of the plunger 700 first causes an insertion stroke of the syringe 10, in which the syringe 10 and the carrier assembly 620 move together in the distal direction. The carrier assembly 620 then locks in its stop position, and in a final part of the insertion stroke the syringe 10 moves distally relative to the carrier assembly 620, causing a reduction in the acceleration of the syringe 10 until the flange 24 comes to a stop against the damping element 626 of the carrier assembly 620. The plunger 700 then moves the stopper 22 of the syringe 10 in the distal direction, to expel the desired quantity of medicament through the needle 16. At the same time, the plunger 700 deploys the feedback component 780. Once the plunger 700 reaches its stop position, the device 500 can be withdrawn from the injection site, causing distal movement of the interlock component 250 and deployment of the needle shroud 760 into its locked-out position.

It will again be appreciated that the various features of the device of the second embodiment of the invention could be used alone or in suitable combinations in other injection devices. For example, the trigger button locking mechanisms of the device of the second embodiment of the invention could be used with the device of the first embodiment of the invention, or vice versa.

In both of the above-described embodiments of the invention, it may be desirable to provide additional security against unintentional operation of the device. For example, in the above-described examples, movement of the trigger button 200, 600 is blocked when the interlock component 250 is in the first position, and the trigger button 200, 600 cannot be operated until the interlock component 250 has moved towards the second position. In normal use, the interlock spring 221 biases the interlock component into the first position, and when the cap 180, 580 is in place it is not possible for a user to apply the necessary force to the interlock component 250 to displace it to the second position. However, even when the cap 180, 580 is in place, movement of the interlock component 250 against the bias of the interlock spring 221 could still occur, for example if the device were to be dropped or otherwise subjected to a shock load. In particular, dropping of the device onto its proximal end may cause displacement of the interlock component 250 and allow the trigger button 200, 600 to move to the firing position, resulting in an unintentional firing of the device.

In some cases, sufficient protection against unintentional firing in such conditions can be provided by selection of a suitably stiff interlock spring 221. However, it can be preferable to use a relatively weak interlock spring 221, to minimise the force that must be applied to press the device against the injection site in use.

FIGS. 46(a) to (c) illustrate part of a variant of the device of FIGS. 1 to 31, in which a securing mechanism for preventing movement of the interlock component in the proximal direction is provided. The syringe and the carrier assembly are not shown in FIG. 46.

In this variant, the interlock component 250a is a two-part assembly, in which the distal ends of the guide arms 252a join with an annular upper sleeve part 258a that terminates at its distal end with a clip formation 258b. A lower sleeve part 258c of the interlock component 250a engages with the clip formation 258b. The upper and lower sleeve parts 258a, 258c together provide generally the same functionality as the single-piece interlock component 250 of the device of FIGS. 1 to 31. In FIGS. 46(a) and (b), the lower sleeve part 258c is omitted for clarity.

As in the device of FIGS. 1 to 31, the interlock component 250a of this variant is coupled to the rear housing body 140 (not shown in FIG. 46). However, in this case, turning movement of the rear housing body 140 to select a dose drives turning movement of the upper sleeve part 258a of the interlock component 250a with respect to the axis of the device, whilst the lower sleeve part 258c does not rotate. Thus in this variant, turning movement of the rear housing body 140 does not prime the device.

The interlock component 250a is provided with a pair of diametrically opposed securing projections 253 that are disposed on the outside surface of the upper sleeve part 258a. A corresponding pair of inwardly-projecting stop formations 124a are formed on the support arms 122 of the front housing body 110. The stop formations 124a are disposed distally with respect to the respective collars 124 of each support arm 122.

Referring to FIG. 46(a), the securing projections 253 are positioned so that, in an initial condition of the device when the interlock component 250a is in its first position and the rear housing body 140 is positioned to indicate a zero dose, the securing projections 253 are disposed on the distal side of the stop formations 124a. In other words, the securing projections 253 are at the same angular positions as the corresponding stop formations 124a. In this condition, the securing projections 253 cannot pass the stop formations 124a, so that movement of the interlock component 250a in the proximal direction, towards the second position, is prevented. Chamfers are provided on the distal side of each securing projection 253 and on the proximal side of each stop formation 124a to allow the securing projections 253 to pass the stop formations 124a when the interlock component 250a is inserted into the front housing body 110 during assembly of the device.

During the normal operating sequence of the device, the rear housing body 140 is turned to select a non-zero dose. The resulting turning movement of the upper sleeve part 258a of the interlock component 250a moves the securing projections 253 out of angular alignment with the stop formations 124a, as shown in FIG. 46(b). In this unsecured condition, the interlock component 250a is still in the first position but movement of the interlock component 250a in the proximal direction is no longer prevented. Thus, upon application of the device to an injection site, the securing projections 253 can pass the stop formations 124a and the interlock component 250a can move to the second position against the bias of the insertion spring, as shown in FIG. 46(c), allowing operation of the trigger button.

In this way, cooperation between the securing projections 253 of the interlock component 250a with the stop formations 124a of the front housing body 110 serves to secure the interlock component 250a in the first position to reduce the risk of accidental firing of the device, for example if the device were to be dropped. Another benefit of this arrangement is that the interlock component 250a cannot be moved out of its first position and the device cannot be fired until a non-zero dose has been selected by the user.

In another variant of the device (not illustrated), cooperation between the interlock component and the cap acts to secure the interlock component in the first position whilst the cap is in place. For example, the cap may be shaped to wedge the interlock component against the front housing body to prevent proximal movement of the interlock component until the cap is removed.

FIG. 47 is a cross-sectional view of an alternative carrier assembly 220a that could be used in place of the carrier assembly 220 described above with reference to FIG. 5. In the carrier assembly 220a of FIG. 47, an annular collar or sleeve 224a is disposed at the proximal end of the carrier support 222a. The sleeve 224a may be further secured to the carrier support 222a by any suitable means, for example by chemical and/or mechanical bonding.

The sleeve 224a defines a bore 225a for receiving the syringe body 12. A plurality of deformable wedge-shaped projections 230a are arranged around the internal surface of the bore 225a. In this case, two arcuate wedge-shaped projections 230a are provided, although fewer or more such projections could be present. The proximal end of the sleeve 224a extends beyond the proximal end of the carrier support 222a to provide an annular damping element 226a.

The sleeve 224a, the projections 230a and the damping element 226a provide the same functionality as the equivalent parts of the carrier assembly 220 described above with reference to FIG. 5. In particular, the sleeve 224a, and in particular the projections 230a, deform against the syringe body 12 to apply a frictional force that retards movement of the syringe body 12 with respect to the carrier assembly 220a.

In the FIG. 47 variant, the carrier support 222a comprises two guide legs 232a (only one of which can be seen in FIG. 47). The guide legs 232a are angularly spaced to define gaps therebetween. Each guide leg 232a is provided with a blocking projection 240a, a stop projection 242a and a lock projection 244a, each of which has the same function as the equivalent projections 240, 242, 244 of the carrier assembly 220 of FIG. 5. Each guide leg 232a of the carrier support 222a of FIG. 47 is also provided with latch members 236a that have the same function as the latch members 236 of the carrier assembly 220 of FIG. 5, although in the FIG. 47 variant the latch member 236a comprises a clip formation disposed on the outer surface of the respective guide leg 232a.

FIG. 48 is a cut-away view showing the alternative carrier assembly 220a in use with the modified interlock component 250a shown in FIG. 46. In this case, the interlock component 250a includes two guide arms 252a for guiding the carrier assembly 220a (only one of the guide arms 252a is visible in FIG. 48). The guide arms 252a are received in the spaces between the guide legs 232a of the carrier support 222a. Each of the guide arms 252a of the interlock component 250a is provided with a bracing formation or tab 256a on one side, so that each tab 256a extends circumferentially from the guide arm 252 towards the adjacent guide leg 232a of the carrier support 222a. The guide arms 252a and tabs 256a are dimensioned so that, when the interlock component 250a is in the first position, the guide arms 252a and tabs 256a form a bridge between the adjacent guide legs 232a of the carrier support 222a that prevents the guide legs 232a from deflecting inwardly. Accordingly, the carrier assembly 220a is locked in its initial position, with the blocking projections 240a and the lock projections 244a disposed on the distal and proximal sides of the collars 124 of the support arms 122 of the front housing body 110.

As the interlock component 250a is moved from the first position to the second position, each tab 256a moves into the clearance provided by a notch 248a in the adjacent guide leg 232a of the carrier support 222a. When in this position, the guide legs 232a are no longer braced against deflection by the interlock component 250a, so that the legs 232a can deflect inwardly to disengage from the collars 124 and release the carrier assembly 220a from its initial position during the insertion stroke of the device. It will be noted that, in this example, each guide arm 252a of the interlock component 250a is provided with a tab 256a on only one side and, correspondingly, each guide leg 232a of the carrier support 222a is provided with a notch 248a on only one side. It will however be appreciated that tabs and notches could be provided on both sides of the guide arms and guide legs respectively, if desired. In a further variant, the tabs are provided on the carrier support, and corresponding notches are provided in the interlock component.

In another variant of the device (not illustrated), a modified priming mechanism is provided. In this case, the shuttle member described above with reference to the first embodiment of the invention is omitted, and instead carrier tabs or other suitable carrier formations are provided on the cap itself for moving the syringe body in the proximal direction. In this case, the cap is guided for proximal movement during removal of the cap to displace the syringe body in the proximal direction, for example by an inclined formation that causes the cap to move proximally as it is turned to unlock the cap from the front housing body. In such cases, suitable formations may be provided in the front housing body to prevent proximal movement of needle shield and release the needle shield from the needle during the priming operation.

As will be apparent to the skilled person, many further variations and modifications of the devices and features described above are possible without departing from the scope of the invention as defined in the appended claims.

The invention claimed is:

1. A device for delivery of a medicament from a container having an outlet at a distal end of the container and a stopper for containing the medicament in the container, the device comprising:
   a housing;
   a plunger arranged to move in a distal direction to cooperate with the container;
   a drive mechanism comprising a trigger button, the drive mechanism being arranged to hold the plunger in a starting position and to move the plunger in the distal direction from the starting position upon displacement of the trigger button from a working position to a firing position;
   an interlock component received in the housing and arranged for movement with respect to the housing from a first position to a second position; and
   at least one flexible locking member arranged to cooperate with a stop face associated with the housing to prevent displacement of the trigger button to the firing position when the interlock component is in the first position,
      wherein the at least one flexible locking member is located on the trigger button,
      wherein the interlock component is not in contact with the at least one flexible locking member in the first position,
      wherein the interlock component is arranged to contact the at least one flexible locking member upon movement of the interlock component towards the second position, and
      wherein movement of the interlock component towards the second position causes bending of the flexible locking member away from the stop face to allow displacement of the trigger button to the firing position.

2. The device according to claim 1, wherein the flexible locking member is arranged to abut the stop face when the interlock component is in the first position, and wherein bending of the flexible locking member upon movement of the interlock component towards the second position causes the flexible locking member to move clear of the stop face.

3. The device according to claim 1, wherein the stop face prevents distal movement of the flexible locking member when the interlock component is in the first position.

4. The device according to claim 1, wherein a proximal part of the interlock component contacts the flexible locking member upon movement of the interlock component towards the second position.

5. The device according to claim 1, wherein the flexible locking member is associated with the interlock component, and comprises a blocking face arranged to block distal movement of the trigger button when the flexible locking member cooperates with the stop face.

6. The device according to claim 1, comprising a guide formation arranged to cooperate with the flexible locking member to cause further bending of the flexible locking member upon movement of the trigger button to the firing position.

7. The device according to claim 6, wherein the guide formation is associated with the housing.

8. The device according to claim 1, wherein a firing mechanism comprises a latching arrangement for latching the plunger in the starting position, and wherein the trigger button comprises a latch release member for releasing the latching arrangement upon movement of the trigger button to the fired position.

9. The device according to claim 8, wherein the interlock component cooperates with the latching arrangement to block the release of the latching arrangement when the interlock component is in the first position.

10. The device according to claim 8, wherein the latching arrangement comprises at least one latching arm associated with the plunger, wherein the latching arm is arranged to engage with the housing to latch the plunger in the starting position and the latch release member is arranged to disengage the latching arm from the housing upon movement of the trigger button to the firing position, and wherein the interlock component cooperates with the latching arm to prevent disengagement of the latching arm from the housing when the interlock component is in its first position, and the interlock component moves to release the latching arm upon movement of the interlock component towards its second position.

11. The device according to claim 1, comprising a securing mechanism for securing the interlock component in the first position, wherein the securing mechanism is releasable upon movement of an operating member of the device to allow movement of the interlock component to the second position.

12. The device according to claim 11, wherein movement of the operating member causes turning movement of the interlock component relative to the housing thereby to release the securing mechanism.

13. The device according to claim 11, wherein the operating member comprises a dose selector of the device, and wherein the securing mechanism releases the interlock component when a non-zero dose is selected.

14. The device according to claim 11, wherein the securing mechanism comprises a securing formation positioned for engagement with a stop formation to prevent movement of the interlock component out of the first position and movable out of engagement with the stop formation to release the securing mechanism upon movement of the operating member.

15. The device according to claim 1, wherein movement of the interlock component towards the second position causes axial movement of the flexible locking member relative to the housing.

16. The device according to claim 15, comprising a ramp formation arranged to cooperate with a control formation to bend the flexible locking member upon axial movement of the flexible locking member relative to the housing.

17. The device according to claim 16, wherein the ramp formation is disposed on the flexible locking member and wherein the control formation is associated with the housing.

18. The device according to claim 16, wherein the flexible locking member comprises a guide surface disposed on a distal side of the ramp formation, the guide surface being arranged to cooperate with the control formation upon further axial movement of the flexible locking member relative to the housing.

19. The device according to claim 1, wherein movement of the interlock component towards the second position causes movement of the trigger button relative to the housing from a stowed position to the working position.

20. The device according to claim 19, wherein the working position is proximal to the stowed position and a trigger position.

21. The device according to claim 1, wherein the interlock component is arranged for axial movement with respect to the housing.

22. The device according to claim 21, wherein a distal part of the interlock component protrudes from a distal end of the housing when the interlock component is in the first position, and wherein the second position is disposed proximally with respect to the first position.

23. An injection device for delivery of a medicament from a container having an outlet at a distal end of the container and a stopper for containing the medicament in the container, the device comprising:
a housing for receiving the container;
a drive mechanism arranged to move a drive element in a distal direction to cooperate with the container upon operation of the drive mechanism;
an interlock component received in the housing and arranged for movement with respect to the housing from a first position to a second position to switch the drive mechanism from a locked state to an operating state; and
a securing mechanism for securing the interlock component in the first position, wherein the securing mechanism is releasable upon movement of an operating member of the device to allow movement of the interlock component to the second position,
wherein movement of the operating member causes turning movement of the interlock component relative to the housing thereby to release the securing mechanism.

24. The injection device according to claim 23, wherein the operating member comprises a dose selector of the device, and wherein the securing mechanism releases the interlock component when a non-zero dose is selected.

25. The injection device according to claim 23, wherein the securing mechanism comprises a securing formation positioned for engagement with a stop formation to prevent movement of the interlock component out of the first position and movable out of engagement with the stop formation to release the securing mechanism upon movement of the operating member.

26. A device for delivery of a medicament from a container having an outlet at a distal end of the container and a stopper for containing the medicament in the container, the device comprising:
a housing;
a plunger arranged to move in a distal direction to cooperate with the container;
a drive mechanism comprising a trigger button, the drive mechanism being arranged to hold the plunger in a starting position and to move the plunger in the distal direction from the starting position upon displacement of the trigger button from a working position to a firing position;
an interlock component received in the housing and arranged for movement with respect to the housing from a first position to a second position; and
at least one flexible locking member arranged to cooperate with a stop face associated with the housing to prevent displacement of the trigger button to the firing position when the interlock component is in the first position,
wherein the at least one flexible locking member is located on the interlock component and comprises a blocking face arranged to block distal movement of the trigger button when the flexible locking member cooperates with the stop face,
wherein movement of the interlock component towards the second position causes bending of the flexible locking member away from the stop face to allow displacement of the trigger button to the firing position, and
wherein the at least one flexible locking member further comprises a proximal end face abutting the trigger button to block distal movement of the trigger button when the flexible locking member cooperates with the proximal end face.

* * * * *